US012325854B2

(12) United States Patent
Welstead et al.

(10) Patent No.: US 12,325,854 B2
(45) Date of Patent: Jun. 10, 2025

(54) CRISPR-CPF1-RELATED METHODS, COMPOSITIONS AND COMPONENTS FOR CANCER IMMUNOTHERAPY

(71) Applicant: EDITAS MEDICINE, INC., Cambridge, MA (US)

(72) Inventors: Gordon Grant Welstead, Cambridge, MA (US); Hariharan Jayaram, Cambridge, MA (US); Tongyao Wang, Malden, MA (US); John Anthony Zuris, Cambridge, MA (US); Christopher Borges, Reading, MA (US)

(73) Assignee: EDITAS MEDICINE, INC., Cambridge, MA (US)

( * ) Notice: Subject to any disclaimer, the term of this patent is extended or adjusted under 35 U.S.C. 154(b) by 390 days.

(21) Appl. No.: 16/121,152

(22) Filed: Sep. 4, 2018

(65) Prior Publication Data

US 2019/0062735 A1    Feb. 28, 2019

Related U.S. Application Data

(63) Continuation of application No. PCT/US2017/020598, filed on Mar. 3, 2017.

(60) Provisional application No. 62/304,057, filed on Mar. 4, 2016.

(51) Int. Cl.
| | |
|---|---|
| *C12N 15/85* | (2006.01) |
| *A61K 35/17* | (2015.01) |
| *C12N 5/0783* | (2010.01) |
| *C12N 9/22* | (2006.01) |
| *C12N 15/11* | (2006.01) |
| *C12N 15/113* | (2010.01) |
| *C12N 15/90* | (2006.01) |

(52) U.S. Cl.
CPC .............. *C12N 15/11* (2013.01); *A61K 35/17* (2013.01); *C12N 5/0636* (2013.01); *C12N 9/22* (2013.01); *C12N 15/113* (2013.01); *C12N 15/1138* (2013.01); *C12N 15/907* (2013.01); *C12N 2310/10* (2013.01); *C12N 2310/20* (2017.05); *C12N 2320/32* (2013.01); *C12N 2800/80* (2013.01)

(58) Field of Classification Search
None
See application file for complete search history.

(56) References Cited

U.S. PATENT DOCUMENTS

| | | | | |
|---|---|---|---|---|
| 2016/0184362 | A1* | 6/2016 | Duchateau | C12N 15/90 |
| | | | | 435/456 |
| 2016/0348073 | A1* | 12/2016 | Meissner | C12N 15/1138 |
| 2017/0175128 | A1* | 6/2017 | Welstead | C12N 15/113 |
| 2017/0333481 | A1* | 11/2017 | Jantz | C12N 5/0636 |

FOREIGN PATENT DOCUMENTS

| | | |
|---|---|---|
| WO | WO 2014/191128 A1 | 12/2014 |
| WO | WO 2015/136001 A1 | 9/2015 |
| WO | WO 2015/161276 A2 | 10/2015 |
| WO | WO 2016/073955 A2 | 5/2016 |
| WO | WO 2016/160721 A1 | 10/2016 |
| WO | WO 2016/205711 A1 | 12/2016 |

OTHER PUBLICATIONS

Meissner et al. Chapter 13 from Methods in Enzymology 546:273-295, 2014 (Year: 2014).*
Altschul et al., "Basic Local Alignment Search Tool," J. Mol. Biol. 215:403-410 (1990).
Altschul et al., "Gapped BLAST and PSI-BLAST: a new generation of protein database search programs," Nuc. Acids Res. 25(17):3389-3402 (1997).
Bae et al., "Cas-OFFinder: a fast and versatile algorithm that searches for potential off- target sites of Cas9 RNA-guided endonucleases," Bioinformatics 30(10):1473-1475 (2014).
Dotti et al., "Human cytotoxic T lymphocytes with reduced sensitivity to Fas-induced apoptosis," Blood 105:4677-4684 (2005).
Esvelt et al., "A system for the continuous directed evolution of biomolecules," Nature 472:499-503 (2011).
Fu et al., "Improving CRISPR-Cas nuclease specificity using truncated guide RNAs," Nature Biotechnology 32(3):279-284 (2014).
Heigwer et al., "E-CRISP: fast CRISPR target site identification," Nature Methods 11(2):122-123 (2014).
Hsu et al., "DNA targeting specificity of RNA-guided Cas9 nucleases," Nat Biotechnol 31(9):827-832 (2013).
International Search Report mailed May 16, 2017 in International Application No. PCT/US2017/020598.
Johnson et al., "Gene therapy with human and mouse T cell receptors mediates cancer regression and targets normal tissues expressing cognate antigen," Blood 114(3):535-546 (2009).
Kershaw et al., "Gene-engineered T cells for cancer therapy," Nat Rev Cancer 13:525-541 (2013).
Kochenderfer et al., "B-cell depletion and remissions of malignancy along with cytokine- associated toxicity in a clinical trial of anti-CD19 chimeric-antigen-receptor-transduced T cells," Blood 119(12):2709-2720 (2012).
Lamers et al., "Treatment of Metastatic Renal Cell Carcinoma with CAIX CAR-engineered T cells: Clinical Evaluation and Management of On-target Toxicity," Mol. Ther 21(4):904-912 (2013).
Lee et al., "Nonendocytic Delivery of Functional Engineered Nanoparticles into the Cytoplasm of Live Cells Using a Novel, High-Throughput Microfluidic Device," Nano Lett. 12:6322-6327 (2012).
Lei et al., "Knockdown of human bid gene expression enhances survival of CD8+ T cells," Immunol. Lett. 122:30-36 (2009).

(Continued)

*Primary Examiner* — Marcia S Noble
(74) *Attorney, Agent, or Firm* — Baker Botts L.L.P.

(57) ABSTRACT

CRISPR/Cpf1-related compositions and methods for treatment of cancer.

9 Claims, 8 Drawing Sheets

Specification includes a Sequence Listing.

(56) References Cited

OTHER PUBLICATIONS

Mali et al., "RNA-Guided Human Genome Engineering via Cas9," Science 339:823-826 (2013).
Mandal et al., "Efficient ablation of genes in human hematopoietic stem and effector cells using CRISPR/Cas9," Cell Stem Cell 15(5):643-652 (2014).
Myers et al., "Optimal alignments in linear space," Cabios 4:11-17 (1988).
Needleman et al., "A General Method Applicable to the Search for Similarities in the Amino Acid Sequence of Two Proteins," J. Mol. Biol. 48:443-453 (1970).
Pattanayak et al., "High-throughput profiling of off-target DNA cleavage reveals RNA-programmed Cas9 nuclease specificity," Nature Biotechnology 31(9):839-843 (2013).
Pearson et al., "Improved tools for biological sequence comparison," PNAS USA 85:2444-2448 (1988).
Provasi et al., "Editing T cell specificity towards leukemia by zinc finger nucleases and lentiviral gene transfer," Nature Medicine 18(5):807-815 (2012).
Riolobos et al., "HLA Engineering of Human Pluripotent Stem Cells," Mol. Ther. 21(6):1232-1241 (2013).
Shrikant et al., "CTLA-4 Blockade Reverses CD8+ T Cell Tolerance to Tumor by a CD4+ T Cell-and IL-2-Dependent Mechanism," Immunity 11:483-493 (1999).
Smith et al., "Comparison of Biosequences," Adv. Appl. Math. 2:482-489 (1981).
Stromnes et al., "Abrogating Cbl-b in effector CD8+ T cells improves the efficacy of adoptive therapy of leukemia in mice," J. Clin. Invest. 120(10):3722-3734 (2010).
Stromnes et al., "Abrogation of Src Homology Region 2 Domain-Containing Phosphatase 1 in Tumor-Specific T Cells Improves Efficacy of Adoptive Immunotherapy by Enhancing the Effector Function and Accumulation of Short-Lived Effector T Cells In Vivo," J. Immunol. 189:1812-1825 (2012).
Torikai et al., "A foundation for universal T-cell based immunotherapy: T cells engineered to express a CD19-specific chimeric-antigen-receptor and eliminate expression of endogenous TCR," Blood 119(24):5697-5705 (2012).
Warren et al., "Clinical studies of regional and systemic gene therapy with autologous CC49-ζ modified T cells in colorectal cancer metastatic to the liver," Cancer Gene Ther 5(6):S1-S2 (1998).
Xiao et al., "CasOT: a genome-wide Cas9/gRNA off-target searching tool," Bioinformatics 30(8):1180-1182 (2014).
Zetsche et al., "Cpf1 Is a Single RNA-Guided Endonuclease of a Class 2 CRISPR-Cas System," Cell 163:759-771 (2015).
Notice of Reasons for Rejection for corresponding Japanese Patent Application No. 2018-546483 issued Mar. 15, 2022.
Osborn et al., "Evaluation of TCR Gene Editing Achieved by TALENs, CRISPR/Cas9, and megaTAL Nucleases," Mol. Ther., vol. 24, No. 3, 570-581 (2016).
Doench et al., "Optimized sgRNA design to maximize activity and minimize off-target effects of CRISPR-Cas9," Nature Biotechnology 34:184-191 (2016).

\* cited by examiner

CRISPR-CPF1-RELATED METHODS, COMPOSITIONS AND COMPONENTS FOR CANCER IMMUNOTHERAPY

CROSS REFERENCE TO RELATED APPLICATIONS

This application is a Continuation of International Patent Application No. PCT/US17/20598 filed Mar. 3, 2017, which claims priority to U.S. Provisional Application No. 62/304,057, filed Mar. 4, 2016, the contents of each of which are incorporated by reference in their entireties herein, and priority to each of which is claimed.

SEQUENCE LISTING

The specification further incorporates by reference the Sequence Listing submitted herewith via EFS on Sep. 4, 2018. Pursuant to 37 C.F.R. § 1.52(e)(5), the Sequence Listing text file, identified as 0841770198SL2.txt, is 738,470 bytes and was created on Nov. 14, 2018. The entire contents of the Sequence Listing are hereby incorporated by reference. The Sequence Listing does not extend beyond the scope of the specification and thus does not contain new matter.

FIELD OF THE PRESENTLY DISCLOSED SUBJECT MATTER

The invention relates to CRISPR/Cpf1-related methods, compositions and components for editing a target nucleic acid sequence, or modulating expression of a target nucleic acid sequence, and applications thereof in connection with cancer immunotherapy comprising adoptive transfer of engineered T cells or T cell precursors.

BACKGROUND

Adoptive transfer of genetically engineered T cells has entered clinical testing as a cancer therapeutic modality. Typically, the approach consists of the following steps: 1) obtaining leukocytes from the subject by apheresis; 2) selecting/enriching for T cells; 3) activating the T cells by cytokine treatment; 4) introducing cloned T cell receptor (TCR) genes or a chimeric antigen receptor (CAR) gene by retroviral transduction, lentiviral transduction or electroporation; 5) expanding the T cells by cytokine treatment; 6) conditioning the subject, usually by lymphodepletion; and 7) infusion of the engineered T cells into the subject.

Sources of cloned TCR genes (TRAC and TRBC) include rare T cell populations isolated from individuals with particular malignancies and T cell clones isolated from T cell receptor-humanized mice immunized with specific tumor antigens or tumor cells. Following adoptive transfer, TCR-engineered T cells recognize their cognate antigen peptides presented by major histocompatibility complex (MHC) proteins on the tumor cell surface. Antigen engagement stimulates signal transduction pathways leading to T cell activation and proliferation. Stimulated T cells then mount a cytotoxic anti-tumor cell response, typically involving a secreted complex comprising Granzyme B, perforin and granulysin, inducing tumor cell apoptosis.

Chimeric antigen receptor (CAR) genes encode artificial T cell receptors comprising an extra-cellular tumor antigen binding domain, typically derived from the single-chain antibody variable fragment (scFv) domain of a monoclonal antibody, fused via hinge and transmembrane domains to a cytoplasmic effector domain. The effector domain is typically derived from the CD3-zeta chain of the T cell co-receptor complex, and can also include domains derived from CD28 and/or CD137 receptor proteins. The CAR extra-cellular domain binds the tumor antigen in an MHC-independent manner leading to T cell activation and proliferation, culminating in cytotoxic anti-tumor activity as described for TCR engineered T cells.

To date, at least 15 different tumor antigens have been targeted in clinical trials of engineered T cells. In several trials, anti-tumor activity has been reported. The greatest success has been achieved in hematologic malignancies. For example, adoptive transfer of CAR-T cells engineered to target the B cell antigen, CD19, led to multiple partial and complete responses in subjects with lymphoma, acute lymphoblastic leukemia, acute lymphocytic leukemia and B-cell acute lymphocytic leukemia. In contrast, trials targeting other tumor types, especially solid tumors, including renal cell carcinoma, neuroblastoma, colorectal cancer, breast cancer, ovarian cancer, melanoma, sarcoma and prostate cancer, have been less successful. In many of these trials, very few patients experienced objective responses. Thus, there is a need to improve the anti-tumor efficacy of adoptively transferred engineered T cells.

SUMMARY OF THE PRESENTLY DISCLOSED SUBJECT MATTER

Methods and compositions disclosed herein provide for the treatment of cancer using an immunotherapy approach comprising administration of genetically engineered T cells or T cell precursors to a subject. An approach to treat a subject suffering from cancer is to isolate T cells from the subject, genetically modify them to target an antigen expressed by the cancer cells, then re-introduce them into the subject; a process referred to as adoptive T cell transfer. Methods to genetically modify T cells include introduction of T cell receptor (TCR) or chimeric antigen receptor (CAR) genes encoding trans-membrane TCR or CAR proteins, respectively, which specifically recognize particular cancer antigens. In certain embodiments, engagement of the tumor-expressed antigen with the antigen binding domain of the TCR or CAR protein initiates a signaling cascade leading to T cell activation, proliferation and, ultimately, destruction of the cancer cell via a cytotoxic immune response (Kershaw et al., 2013 NatRevCancer 13, 525-541).

Adoptive T cell transfer utilizing genetically modified T cells has entered clinical testing as a therapeutic for solid and hematologic malignancies. Results to date have been mixed. In hematologic malignancies (especially lymphoma, Chronic lymphocytic leukemia (CLL) and Acute lymphocytic leukemia (ALL)), the majority of patients in several Phase 1 and 2 trials exhibited at least a partial response, with some exhibiting complete responses (Kochenderfer, J. N. et al., 2012 Blood 119, 2709-2720). However, in most tumor types (including melanoma, renal cell carcinoma and colorectal cancer), fewer responses have been observed (Johnson, L. A. et al., 2009 Blood 114, 535-546; Lamers, C. H. et al., 2013 Mol. Ther. 21, 904-912; Warren, R. S. et al., 1998 Cancer Gene Ther. 5, S1-S2). Thus, there exists a need to improve the efficacy of adoptive transfer of modified T cells in cancer treatment.

Factors limiting the efficacy of genetically modified T cells as cancer therapeutics include (1) T cell proliferation, e.g., limited proliferation of T cells following adoptive transfer; (2) T cell survival, e.g., induction of T cell apoptosis by factors in the tumor environment; and (3) T cell function, e.g., inhibition of cytotoxic T cell function by inhibitory factors secreted by host immune cells and cancer cells. The methods and compositions disclosed herein address one or more of these limitations by modifying the expression of T cell-expressed genes that influence T cell proliferation, survival and/or function.

In certain embodiments, methods and compositions disclosed herein can be used to affect T cell proliferation (e.g., by inactivating genes that inhibit T cell proliferation). In certain embodiments, methods and compositions disclosed herein can be used to affect T cell survival (e.g., by inactivating genes mediating T cell apoptosis). In certain embodiments, methods and composition disclosed herein can be used to affect T cell function (e.g., by inactivating genes encoding immunosuppressive and inhibitory (e.g., anergy-inducing) signaling factors). In certain embodiments, methods and composition disclosed herein can be used to improve T cell persistence. In certain embodiments, the methods and compositions disclosed herein can be utilized individually or in combination to affect one or more of the factors limiting the efficacy of genetically modified T cells as cancer therapeutics, e.g., T cell proliferation, T cell survival, T cell function, T cell persistence, or any combination thereof.

Methods and compositions disclosed herein can be used to affect T cell proliferation, survival, persistence, and/or function by altering one or more T-cell expressed gene, e.g., one or more of FAS, BID, CTLA4, PDCD1, CBLB, PTPN6, B2M, TRAC and TRBC genes. In certain embodiments, methods and compositions disclosed herein can be used to affect T cell proliferation by altering one or more T-cell expressed gene, e.g., the CBLB and/or PTPN6 gene. In certain embodiments, methods and compositions disclosed herein can be used to affect T cell survival by altering one or more T-cell expressed gene, e.g., FAS and/or BID gene. In certain embodiments, methods and compositions disclosed herein can be used to affect T cell function by altering one or more T-cell expressed gene, e.g., CTLA4, PDCD1, TRAC, and/or TRBC gene. In certain embodiments, methods and compositions disclosed herein can be used to improve T cell persistence by altering B2M gene.

In certain embodiments, one or more T-cell expressed gene, including, but not limited to, FAS, BID, CTLA4, PDCD1, CBLB, PTPN6, B2M, TRAC, and TRBC genes, are independently targeted as a targeted knockout, e.g., to influence T cell proliferation, survival, persistence, and/or function. In certain embodiments, a presently disclosed method comprises knocking out one T-cell expressed gene (e.g., one selected from the group consisting of FAS, BID, CTLA4, PDCD1, CBLB, PTPN6, B2M, TRAC and TRBC genes). In certain embodiments, a presently disclosed method comprises independently knocking out two T-cell expressed genes (e.g., two selected from the group consisting of FAS, BID, CTLA4, PDCD1, CBLB, PTPN6, B2M, TRAC and TRBC genes). In certain embodiments, a presently disclosed method comprises independently knocking out three T-cell expressed genes, e.g., three selected from the group consisting of FAS, BID, CTLA4, PDCD1, CBLB, PTPN6, B2M, TRAC and TRBC genes. In certain embodiments, a presently disclosed method comprises independently knocking out four T-cell expressed genes, e.g., four selected from the group consisting of FAS, BID, CTLA4, PDCD1, CBLB, PTPN6, B2M, TRAC and TRBC genes. In certain embodiments, a presently disclosed method comprises independently knocking out five T-cell expressed genes, e.g., five selected from the group consisting of FAS, BID, CTLA4, PDCD1, CBLB, PTPN6, B2M, TRAC and TRBC genes. In certain embodiments, a presently disclosed method comprises independently knocking outwn six T-cell expressed genes, e.g., six selected from the group consisting of FAS, BID, CTLA4, PDCD1, CBLB, PTPN6, B2M, TRAC and TRBC genes. In certain embodiments, a presently disclosed method comprises independently knocking out seven T-cell expressed genes, e.g., seven selected from the group consisting of FAS, BID, CTLA4, PDCD1, CBLB, PTPN6, B2M, TRAC and TRBC genes. In certain embodiments, a presently disclosed method comprises independently knocking out eight T-cell expressed genes, e.g., each of FAS, BID, CTLA4, PDCD1, CBLB, PTPN6, B2M, TRAC and TRBC genes.

In addition to the genes described above, a number of other T-cell expressed genes may be targeted to affect the efficacy of engineered T cells. These genes include, but are not limited to, TGFBRI, TGFBRII and TGFBRIII (Kershaw et al. 2013 NatRevCancer 13, 525-541). In certain embodiments, one or more of TGFBRI, TGFBRII and TGFBRIII genes can be altered either individually or in combination using the methods disclosed herein. In certain embodiments, one or more of TGFBRI, TGFBRII and TGFBRIII genes can be altered either individually or in combination with any one or more of the eight genes described above (i.e., FAS, BID, CTLA4, PDCD1, CBLB, PTPN6, B2M, TRAC and TRBC genes) using the presently disclosed methods.

In certain embodiments, methods and compositions disclosed herein alter FAS, BID, CTLA4, PDCD1, CBLB, PTPN6, B2M, TRAC and/or TRBC genes by targeting a position (e.g., a knockout position) of the gene(s), e.g., a position within the non-coding region (e.g., the promoter region) or a position within the coding region, or by targeting a transcribed sequence of the gene(s), e.g., an intronic sequence or an exonic sequence. In certain embodiments, a coding sequence, e.g., a coding region, e.g., an early coding region of the gene(s) (e.g., FAS, BID, CTLA4, PDCD1, CBLB, PTPN6, B2M, TRAC and/or TRBC genes) is targeted for alteration and knockout of expression. In certain embodiments, a position in the non-coding region (e.g., the promoter region) of the T-cell expressed gene(s) (e.g., FAS, BID, CTLA4, PDCD1, CBLB, PTPN6, B2M, TRAC and/or TRBC genes) is targeted for alteration and knockout of expression of the T-cell expressed gene(s).

In certain embodiments, the methods and compositions disclosed herein alter FAS, BID, CTLA4, PDCD1, CBLB, PTPN6, B2M, TRAC and/or TRBC genes by targeting a coding sequence of the gene(s). In certain embodiments, the coding sequence is an early coding sequence. In certain embodiments, the coding sequence of the gene(s) is targeted for knockout of expression of the T-cell expressed gene(s).

In certain embodiments, the methods and compositions disclosed herein alter FAS, BID, CTLA4, PDCD1, CBLB, PTPN6, B2M, TRAC and/or TRBC genes by targeting a non-coding sequence of the gene(s). In certain embodiments, the non-coding sequence comprises a sequence within the promoter region, an enhancer sequence, an intronic sequence, a sequence within the 3'UTR, a polyadenylation signal sequence, or a combination thereof. In certain embodiments, the non-coding sequence of the gene(s) is targeted for knockout of expression of the gene(s).

In certain embodiments, a presently disclosed method comprises knock outing one or two alleles of FAS, BID, CTLA4, PDCD1, CBLB, PTPN6, B2M, TRAC and/or TRBC gene(s), e.g., by inducing an alteration in the gene(s). In certain embodiments, the alteration comprises an insertion, a deletion, a mutation, or a combination thereof.

In certain embodiments, the targeted knockout approach is mediated by non-homologous end joining (NHEJ) using a CRISPR/Cpf1 system comprising a Cpf1 enzyme.

"T cell target FAS knockout position", as used herein, refers to a position in FAS gene, which if altered, e.g., by NHEJ-mediated alteration, results in a reduction or elimination of expression of functional FAS gene product (e.g., knockout of expression of functional FAS gene product). In certain embodiments, the position is in the coding region of FAS gene, e.g., an early coding region.

"T cell target BID knockout position", as used herein, refers to a position in BID gene, which if altered, e.g., by NHEJ-mediated alteration, results in a reduction or elimination of expression of functional BID gene product (e.g., knockout of expression of functional BID gene product). In certain embodiments, the position is in the coding region of BID gene, e.g., an early coding region.

"T cell target CTLA4 knockout position", as used herein, refers to a position in CTLA4 gene, which if altered, e.g., by NHEJ-mediated alteration, results in a reduction or elimination of expression of functional CTLA4 gene product (e.g., knockout of expression of functional CTLA4 gene product). In certain embodiments, the position is in the coding region of CTLA4, e.g., an early coding region.

"T cell target PDCD1 knockout position", as used herein, refers to a position in PDCD1 gene, which if altered, e.g., by NHEJ-mediated alteration, results in a reduction or elimination of expression of functional PDCD1 gene product (e.g., knockout of expression of functional PDCD1 gene product). In certain embodiments, the position is in the coding region of PDCD1 gene, e.g., an early coding region.

"T cell target CBLB knockout position", as used herein, refers to a position in CBLB gene, which if altered, e.g., by NHEJ-mediated alteration, results in a reduction or elimination of expression of functional CBLB gene product (e.g., knockout of expression of functional CBLB gene product). In certain embodiments, the position is in the coding region of CBLB gene, e.g., an early coding region.

"T cell target PTPN6 knockout position", as used herein, refers to a position in PTPN6 gene, which if altered, e.g., by NHEJ-mediated alteration, results in a reduction or elimination of expression of functional PTPN6 gene product (e.g., knockout of expression of functional PTPN6 gene product). In certain embodiments, the position is in the coding region of PTPN6 gene, e.g., an early coding region.

"T cell target B2M knockout position", as used herein, refers to a position in B2M gene, which if altered, e.g., by NHEJ-mediated alteration, results in a reduction or elimination of expression of functional B2M gene product (e.g., knockout of expression of functional B2M gene product). In certain embodiments, the position is in the coding region of B2M gene, e.g., an early coding region.

"T cell target TRAC knockout position", as used herein, refers to a position in TRAC gene, which if altered, e.g., by NHEJ-mediated alteration, results in a reduction or elimination of expression of functional TRAC gene product (e.g., knockout of expression of functional TRAC gene product). In certain embodiments, the position is in the coding region of TRAC gene, e.g., an early coding region.

"T cell target TRBC knockout position", as used herein, refers to a position in TRBC gene, which if altered, e.g., by NHEJ-mediated alteration, results in a reduction or elimination of expression of functional TRBC gene product (e.g., knockout of expression of functional TRBC gene product). In certain embodiments, the position is in the coding region of TRBC gene, e.g., an early coding region.

"T cell target FAS position", as used herein, refers to any of the T cell target FAS knockout position, as described herein.

"T cell target BID position", as used herein, refers to any of the T cell target BID knockout position, as described herein.

"T cell target CTLA4 position", as used herein, refers to any of the T cell target CTLA4 knockout position, as described herein.

"T cell target PDCD1 position", as used herein, refers to any of the T cell target PDCD1 knockout position, as described herein.

"T cell target CBLB position", as used herein, refers to any of the T cell target CBLB knockout position, as described herein.

"T cell target PTPN6 position", as used herein, refers to any of the T cell target PTPN6 knockout position, as described herein.

"T cell target B2M position", as used herein, refers to any of the T cell target B2M knockout position, as described herein.

"T cell target TRAC position", as used herein, refers to any of the T cell target TRAC knockout position, as described herein.

"T cell target TRBC position", as used herein, refers to any of the T cell target TRBC knockout position, as described herein.

"T cell target knockout position", as used herein, refers to any of the T cell target FAS knockout position, T cell target BID knockout position, T cell target CTLA4 knockout position, T cell target PDCD1 knockout position, T cell target CBLB knockout position, T cell target PTPN6 knockout position, T cell target B2M knockout position, T cell target TRAC knockout position, or T cell target TRBC knockout position, as described herein.

"T cell target position", as used in herein, refers to any of a T cell target knockout position, as described herein.

In one aspect, disclosed herein is a gRNA molecule, e.g., an isolated or non-naturally occurring gRNA molecule, comprising a targeting domain which is complementary with a target domain from one T-cell expressed gene selected from the group consisting of FAS, BID, CTLA4, PDCD1, CBLB, PTPN6, B2M, TRAC and TRBC gene.

In certain embodiments, the targeting domain of the gRNA molecule is configured to provide a cleavage event, e.g., a double strand break, sufficiently close to a T cell target position (e.g., a T cell target knockout position) in FAS, BID, CTLA4, PDCD1, CBLB, PTPN6, B2M, TRAC and/or TRBC genes to allow alteration, e.g., alteration associated with NHEJ, of a T cell target position (e.g., a T cell target knockout position) in FAS, BID, CTLA4, PDCD1, CBLB, PTPN6, B2M, TRAC and/or TRBC genes. In certain embodiments, the targeting domain is configured such that a cleavage event, e.g., a double strand, is positioned within 1, 2, 3, 4, 5, 10, 15, 20, 25, 30, 35, 40, 45, 50, 60, 70, 80, 90, 100, 150, 200, 250, 300, 350, 400, 450, or 500 nucleotides of a T cell target position (e.g., a T cell target knockout position). The double strand break can be positioned upstream or downstream of a T cell knockout target position (e.g., a T cell target knockout position) in FAS, BID, CTLA4, PDCD1, CBLB, PTPN6, B2M, TRAC and/or TRBC genes.

In certain embodiments, a second gRNA molecule comprising a second targeting domain is configured to provide a cleavage event, e.g., a double strand break, sufficiently close to the T cell target position in FAS, BID, CTLA4, PDCD1, CBLB, PTPN6, B2M, TRAC and/or TRBC genes, to allow alteration, e.g., alteration associated with NHEJ, of the T cell target position in FAS, BID, CTLA4, PDCD1, CBLB, PTPN6, B2M, TRAC and/or TRBC gene, either alone or in combination with the break positioned by the first gRNA molecule. In certain embodiments, the targeting domains of the first and second gRNA molecules are configured such that a double strand break is positioned, independently for each of the gRNA molecules, within 1, 2, 3, 4, 5, 10, 15, 20, 25, 30, 35, 40, 45, 50, 60, 70, 80, 90, 100, 150, 200, 250, 300, 350, 400, 450, or 500 nucleotides of the target position. In certain embodiments, the two sets of double strand breaks are positioned on both sides of a nucleotide of a T cell target position (e.g., a T cell target knockout position) in FAS, BID, CTLA4, PDCD1, CBLB, PTPN6, B2M, TRAC and/or TRBC genes. In certain embodiments, the two sets of double strand breaks are positioned on one side, e.g., upstream or downstream, of a nucleotide of a T cell target position (e.g., a T cell target knockout position) in FAS, BID, CTLA4, PDCD1, CBLB, PTPN6, B2M, TRAC and/or TRBC genes. In certain embodiments, a double strand break can be accompanied by an additional double strand break, positioned by a second gRNA molecule, as is discussed below. For example, the targeting domain of a first gRNA molecule is configured such that a double strand break is positioned upstream of a T cell target position in FAS, BID, CTLA4, PDCD1, CBLB, PTPN6, B2M, TRAC and/or TRBC gene(s), e.g., within 1, 2, 3, 4, 5, 10, 15, 20, 25, 30, 35, 40, 45, 50, 60, 70, 80, 90, 100, 150, 200, 250, 300, 350, 400, 450, or 500 nucleotides of the target position; and the targeting domain of a second gRNA molecule is configured such that a double strand break is positioned downstream of a T cell target position in FAS, BID, CTLA4, CBLB, PTPN6, B2M, TRAC and/or TRBC genes, e.g., within 1, 2, 3, 4, 5, 10, 15, 20, 25, 30, 35, 40, 45, 50, 60, 70, 80, 90, 100, 150, 200, 250, 300, 350, 400, 450, or 500 nucleotides of the target position.

In certain embodiments, when two or more gRNAs are used to position two or more cleavage events, e.g., two sets of double stranded breaks, in a target nucleic acid, and the two or more cleavage events are made by the same or different Cpf1 proteins. In certain embodiments, when two gRNAs are used to position two sets of double stranded breaks in a target nucleic acid, a single Cpf1 nuclease is used to create both double stranded breaks. In certain embodiments, when two or more Cpf1 proteins are used, the Cpf1 proteins are from different species.

When more than one T-cell expressed gene is targeted for alteration in a cell, the targeted nucleic acids may be altered, e.g., cleaved, by one or more Cpf1 protein. For example, if two genes are targeted for alteration, e.g., both T-cell expressed genes are targeted for knockout, the same or a different Cpf1 protein may be used to target each gene. In certain embodiments, both T-cell expressed genes (or each gene targeted in a cell), are cleaved by a Cpf1 nuclease to generate a double stranded break. In certain embodiments, both T-cell expressed genes (or each gene targeted in a cell), are cleaved by a Cpf1 molecule to generate a double stranded break. In certain embodiments, one or more T-cell expressed gene in a cell may be altered by cleavage with a Cpf1 nuclease. When two or more Cpf1 proteins are used to cut a target nucleic acid, e.g., different genes in a cell, the Cpf1 proteins may be from different bacterial species. For example, one or more T-cell expressed genes in a cell may be altered by cleavage with a Cpf1 protein from one bacterial species, and one or more T-cell expressed gene in the same cell may be altered by cleavage with a Cpf1 protein from a different bacterial species. In certain embodiments, when two or more Cpf1 proteins from different species are used, they may be delivered at the same time or delivered sequentially to control specificity of cleavage in the desired gene at the desired position in the target nucleic acid.

In certain embodiments, the targeting domain of the first gRNA molecule and the targeting domain of the second gRNA molecules are complementary to opposite strands of the target nucleic acid molecule. In certain embodiments, the gRNA molecule and the second gRNA molecule are configured such that the PAMs are oriented outward.

In certain embodiments, a position in the coding region, e.g., an early coding region, of FAS, BID, CTLA4, PDCD1, CBLB, PTPN6, B2M, TRAC and/or TRBC gene(s) is targeted, e.g., for knockout. In certain embodiments, the targeting domain comprises a sequence that is identical to, or differs by no more than 1, no more than 2, no more than 3, no more than 4 or no more than 5 nucleotides from a nucleotide sequence selected from SEQ ID NOS: 1-3707. In certain embodiments, the targeting domain comprises a nucleotide sequence selected from SEQ ID NOS: 1-3707:

In certain embodiments, when the T cell target knockout position is the FAS coding region, e.g., an early coding region, and more than one gRNA is used to position breaks, e.g., two double stranded breaks, e.g., to create one or more indels, in the target nucleic acid sequence, each guide RNA is independently selected from SEQ ID NOS: 2326-3094.

In certain embodiments, when the T cell target knockout position is the BID coding region, e.g., an early coding region, and more than one gRNA is used to position breaks, e.g., two double stranded breaks, e.g., to create one or more indels, in the target nucleic acid sequence, each guide RNA is independently selected from SEQ ID NOS: 3284-3385.

In certain embodiments, when the T cell target knockout position is the CTLA4 coding region, e.g., an early coding region, and more than one gRNA is used to position breaks, e.g., two double stranded breaks, e.g., to create one or more indels, in the target nucleic acid sequence, each guide RNA is independently selected from SEQ ID NOS: 64-370.

In certain embodiments, when the T cell target knockout position is the PDCD1 coding region, e.g., an early coding region, and more than one gRNA is used to position breaks, e.g., two double stranded breaks, e.g., to create one or more indels, in the target nucleic acid sequence, each guide RNA is independently selected from SEQ ID NOS: 1-63.

In certain embodiments, when the T cell target knockout position is the CBLB coding region, e.g., an early coding region, and more than one gRNA is used to position breaks, e.g., two double stranded breaks, e.g., to create one or more indels, in the target nucleic acid sequence, each guide RNA is independently selected from SEQ ID NOS: 504-2325.

In certain embodiments, when the T cell target knockout position is the PTPN6 coding region, e.g., an early coding region, and more than one gRNA is used to position breaks, e.g., two double stranded breaks, e.g., to create one or more indels, in the target nucleic acid sequence, each guide RNA is independently selected from SEQ ID NOS: 371-503.

In certain embodiments, when the T cell target knockout position is the B2M coding region, e.g., an early coding region, and more than one gRNA is used to position breaks, e.g., two double stranded breaks, e.g., to create one or more indels, in the target nucleic acid sequence, each guide RNA is independently selected from SEQ ID NOS: 3095-3283.

In certain embodiments, when the T cell target knockout position is the TRAC coding region, e.g., an early coding region, and more than one gRNA is used to position breaks, e.g., two double stranded breaks, e.g., to create one or more indels, in the target nucleic acid sequence, each guide RNA is independently selected from SEQ ID NOS: 3386-3588.

In certain embodiments, when the T cell target knockout position is the TRBC coding region, e.g., an early coding region, and more than one gRNA is used to position breaks, e.g., two double stranded breaks, e.g., to create one or more indels, in the target nucleic acid sequence, each guide RNA is independently selected from SEQ ID NOS: 3589-3707.

In certain embodiments, gRNA further comprises a direct repeat domain. In certain embodiments, the direct repeat domain is 15-20 nucleotides in length. In certain embodiments, the direct repeat domain comprises a nucleotide sequence selected from the group consisting of SEQ ID NOS: 3708-3710.

In certain embodiments, the gRNA molecule is a unimodular (also referred to as "unimolecular") gRNA. In certain embodiments, the targeting domain is 15-25 nucleotides in length. In certain embodiments, the targeting domain is 18 nucleotides in length. In certain embodiments, the targeting domain is 19 nucleotides in length. In certain embodiments, the targeting domain is 20 nucleotides in length. In certain embodiments, the targeting domain is 21 nucleotides in length. In certain embodiments, the targeting domain is 22 nucleotides in length. In certain embodiments, the targeting domain is 23 nucleotides in length.

A cleavage event, e.g., a double strand break, is generated by a Cpf1 molecule. In certain embodiments, the Cpf1 molecule catalyzes a double strand break.

Additionally, the presently disclosed subject matter provides a nucleic acid composition, e.g., an isolated or non-naturally occurring nucleic acid composition, e.g., DNA composition, that comprises (a) a first nucleotide sequence that encodes a first gRNA molecule as described above. In certain embodiments, the nucleic acid composition further comprises (b) a second nucleotide sequence that encodes a Cpf1 molecule. The Cpf1 molecule can form a double strand break in a target nucleic acid. In certain embodiments, the Cpf1 molecule is a selected from the group consisting of *Acidaminococcus* sp. strain BV3L6 Cpf1 molecule (AsCpf1), *Lachnospiraceae bacterium* ND2006 Cpf1 molecule (LbCpf1), and *Lachnospiraceae bacterium* MA2020 (Lb2Cpf1). In certain embodiments the second nucleotide sequence is set forth in SEQ ID NO: 3722, SEQ ID NO: 3723, or SEQ ID NO: 3724.

In certain embodiments, the nucleic acid composition further (c) a third nucleotide sequence that encodes a second gRNA molecule comprising a targeting domain that is complementary with a target domain from one T-cell expressed gene selected from the group consisting of FAS, BID, CTLA4, PDCD1, CBLB, PTPN6, B2M, TRAC and TRBC genes. In certain embodiments, the second gRNA targets the same T cell target position as the first gRNA molecule.

In certain embodiments, (a) and (b) are present on one nucleic acid molecule, e.g., one vector, e.g., one viral vector, e.g., an AAV vector. Exemplary AAV vectors that may be used in any of the described compositions and methods include an AAV1 vector, a modified AAV1 vector, an AAV2 vector, a modified AAV2 vector, an AAV3 vector, an AAV4 vector, a modified AAV4 vector, an AAV5 vector, a modified AAV5 vector, a modified AAV3 vector, an AAV6 vector, a modified AAV6 vector, an AAV7 vector, a modified AAV7 vector, an AAV8 vector, an AAV5 vector an AAV.rh10 vector, a modified AAV.rh10 vector, an AAV.rh32/33 vector, a modified AAV.rh32/33 vector, an AAV.rh43 vector, a modified AAV.rh43 vector, an AAV.rh64R1 vector, and a modified AAV.rh64R1 vector. In certain embodiments, (a) is present on a first nucleic acid molecule, e.g. a first vector, e.g., a first viral vector, e.g., a first AAV vector; and (b) is present on a second nucleic acid molecule, e.g., a second vector, e.g., a second vector, e.g., a second AAV vector. The first and second nucleic acid molecules may be AAV vectors.

In certain embodiments, (a) and (c) are be present on one nucleic acid molecule, e.g., one vector, e.g., one viral vector, e.g., one AAV vector. In certain embodiments, (a) and (c) are on different vectors. For example, (a) may be present on a first nucleic acid molecule, e.g. a first vector, e.g., a first viral vector, e.g., a first AAV vector; and (c) may be present on a second nucleic acid molecule, e.g., a second vector, e.g., a second vector, e.g., a second AAV vector. In certain embodiments, the first and second nucleic acid molecules are AAV vectors.

In certain embodiments, (a), (b), and (c) are present on one nucleic acid molecule, e.g., one vector, e.g., one viral vector, e.g., an AAV vector. In certain embodiments, the nucleic acid molecule is an AAV vector. In certain embodiments, one of (a), (b), and (c) is present on a first nucleic acid molecule, e.g., a first vector, e.g., a first viral vector, e.g., a first AAV vector; and a second and third of (a), (b), and (c) is encoded on a second nucleic acid molecule, e.g., a second vector, e.g., a second vector, e.g., a second AAV vector. The first and second nucleic acid molecule may be AAV vectors.

In certain embodiments, (a) is present on a first nucleic acid molecule, e.g., a first vector, e.g., a first viral vector, a first AAV vector; and (b) and (c) are present on a second nucleic acid molecule, e.g., a second vector, e.g., a second vector, e.g., a second AAV vector. The first and second nucleic acid molecule may be AAV vectors.

In certain embodiments, (b) is present on a first nucleic acid molecule, e.g., a first vector, e.g., a first viral vector, e.g., a first AAV vector; and (a) and (c) are present on a second nucleic acid molecule, e.g., a second vector, e.g., a second vector, e.g., a second AAV vector. The first and second nucleic acid molecule may be AAV vectors.

In certain embodiments, (c) is present on a first nucleic acid molecule, e.g., a first vector, e.g., a first viral vector, e.g., a first AAV vector; and (b) and (a) are present on a second nucleic acid molecule, e.g., a second vector, e.g., a second vector, e.g., a second AAV vector. The first and second nucleic acid molecule may be AAV vectors.

In certain embodiments, each of (a), (b) and (c)(i) are present on different nucleic acid molecules, e.g., different vectors, e.g., different viral vectors, e.g., different AAV vector. For example, (a) may be on a first nucleic acid molecule, (b) on a second nucleic acid molecule, and (c)(i) on a third nucleic acid molecule. The first, second and third nucleic acid molecule may be AAV vectors.

The nucleic acids described herein may comprise a promoter operably linked to the sequence that encodes the gRNA molecule of (a), e.g., a promoter described herein. The nucleic acid may further comprise a second promoter operably linked to the sequence that encodes the second, third and/or fourth gRNA molecule of (c), e.g., a promoter described herein. The promoter and second promoter differ from one another. In certain embodiments, the promoter and second promoter are the same. The nucleic acids described herein may further comprise a promoter operably linked to the sequence that encodes the Cpf1 molecule of (b), e.g., a promoter described herein.

The presently disclosed subject matter also provides a composition comprising (a) a gRNA molecule as described above. In certain embodiments, the composition further comprises (b) a Cpf1 molecule, e.g., a Cpf1 molecule as described above. In certain embodiments, the composition further comprises (c) a second gRNA molecule as described above. In certain embodiments, the composition is a ribonucleoprotein composition comprising a Cpf1 protein and a ribonucleic acid molecule encoding the gRNA molecule.

The presently disclosed subject matter further provides a method of altering a cell, e.g., altering the structure, e.g., altering the sequence, of a target nucleic acid of a cell, comprising contacting the cell with: (a) a gRNA molecule as described above and (b) a Cpf1 molecule as described above, and optionally, (c) a second gRNA molecule as described above. In another aspect, disclosed herein is a method of treating a subject (e.g., a subject suffering from cancer), e.g., altering the structure, e.g., sequence, of a target nucleic acid of the subject, comprising contacting the subject (or a cell from the subject) with: (a) a gRNA as described above; and (b) a Cpf1 molecule as described above, and optionally, (c) a second gRNA molecule as described above.

In certain embodiments, the method of altering a cell, e.g., altering the structure, e.g., altering the sequence, of a target nucleic acid of a cell, comprising altering two or more T-cell expressed genes selected from the group consisting of FAS, BID, CTLA4, PDCD1, CBLB, PTPN6, B2M, TRAC and TRBC genes.

In certain embodiments, the method of altering a cell comprises altering two or more T-cell expressed genes selected from the group consisting of FAS, BID, CTLA4, PDCD1, CBLB, PTPN6, B2M, TRAC and TRBC genes.

In certain embodiments, the method of altering a cell comprises altering three or more T-cell expressed genes selected from the group consisting of FAS, BID, CTLA4, PDCD1, CBLB, PTPN6, B2M, TRAC and TRBC genes.

In certain embodiments, the method of altering a cell comprises altering four or more T-cell expressed genes selected from the group consisting of FAS, BID, CTLA4, PDCD1, CBLB, PTPN6, B2M, TRAC and TRBC genes.

In certain embodiments, the method of altering a cell comprises altering five or more T-cell expressed genes selected from the group consisting of FAS, BID, CTLA4, PDCD1, CBLB, PTPN6, B2M, TRAC and TRBC genes.

In certain embodiments, the method of altering a cell comprises altering six or more T-cell expressed genes selected from the group consisting of FAS, BID, CTLA4, PDCD1, CBLB, PTPN6, B2M, TRAC and TRBC genes.

In certain embodiments, the method of altering a cell comprises altering seven or more T-cell expressed genes selected from the group consisting of FAS, BID, CTLA4, PDCD1, CBLB, PTPN6, B2M, TRAC and TRBC genes.

In certain embodiments, the method of altering a cell comprises altering each of FAS, BID, CTLA4, PDCD1, CBLB, PTPN6, B2M, TRAC and TRBC genes.

In certain embodiments, the methods comprise contacting a cell from a subject suffering from cancer. In certain embodiments, the cancer is selected from the group consisting of: lymphoma, chronic lymphocytic leukemia (CLL), B cell acute lymphocytic leukemia (B-ALL), acute lymphoblastic leukemia, acute myeloid leukemia, non-Hodgkin's lymphoma (NHL), diffuse large cell lymphoma (DLCL), multiple myeloma, renal cell carcinoma (RCC), neuroblastoma, colorectal cancer, breast cancer, ovarian cancer, melanoma, sarcoma, prostate cancer, lung cancer, esophageal cancer, hepatocellular carcinoma, pancreatic cancer, astrocytoma, mesothelioma, head and neck cancer, and medulloblastoma.

The cell may be from a subject who would benefit from having one or more alteration at one or more T cell target position in one or more T-cell expressed gene.

In certain embodiments, the cell is a T cell. The contacting can be performed ex vivo and the contacted cell can be returned to the subject's body after the contacting step. In certain embodiments, the T cell is an engineered T cell, e.g., an engineered CAR (chimeric antigen receptor) T cell or an engineered TCR (T-cell receptor) T cell. In certain embodiments, the T cell is engineered to express a TCR or a CAR prior to, after, or at the same time as introducing an alteration within a T cell target knockout position of the T-cell expressed gene.

In certain embodiments, the contacting step comprises contacting the cell with a nucleic acid composition as described above. In certain embodiments, the contacting step comprises contacting the cell with a composition as described above. In certain embodiments, the composition is a ribonucleoprotein composition.

In certain embodiments, the contacting comprises contacting the cell with a nucleic acid molecule, e.g., a vector, e.g., an AAV vector, an AAV1 vector, a modified AAV1 vector, an AAV2 vector, a modified AAV2 vector, an AAV3 vector, a modified AAV3 vector, an AAV4 vector, a modified AAV4 vector, an AAV5 vector, a modified AAV5 vector, an AAV6 vector, a modified AAV6 vector, an AAV7 vector, a modified AAV7 vector, an AAV8 vector, an AAV9 vector, an AAV.rh10 vector, a modified AAV.rh10 vector, an AAV.rh32/33 vector, a modified AAV.rh32/33 vector, an AAV.rh43vector, a modified AAV.rh43vector, an AAV.rh64R1vector, or a modified AAV.rh64R1vector.

In certain embodiments, the contacting comprises delivering to the cell a Cpf1 molecule of (b) as a protein or an mRNA, and a nucleic acid molecule which encodes (a) and optionally (c).

In certain embodiments, the contacting comprises delivering to the cell a Cpf1 molecule of (b) as a protein or an mRNA, the gRNA of (a) as an RNA, and optionally the second gRNA of (c), as an RNA.

In certain embodiments, the contacting comprises delivering to the cell the gRNA of (a) as an RNA, optionally the second gRNA of (c) as an RNA, and a nucleic acid composition that encodes the Cpf1 molecule of (b).

The presently disclosed subject matter further provides a reaction mixture comprising a, gRNA molecule as described above, a nucleic acid composition as described above, or a composition as described above, and a cell, e.g., a cell from a subject who would benefit from one or more alteration at one or more T cell target position in the one or more T-cell expressed gene.

The presently disclosed subject matter further provides a kit comprising, (a) a gRNA molecule as described above, or a nucleic acid composition that encodes the gRNA, and one or more of the following: (b) a Cpf1 molecule as described above; (c) a second gRNA molecule as described above.

The presently disclosed subject matter further provides modified gRNA molecules. In certain embodiments, the modified gRNA molecules comprise a modification at or near its 5' end. In certain embodiments, the gRNA molecule comprises a modification at or near its 3' end. In certain embodiments, the gRNA molecule comprises a modification at or near its 5' end and a modification at or near its 3' end. In certain embodiments, the modification is within 1-10, 1-9, 1-8, 1-7, 1-6, 1-5, 1-4, 1-3 or 1-2 nucleotides of its 5' end. In certain embodiments, the modification is within 1-10, 1-9, 1-8, 1-7, 1-6, 1-5, 1-4, 1-3 or 1-2 nucleotides of its 3' end. In certain embodiments, the modification causes the gRNA molecule to exhibit increase stability towards nucleases when introduced into a T cell. In certain embodiments, the modification causes the gRNA molecule to exhibit a reduced innate immune response when introduced into a T cell. In certain embodiments, the innate immune response involves the induction of cytokine expression.

Additionally, the presently disclosed subject matter provides a gRNA molecule as described above for use in treating cancer in a subject. In certain embodiments, the gRNA molecule is used in combination with (b) a Cpf1 molecule.

The presently disclosed subject matter further provides use of a gRNA molecule as described above in the manufacture of a medicament for treating cancer in a subject. In certain embodiments, the medicament further comprises (b) a Cpf1 molecule.

The presently disclosed subject matter further provides a nucleic acid composition as described above for use in treating cancer in a subject.

The presently disclosed subject matter further provides a composition as described above for use in treating cancer in a subject.

The presently disclosed subject matter further provides use of a nucleic acid composition as described above in the manufacture of a medicament for treating cancer in a subject.

The presently disclosed subject matter further provides use of a composition as described above in the manufacture of a medicament for treating cancer in a subject Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In addition, the materials, methods, and examples are illustrative only and not intended to be limiting.

Headings, including numeric and alphabetical headings and subheadings, are for organization and presentation and are not intended to be limiting.

Other features and advantages of the invention will be apparent from the detailed description, drawings, and from the claims.

DETAILED DESCRIPTION

Definitions

Figure 1:
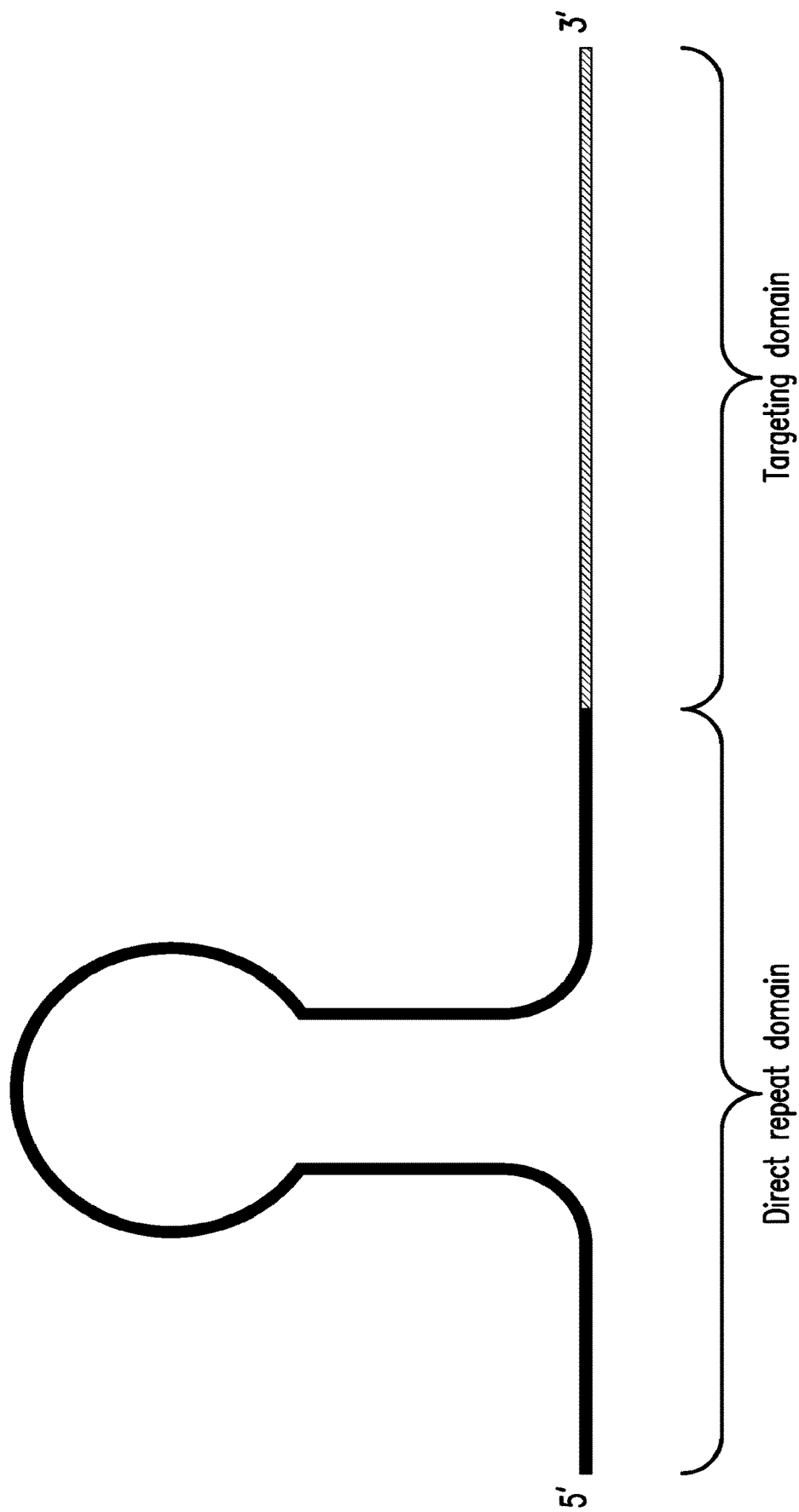
FIG. 1 depicts the structure of a gRNA molecule in accordance with certain non-limiting embodiments of the presently disclosed subject matter.

As used herein, the term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

"Domain", as used herein, is used to describe segments of a protein or nucleic acid. Unless otherwise indicated, a domain is not required to have any specific functional property.

Calculations of homology or sequence identity between two sequences (the terms are used interchangeably herein) are performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). The optimal alignment is determined as the best score using the GAP program in the GCG software package with a Blossum 62 scoring matrix with a gap penalty of 12, a gap extend penalty of 4, and a frame shift gap penalty of 5. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences.

"Inhibitory Cpf1 gRNA molecule", as used herein, refers to a gRNA molecule that comprises a targeting domain that is complementary to a target domain on a nucleic acid that comprises a sequence that encodes a component of the CRISPR/Cpf1 system that is introduced into a cell or subject. An inhibitory Cpf1 gRNA does not target an endogenous cell or subject sequence. In certain embodiments, an inhibitory Cpf1 gRNA molecule comprises a targeting domain that is complementary with a target sequence on: (a) a nucleic acid molecule that encodes a Cpf1 molecule; (b) a nucleic acid molecule that encodes a gRNA which comprises a targeting domain that targets FAS, BID, CTLA4, PDCD1, CBLB, PTPN6, B2M, TRAC and/or TRBC gene (a target gene gRNA); or on more than one nucleic acid molecule that encodes a CRISPR/Cpf1 component, e.g., both (a) and (b). In certain embodiments, a nucleic acid molecule that encodes a CRISPR/Cpf1 component, e.g., that encodes a Cpf1 molecule or a target gene gRNA, comprises more than one target domain that is complementary with an inhibitory Cpf1 gRNA targeting domain. In certain embodiments, an inhibitory Cpf1 gRNA molecule complexes with a Cpf1 molecule and results in Cpf1 mediated inactivation of the targeted nucleic acid molecule, e.g., by cleavage or by binding to the nucleic acid molecule, and results in cessation or reduction of the production of a CRISPR/Cpf1 system component. In certain embodiments, the Cpf1 molecule forms two complexes: a complex comprising a Cpf1 molecule with a target gene gRNA, which complex alters FAS, BID, CTLA4, PDCD1, CBLB, PTPN6, B2M, TRAC and/or TRBC genes; and a complex comprising a Cpf1 molecule with an inhibitory Cpf1 gRNA molecule, which complex acts to prevent further production of a CRISPR/Cpf1 system component, e.g., a Cpf1 molecule or a target gene gRNA molecule. In certain embodiments, an inhibitory Cpf1 gRNA molecule/Cpf1 molecule complex binds to or promotes cleavage of a control region sequence, e.g., a promoter, operably linked to a sequence that encodes a Cpf1 molecule, a sequence that encodes a transcribed region, an exon, or an intron, for the Cpf1 molecule. In certain embodiments, an inhibitory Cpf1 gRNA molecule/Cpf1 molecule complex binds to or promotes cleavage of a control region sequence, e.g., a promoter, operably linked to a gRNA molecule, or a sequence that encodes the gRNA molecule. In certain embodiments, the inhibitory Cpf1 gRNA, e.g., a Cpf1-targeting inhibitory Cpf1 gRNA molecule, or a target gene gRNA-targeting inhibitory Cpf1 gRNA molecule, limits the effect of the Cpf1 molecule/target gene gRNA molecule complex-mediated gene targeting. In certain embodiments, an inhibitory Cpf1 gRNA places temporal, level of expression, or other limits, on activity of the Cpf1 molecule/target gene gRNA molecule complex. In certain embodiments, an inhibitory Cpf1 gRNA reduces off-target or other unwanted activity. In certain embodiments, an inhibitory Cpf1 gRNA molecule inhibits, e.g., entirely or substantially entirely inhibits, the production of a component of the Cpf1 system and thereby limits its activity.

"Modulator", as used herein, refers to an entity, e.g., a drug, which can alter the activity (e.g., enzymatic activity, transcriptional activity, or translational activity), amount, distribution, or structure of a subject molecule or genetic sequence. In certain embodiments, modulation comprises cleavage, e.g., breaking of a covalent or non-covalent bond, or the forming of a covalent or non-covalent bond, e.g., the attachment of a moiety, to the subject molecule. In certain embodiments, a modulator alters the, three dimensional, secondary, tertiary, or quaternary structure, of a subject molecule. A modulator can increase, decrease, initiate, or eliminate a subject activity.

"Large molecule", as used herein, refers to a molecule having a molecular weight of at least 2, 3, 5, 10, 20, 30, 40, 50, 60, 70, 80, 90, or 100 kD. Large molecules include proteins, polypeptides, nucleic acids, biologics, and carbohydrates.

"Polypeptide", as used herein, refers to a polymer of amino acids having less than 100 amino acid residues. In certain embodiments, it has less than 50, 20, or 10 amino acid residues.

"Non-homologous end joining" or "NHEJ", as used herein, refers to ligation mediated repair and/or non-template mediated repair including, e.g., canonical NHEJ (cNHEJ), alternative NHEJ (altNHEJ), microhomology-mediated end joining (MMEJ), and synthesis-dependent microhomology-mediated end joining (SD-MMEJ).

"Reference molecule", e.g., a reference Cpf1 molecule or reference gRNA, as used herein, refers to a molecule to which a subject molecule, e.g., a subject Cpf1 molecule of subject gRNA molecule, e.g., a modified or candidate Cpf1 molecule is compared. For example, a Cpf1 molecule can be characterized as having no more than 10% of the nuclease activity of a reference Cpf1 molecule. Examples of reference Cpf1 molecules include naturally occurring unmodified Cpf1 molecules, e.g., a naturally occurring Cpf1 molecule such as a Cpf1 molecule of *Acidaminococcus* sp. (e.g., strain BV3L6 ("AsCpf1")), or *Lachnospiraceae bacterium* (strain ND2006 ("LbCpf1") or strain MA2020 ("Lb2Cpf1")), as described in Zetsche et al., Cell (2015); 163:759-771. In certain embodiments, the reference Cpf1 molecule is the naturally occurring Cpf1 molecule having the closest sequence identity or homology with the Cpf1 molecule to which it is being compared. In certain embodiments, the reference Cpf1 molecule is a sequence, e.g., a naturally occurring or known sequence, which is the parental form on which a change, e.g., a mutation has been made.

"Replacement", or "replaced", as used herein with reference to a modification of a molecule does not require a process limitation but merely indicates that the replacement entity is present.

"Small molecule", as used herein, refers to a compound having a molecular weight less than about 2 kD, e.g., less than about 2 kD, less than about 1.5 kD, less than about 1 kD, or less than about 0.75 kD.

"Subject", as used herein, may mean either a human or non-human animal. The term includes, but is not limited to, mammals (e.g., humans, other primates, pigs, rodents (e.g., mice and rats or hamsters), rabbits, guinea pigs, cows, horses, cats, dogs, sheep, and goats). In certain embodiments, the subject is a human. In certain embodiments, the subject is poultry.

"Treat", "treating" and "treatment", as used herein, mean the treatment of a disease in a mammal, e.g., in a human, including (a) inhibiting the disease, i.e., arresting or preventing its development; (b) relieving the disease, i.e., causing regression of the disease state; and (c) curing the disease.

"X" as used herein in the context of an amino acid sequence, refers to any amino acid (e.g., any of the twenty natural amino acids) unless otherwise specified.

Improving Cancer Immunotherapy

In an aspect, compositions and methods disclosed herein can be used to affect proliferation of engineered T cells by altering one ore more T cell-expressed genes, e.g., FAS, BID, CTLA4, PDCD1, CBLB, PTPN6, B2M, TRAC and/or TRBC genes. In order for engineered T cells to mount an effective anti-tumor response they need to: 1) proliferate adequately following transfer to the subject to provide a sufficient number of specific tumor-targeting T cells; 2) survive in the subject for a length of time sufficient to maintain the required anti-tumor activity; and 3) evade the influence of suppressive factors produced by immune cells, tumor cells and other cells in the tumor environment so that the engineered T cells maintain a functional anti-tumor phenotype. Insufficient proliferation and/or survival, as well as susceptibility to inhibitory factors, can contribute to lack of efficacy of engineered T cells in subjects suffering from cancer. The methods and compositions disclosed herein address these issues in order to improve efficacy of engineered T cells as a cancer therapeutic modality.

In certain embodiments, compositions and methods disclosed herein can be used to affect proliferation of engineered T cells by altering the CBLB gene. In certain embodiments, reduced or absent expression of Casitas B-lineage lymphoma b protein (encoded by CBLB) reduces the requirement for exogenous interleukin signaling to promote proliferation of engineered T cells following transfer to the subject (Stromnes, I. M. et al., 2010 J. Clin. Invest. 120, 3722-3734).

In certain embodiments, compositions and methods disclosed herein can be used to affect proliferation of engineered T cells by altering the PTPN6 gene. In certain embodiments, reduced or absent expression of Src homology region 2 domain-containing phosphatase-1 protein (encoded by PTPN6) leads to increased short-term accumulation of transferred T cells with subsequently improved anti-tumor activity (Stromnes, I. M. et al., 2012 J. Immunol. 189, 1812-1825).

In certain embodiments, compositions and methods disclosed herein can be used to affect proliferation of engineered T cells by altering the FAS gene. In certain embodiments, reduced or absent expression of the Fas protein will inhibit induction of T cell apoptosis by Fas-ligand; a factor expressed by many cancer types (Dotti, G. et al., 2005 Blood 105, 4677-4684).

In certain embodiments, compositions and methods disclosed herein can be used to affect proliferation of engineered T cells by altering the BID gene. In certain embodiments, reduced or absent expression of the Bid protein prevents the induction of T cell apoptosis following activation of the Fas pathway (Lei, X. Y. et al., 2009 Immunol. Lett. 122, 30-36).

In certain embodiments, compositions and methods disclosed herein can be used to decrease the effect of immune suppressive factors on engineered T cells by altering the CTLA4 gene. In certain embodiments, reduced or absent expression of cytotoxic T-lymphocyte-associated antigen 4 (encoded by CTLA4) abrogates the induction of a non-responsive state ("anergy") following binding of CD80 or CD86 expressed by antigen presenting cells in the tumor environment (Shrikant, P. et al, 1999 Immunity 11, 483-493).

In certain embodiments, compositions and methods disclosed herein can be used to decrease the effect of immune suppressive factors on engineered T cells by altering the PDCD1 gene. In certain embodiments, reduced or absent expression of the Programmed Cell Death Protein 1 (encoded by PDCD1) prevents induction of T cell apoptosis by engagement of PD1 Ligand expressed by tumor cells or cells in the tumor environment (Topalian, S. L. et al., 2012 N. Engl. J. Med. 366, 2443-2454).

In certain embodiments, compositions and methods disclosed herein can be used to improve T cell specificity and safety by altering the TRAC and/or TRBC gene. In certain embodiments, reduced or absent expression of T-cell receptors (encoded by TRAC and TRBC) prevents graft vs. host disease by eliminating T cell receptor recognition of and response to host tissues. This approach, therefore, could be used to generate "off the shelf" T cells (Torikai et al., 2012 Blood 119, 5697-5705). In certain embodiments, reduced or absent expression of the TRAC and/or TRBC gene reduces or eliminates mis-pairing of endogenous T cell receptors with exogenously introduced engineered T cell receptors, thus improving therapeutic efficacy (Provasi et al., 2012, Nature Medicine 18, 807-815).

In certain embodiments, compositions and methods disclosed herein can be used to improve T cell persistence by altering the B2M gene. In certain embodiments, reduced or absent expression of beta-2-microglobulin (encoded by B2M) results in the loss of MHCI surface expression on T cells. Since "foreign" peptides derived from the introduced CAR or engineered TCRs can be presented by class I MHC on the surface of the engineered T cells, in certain embodiments removal of beta-2 microglobulin may reduce the possibility of host rejection of the transfused engineered T cells resulting in hypoimmunogenic cells for adoptive immunotherapy (Mandal et al, Cell Stem Cell, 2014). In certain embodiments, reduced or absent expression of beta-2-microglobulin is used to generate "off-the-shelf" engineered T cells for allotransplantation (Riolobos et al. Mol. Ther., 2013).

In certain embodiments, compositions and methods disclosed herein can be used to decrease one or more gene selected from the group consisting of FAS, BID, CTLA4, PDCD1, CBLB, PTPN6, B2M, TRAC and TRBC genes to improve treatment of cancer immunotherapy using engineered T cells.

Disclosed herein are the approaches to treat cancer via immunotherapy, using the compositions and methods described herein.

In one approach, one or more gene selected from the group consisting of FAS, BID, CTLA4, PDCD1, CBLB, PTPN6, B2M, TRAC and TRBC genes are targeted as a targeted knockout, e.g., to affect T cell proliferation, survival, function, and/or persistence. In certain embodiments, said approach comprises knocking out, one T-cell expressed gene selected from the group consisting of FAS, BID, CTLA4, PDCD1, CBLB, PTPN6, B2M, TRAC and TRBC genes. In certain embodiments, the approach comprises knocking out two T-cell expressed genes selected from the group consisting of FAS, BID, CTLA4, PDCD1, CBLB, PTPN6, B2M, TRAC or TRBC genes. In certain embodiments, the approach comprises knocking out three T-cell expressed genes selected from the group consisting of FAS, BID, CTLA4, PDCD1, CBLB, PTPN6, B2M, TRAC or TRBC genes. In certain embodiments, the approach comprises knocking out four T-cell expressed genes selected from the group consisting of FAS, BID, CTLA4, PDCD1, CBLB, PTPN6, B2M, TRAC or TRBC genes. In certain embodiments, the approach comprises knocking out five T-cell expressed genes selected from the group consisting of FAS, BID, CTLA4, PDCD1, CBLB, PTPN6, B2M, TRAC or TRBC genes. In certain embodiments, the approach comprises knocking out six T-cell expressed genes selected from the group consisting of FAS, BID, CTLA4, PDCD1, CBLB, PTPN6, B2M, TRAC or TRBC genes. In certain embodiments, the approach comprises knocking out seven T-cell expressed genes selected from the group consisting of FAS, BID, CTLA4, PDCD1, CBLB, PTPN6, B2M, TRAC or TRBC genes. In certain embodiments, the approach comprises knocking out eight T-cell expressed genes selected from the group consisting of FAS, BID, CTLA4, PDCD1, CBLB, PTPN6, B2M, TRAC and TRBC genes.

In certain embodiments, the methods comprise initiating treatment of a subject after disease onset. In certain embodiments, the method comprises initiating treatment of a subject well after disease onset, e.g., 1, 2, 3, 4, 5, 6, 7, 8, 9, 10, 12, 24, or 36 months after onset of cancer.

In certain embodiments, the method comprises initiating treatment of a subject in an advanced stage of disease.

Overall, initiation of treatment for subjects at all stages of disease is expected to be of benefit to subjects.

Cancers that may be treated using the compositions and methods disclosed herein include cancers of the blood and solid tumors. For example, cancers that may be treated using the compositions and methods disclosed herein include, but are not limited to, lymphoma, chronic lymphocytic leukemia (CLL), B cell acute lymphocytic leukemia (B-ALL), acute lymphoblastic leukemia, acute myeloid leukemia, non-Hodgkin's lymphoma (NHL), diffuse large cell lymphoma (DELL), multiple myeloma, renal cell carcinoma (RCC), neuroblastoma, colorectal cancer, breast cancer, ovarian cancer, melanoma, sarcoma, prostate cancer, lung cancer, esophageal cancer, hepatocellular carcinoma, pancreatic cancer, astrocytoma, mesothelioma, head and neck cancer, and medulloblastoma.

Methods of Altering One or More T Cell-Expressed Gene

As disclosed herein, one or more T cell-expressed genes, e.g., one or more selected from the group consisting of FAS, BID, CTLA4, PDCD1, CBLB, PTPN6, B2M, TRAC and TRBC genes, can be targeted (e.g., altered) by gene editing, e.g., using CRISPR-Cpf1 mediated methods as described herein.

Methods and compositions disclosed herein, provide for targeting (e.g., altering) a T cell target position in one or more T cell-expressed genes, e.g., one or more selected from the group consisting of FAS, BID, CTLA4, PDCD1, CBLB, PTPN6, B2M, TRAC and TRBC genes. A T cell target position can be targeted (e.g., altered) by gene editing, e.g., using CRISPR-Cpf1 mediated methods to target (e.g. alter) in one or more T cell-expressed genes, e.g., FAS, BID, CTLA4, PDCD1, CBLB, PTPN6, B2M, TRAC and/or TRBC gene.

Disclosed herein are methods for targeting (e.g., altering) a T cell target position in one or more T cell-expressed genes, e.g., FAS, BID, CTLA4, PDCD1, CBLB, PTPN6, B2M, TRAC and/or TRBC gene.

Targeting (e.g., altering) a T cell target position is achieved, e.g., by: knocking out one or more T cell-expressed gene, e.g., FAS, BID, CTLA4, PDCD1, CBLB, PTPN6, B2M, TRAC and/or TRBC gene:

(a) insertion or deletion (e.g., NHEJ-mediated insertion or deletion) of one or more nucleotides in close proximity to or within the coding region (e.g., an early coding region) of one or more T cell-expressed gene, e.g., FAS, BID, CTLA4, PDCD1, CBLB, PTPN6, B2M, TRAC and/or TRBC gene, or (b) deletion (e.g., NHEJ-mediated deletion) of a genomic sequence including at least a portion of one or more T cell-expressed gene, e.g., FAS, BID, CTLA4, PDCD1, CBLB, PTPN6, B2M, TRAC and/or TRBC gene.

All approaches give rise to targeting (e.g., alteration) of one or more T cell-expressed gene, e.g., FAS, BID, CTLA4, PDCD1, CBLB, PTPN6, B2M, TRAC and/or TRBC gene.

In certain embodiments, methods described herein introduce one or more breaks near the coding region in at least one allele of one or more T cell-expressed gene, e.g., FAS, BID, CTLA4, PDCD1, CBLB, PTPN6, B2M, TRAC and/or TRBC gene. In certain embodiments, methods described herein introduce two or more breaks to flank at least a portion of one or more T cell-expressed gene, e.g., FAS, BID, CTLA4, PDCD1, CBLB, PTPN6, B2M, TRAC and/or TRBC gene. The two or more breaks remove (e.g., delete) a genomic sequence including at least a portion of one or more T cell-expressed gene, e.g., FAS, BID, CTLA4, PDCD1, CBLB, PTPN6, B2M, TRAC and/or TRBC gene. All methods described herein result in targeting (e.g., alteration) of one or more T cell-expressed gene, e.g., FAS, BID, CTLA4, PDCD1, CBLB, PTPN6, B2M, TRAC and/or TRBC gene.

The targeting (e.g., alteration) of one or more T cell-expressed gene, e.g., FAS, BID, CTLA4, PDCD1, CBLB, PTPN6, B2M, TRAC and/or TRBC gene, can be mediated by any mechanism. Exemplary mechanisms that can be associated with the alteration of one or more T cell-expressed gene, e.g., FAS, BID, CTLA4, PDCD1, CBLB, PTPN6, B2M, TRAC and/or TRBC gene include, but are not limited to, non-homologous end joining (e.g., classical or alternative), microhomology-mediated end joining (MMEJ), homology-directed repair (e.g., endogenous donor template mediated), and SDSA (synthesis dependent strand annealing).

Knocking Out One or More T Cell-Expressed Gene by Introducing an Insertion or a Deletion In certain embodiments, the method comprises introducing an insertion or deletion of one more nucleotides in close proximity to the T cell target knockout position (e.g., the early coding region) of one or more T cell-expressed gene, e.g., FAS, BID, CTLA4, PDCD1, CBLB, PTPN6, B2M, TRAC and/or TRBC gene. As described herein, in certain embodiments, the method comprises the introduction of one or more breaks (e.g., double strand breaks) to the T cell target knockout position, e.g., the coding region (e.g., the early coding region, e.g., within 500 bp from the start codon or the remaining coding sequence, e.g., downstream of the first 500 bp from the start codon) of one or more T cell-expressed gene, e.g., FAS, BID, CTLA4, PDCD1, CBLB, PTPN6, B2M, TRAC and/or TRBC gene. In certain embodiments, NHEJ-mediated repair of the break(s) allows for the NHEJ-mediated introduction of an indel in close proximity to within the T cell target knockout position.

In certain embodiments, a double strand break is introduced (e.g., positioned by one gRNA molecule) at or in close proximity to a T cell target knockout position in one or more T cell-expressed gene, e.g., FAS, BID, CTLA4, PDCD1, CBLB, PTPN6, B2M, TRAC and/or TRBC gene. In certain embodiments, a single gRNA molecule (e.g., with a Cpf1 nuclease) is used to create a double strand break at or in close proximity to the T cell target knockout position, e.g., the coding region (e.g., the early coding region, e.g., within 500 bp from the start codon or the remaining coding sequence, e.g., downstream of the first 500 bp from the start codon). In certain embodiments, the break is positioned to avoid unwanted target chromosome elements, such as repeat elements, e.g., an Alu repeat.

In certain embodiments, two sets of breaks (e.g., two double strand breaks) are introduced (e.g., positioned by two gRNA molecules) at or in close proximity to a T cell target knockout position in one or more T cell-expressed gene, e.g., FAS, BID, CTLA4, PDCD1, CBLB, PTPN6, B2M, TRAC and/or TRBC gene. In certain embodiments, two gRNA molecules (e.g., with one or two Cpf1 nucleases) are used to create two double strand breaks to flank a T cell target knockout position, e.g., the coding region (e.g., the early coding region, e.g., within 500 bp from the start codon or the remaining coding sequence, e.g., downstream of the first 500 bp from the start codon). In certain embodiments, the gRNAs molecules are configured such that both sets of breaks are positioned upstream or downstream of the T cell target knockout position. In certain embodiments, the gRNA molecules are configured such that one set of break(s) are positioned upstream and a second set of break(s) are positioned downstream of the T cell target knockout position. In certain embodiments, the breaks are positioned to avoid unwanted target chromosome elements, such as repeat elements, e.g., an Alu repeat.

In certain embodiments, two or more (e.g., three or four) gRNA molecules are used with one Cpf1 molecule. In certain embodiments, when two ore more (e.g., three or four) gRNAs are used with two or more Cpf1 molecules, at least one Cpf1 molecule is from a different species than the other Cpf1 molecule(s). For example, when two gRNA molecules are used with two Cpf1 molecules, one Cpf1 molecule can be from one species and the other Cpf1 molecule can be from a different species. Both Cpf1 species are used to generate a double-strand break, as desired.

When more than one gene is targeted for alteration in a cell, the targeted nucleic acids may be altered, e.g., cleaved, by one or more Cpf1 proteins (e.g., Cpf1 nucleases). For example, if two genes are targeted for alteration, e.g., both genes are targeted for knockout, the same or a different Cpf1 protein may be used to target each gene. In certain embodiments, both genes (or each gene targeted in a cell), are cleaved by a Cpf1 nuclease to generate a double stranded break. In certain embodiments, both genes (or each gene targeted in a cell), are cleaved by a Cpf1 nuclease to generate a double stranded break. In certain embodiments, one or more genes in a cell may be altered by cleavage with a Cpf1 nuclease. When two or more Cpf1 proteins are used to cut a target nucleic acid, e.g., different genes in a cell, the Cpf1 proteins may be from different bacterial species. For example, one or more genes in a cell may be altered by cleavage with a Cpf1 protein from one bacterial species, and one or more genes in the same cell may be altered by cleavage with a Cpf1 protein from a different bacterial species. In certain embodiments, when two or more Cpf1 proteins from different species are used that they may be delivered at the same time or delivered sequentially to control specificity of cleavage in the desired gene at the desired position in the target nucleic acid.

In certain embodiments, the targeting domain of the first gRNA molecule and the targeting domain of the second gRNA molecules are complementary to opposite strands of the target nucleic acid molecule. In certain embodiments, the gRNA molecule and the second gRNA molecule are configured such that the PAMs are oriented outward.

Knocking Out One or More T Cell-Expressed Gene by Deleting (e.g., NHEJ-Mediated Deletion) a Genomic Sequence Including at Least a Portion of the One or More T Cell-Expressed Gene In certain embodiments, the method comprises introducing a deletion of a genomic sequence comprising at least a portion of one or more T cell-expressed gene, e.g., FAS, BID, CTLA4, PDCD1, CBLB, PTPN6, B2M, TRAC and/or TRBC gene. As described herein, in certain embodiments, the method comprises introducing two double stand breaks—one 5' and the other 3' to (i.e., flanking) T cell target knockout position. In certain embodiments, two gRNAs, e.g., unimolecular (or chimeric) or modular gRNA molecules, are configured to position the two sets of breaks (e.g., two double strand breaks) on opposite sides of the T cell target knockout position in one or more T cell-expressed gene, e.g., FAS, BID, CTLA4, PDCD1, CBLB, PTPN6, B2M, TRAC and/or TRBC gene.

In certain embodiments, the method comprises deleting (e.g., NHEJ-mediated deletion) a genomic sequence including at least a portion of one or more T cell-expressed gene, e.g., FAS, BID, CTLA4, PDCD1, CBLB, PTPN6, B2M, TRAC and/or TRBC gene. As described herein, in certain embodiments, the method comprises introducing two sets of breaks (e.g., a pair of double strand breaks) to flank a region (e.g., a coding region (e.g., an early coding region), or a non-coding region (e.g., the promoter region, the enhancer region, an intron, the 3'UTR, and/or a polyadenylation signal sequence) in one or more T cell-expressed gene, e.g., FAS, BID, CTLA4, PDCD1, CBLB, PTPN6, B2M, TRAC and/or TRBC gene. In certain embodiments, NHEJ-mediated repair of the break(s) allows for alteration of one or more T cell-expressed gene, e.g., FAS, BID, CTLA4, PDCD1, CBLB, PTPN6, B2M, TRAC and/or TRBC gene as described herein, which reduces or eliminates expression of the gene, e.g., to knock out one or both alleles of the one or more T cell-expressed gene.

In certain embodiments, two sets of breaks (e.g., two double strand breaks) are introduced (e.g., positioned by two gRNA molecules) at or in close proximity to a T cell target knockout position in one or more T cell-expressed gene, e.g., FAS, BID, CTLA4, PDCD1, CBLB, PTPN6, B2M, TRAC and/or TRBC gene. In certain embodiments, two gRNA molecules (e.g., with one or two Cpf1 nucleases) are used to create two sets of breaks to flank a T cell target knockout position, e.g., the gRNA molecules are configured such that one set of break(s) are positioned upstream and a second set of break(s) are positioned downstream of the T cell target knockout position. In certain embodiments, the breaks are positioned to avoid unwanted target chromosome elements, such as repeat elements, e.g., an Alu repeat.

In certain embodiments, two or more (e.g., three or four) gRNA molecules are used with one Cpf1 molecule. In certain embodiments, when two ore more (e.g., three or four) gRNAs are used with two or more Cpf1 molecules, at least one Cpf1 molecule is from a different species than the other Cpf1 molecule(s). For example, when two gRNA molecules are used with two Cpf1 molecules, one Cpf1 molecule can be from one species and the other Cpf1 molecule can be from a different species. Both Cpf1 species are used to generate a double-strand break, as desired.

When more than one gene is targeted for alteration in a cell, the targeted nucleic acids may be altered, e.g., cleaved, by one or more Cpf1 proteins (e.g., Cpf1 nucleases). For example, if two genes are targeted for alteration, e.g., both genes are targeted for knockout, the same or a different Cpf1 protein may be used to target each gene. In certain embodiments, both genes (or each gene targeted in a cell), are cleaved by a Cpf1 nuclease to generate a double stranded break. In certain embodiments, both genes (or each gene targeted in a cell), are cleaved by a Cpf1 nuclease to generate a double stranded break. In certain embodiments, one or more genes in a cell may be altered by cleavage with a Cpf1 nuclease. When two or more Cpf1 proteins are used to cut a target nucleic acid, e.g., different genes in a cell, the Cpf1 proteins may be from different bacterial species. For example, one or more genes in a cell may be altered by cleavage with a Cpf1 protein from one bacterial species, and one or more genes in the same cell may be altered by cleavage with a Cpf1 protein from a different bacterial species. In certain embodiments, when two or more Cpf1 proteins from different species are used, they may be delivered at the same time or delivered sequentially to control specificity of cleavage in the desired gene at the desired position in the target nucleic acid.

In certain embodiments, the targeting domain of the first gRNA molecule and the targeting domain of the second gRNA molecules are complementary to opposite strands of the target nucleic acid molecule. In certain embodiments, the gRNA molecule and the second gRNA molecule are configured such that the PAMs are oriented outward.

In certain embodiments, adoptive transfer of genetically engineered T cells may provide a potential treatment for cancer. Genes encoding cell surface receptors are inserted into the T cells. The genetically engineered T cells are able to detect tumor associated antigens, which can be used to discriminate tumor cells from most normal tissues.

Knockout of one or two alleles of the target gene (e.g., FAS, BID, CTLA4, PDCD1, CBLB, PTPN6, B2M, TRAC or TRBC gene) may be performed after disease onset, but preferably early in the disease course.

I. gRNA Molecules

A gRNA molecule, as that term is used herein, refers to a nucleic acid that promotes the specific targeting or homing of a gRNA molecule/Cpf1 molecule complex to a target nucleic acid. gRNA molecules can be unimodular (having a single RNA molecule, also referred to as "unimolecular", e.g., chimeric gRNAs), or modular (comprising more than one, and typically two, separate RNA molecules). In certain embodiments, the gRNA molecule is a unimodular gRNA.

In certain embodiments, a gRNA molecule comprises, from 5' to 3': a direct repeat domain and a targeting domain, as shown in FIG. 1. In certain embodiments, the gRNA molecule is 15 to 100 (e.g., 15 to 30, 30 to 50, 50 to 70, 70 to 80, or 80 to 100) nucleotides in length. In certain embodiments, the gRNA molecule is 30 to 50 (e.g., 30, 31, 32, 33, 34, 35, 36, 37, 38, 39, 40, 41, 42, 43, 44, 45, 46, 47, 48, 49, or 50) nucleotides in length. In certain embodiments, the gRNA molecule is 38 nucleotides in length. In certain embodiments, the gRNA molecule is 39 nucleotides in length. In certain embodiments, the gRNA molecule is 40 nucleotides in length. In certain embodiments, the gRNA molecule is 41 nucleotides in length. In certain embodiments, the gRNA molecule is 42 nucleotides in length. In certain embodiments, the gRNA molecule is 43 nucleotides in length. In certain embodiments, the gRNA molecule is 44 nucleotides in length. In certain embodiments, the gRNA molecule is 45 nucleotides in length.

The Direct Repeat Domain

In certain embodiments, the direct repeat domain is 10 to 30 (e.g., 10 to 15, 15 to 20, 20 to 25, or 20 to 30) nucleotides in length. In certain embodiments, the direct repeat domain is 15 to 25 (e.g., 15 to 20, or 20 to 25) nucleotides in length. In certain embodiments, the direct repeat domain is 15 to 20 (e.g., 15, 16, 17, 18, 19, or 20) nucleotides in length. In certain embodiments, the direct repeat domain is 20 to 25 (e.g., 20, 21, 22, 23, 24 or 25) nucleotides in length. In certain embodiments, the direct repeat domain is 20 nucleotides in length. In certain embodiments, the direct repeat domain is 21 nucleotides in length.

In certain embodiments, the direct repeat domain comprises a nucleotide sequence set forth in SEQ ID NO: 3708, which is provided below.

[SEQ ID NO: 3708]
UAAUUUCUACUCUUGUAGAU

In certain embodiments, the direct repeat domain comprises a nucleotide sequence set forth in SEQ ID NO: 3709, which is provided below.

[SEQ ID NO: 3709]
UAAUUUCUACUAAGUGUAGAU

In certain embodiments, the direct repeat domain comprises a nucleotide sequence set forth in SEQ ID NO: 3710, which is provided below.

[SEQ ID NO: 3710]
GAAUUUCUACUAUUGUAGAU

A gRNA molecule AsCpf1 comprises a direct repeat domain comprising a nucleotide sequence set forth in SEQ ID NO: 3708.

A gRNA molecule LbCpf1 comprises a direct repeat domain comprising a nucleotide sequence set forth in SEQ ID NO: 3709.

A gRNA molecule Lb2Cpf1 comprises a direct repeat domain comprising a nucleotide sequence set forth in SEQ ID NO: 3710.

In certain embodiments, the direct repeat domain comprises one single stem loop.

In certain embodiments, the direct repeat domain comprises a nucleotide sequence that is at least about 80%, at least about 81%, at least about 82%, at least about 83%, at least about 84%, about 85%, about 86%, about 87%, about 88%, about 89%, about 90%, about 91%, about 92%, about 93%, about 94%, about 95%, about 96%, about 97%, about 98%, or about 99% homologous to the sequence set forth in SEQ ID NO: 3708, SEQ ID NO: 3709, or SEQ ID NO: 3710.

In certain embodiments, the direct repeat domain comprises a nucleotide sequence that comprises at least one modification of the sequence set forth in SEQ ID NO: 3708, SEQ ID NO: 3709, or SEQ ID NO: 3710. The modifications do not substantially or do not interfere or effect the cleavage activity of the gRNA molecule. In certain embodiments, the at least one modification is selected from insertions, deletions, mutations, and combinations thereof. In certain embodiments, the at least one modification is in the stem loop that preserves the RNA duplex. In certain embodiments, the at least one modification comprises at least one mutation. In certain embodiments, the at least one modification does not disrupt the stem loop duplex structure. In certain embodiments, the at least one modification is not within the last three nucleotides of the 3' end of the sequence set forth in SEQ ID NO: 3708, SEQ ID NO: 3709, or SEQ ID NO: 3710. In certain embodiments, the at least one modification is not within the last two nucleotides of the 3' end of the sequence set forth in SEQ ID NO: 3708, SEQ ID NO: 3709, or SEQ ID NO: 3710. In certain embodiments, the at least one modification is not for the last one nucleotide of the 3' end of the sequence set forth in SEQ ID NO: 3708, SEQ ID NO: 3709, or SEQ ID NO: 3710. In certain embodiments, the direct repeat domain comprises or has no more than five modifications, no more than four modifications, no more than three modifications, no more than 2 modifications, or one modification. In certain embodiments, the direct repeat domain comprises or has one, two, three, four, or five modifications.

The Targeting Domain

The targeting domain of a presently disclosed gRNA is complementary to the target domain on the target nucleic acid. In certain embodiments, the targeting domain is complementary to a target nucleic acid in FAS, BID, CTLA4, PDCD1, CBLB, PTPN6, B2M, TRAC or TRBC gene, e.g., a targeting domain having a nucleotide sequence selected from the group consisting of SEQ ID NOS: 1-3707. Guidance on the selection of targeting domains can be found, e.g., in Zetsche et al., Cell (2015); 163:759-771.

In certain embodiments, the targeting domain comprises a nucleotide sequence that is complementary, e.g., at least about 80%, about 85%, about 90%, about 95%, about 98%, or about 99% complementary, e.g., fully complementary, to the target sequence on the target nucleic acid. The targeting domain is part of a RNA molecule and will therefore comprise the base uracil (U), while any DNA encoding the gRNA molecule will comprise the base thymine (T). In certain embodiments, the complementarity of the targeting domain with the target sequence contributes to specificity of the interaction of the gRNA molecule/Cpf1 molecule complex with a target nucleic acid. In certain embodiments, in a targeting domain and target sequence pair, the uracil bases in the targeting domain pair with the adenine bases in the target sequence. In certain embodiments, the targeting domain is 5 to 50 (e.g., 5 to 10, 10 to 20, 20 to 30, 30 to 40, or 40 to 50) nucleotides in length. In certain embodiments, the targeting domain is 15 to 30 (e.g., 15 to 25 or 25 to 30) nucleotides in length. In certain embodiments, the targeting domain is 15 to 25 (e.g., 15, 16, 17, 18, 19, 20, 21, 22, 23, 24 or 25) nucleotides in length.

In certain embodiments, the targeting domain is 18 nucleotides in length. In certain embodiments, the targeting domain is 19 nucleotides in length. In certain embodiments, the targeting domain is 20 nucleotides in length. In certain embodiments, the targeting domain is 21 nucleotides in length. In certain embodiments, the targeting domain is 22 nucleotides in length. In certain embodiments, the targeting domain is 23 nucleotides in length. In certain embodiments, the targeting domain is 24 nucleotides in length.

Typically the targeting domain has full complementarity with the target sequence. In certain embodiments, the target domain has or comprises 1, 2, 3, 4, 5, 6, 7 or 8 nucleotides that are not complementary with the corresponding nucleotide of the targeting domain.

In certain embodiments, the target domain comprises 1, 2, 3, 4 or 5 nucleotides that are complementary with the corresponding nucleotide of the targeting domain within 5 nucleotides of its 5' end. In certain embodiments, the target domain comprises 1, 2, 3, 4 or 5 nucleotides that are complementary with the corresponding nucleotide of the targeting domain within 5 nucleotides of its 3' end.

In certain embodiments, the target domain comprises 1, 2, 3, or 4 nucleotides that are not complementary with the corresponding nucleotide of the targeting domain within 5 nucleotides of its 5' end. In certain embodiments, the target domain comprises 1, 2, 3, or 4 nucleotides that are not complementary with the corresponding nucleotide of the targeting domain within 5 nucleotides of its 3' end.

In certain embodiments, the degree of complementarity, together with other properties of the gRNA, is sufficient to allow targeting of a Cpf1 molecule to the target nucleic acid.

In certain embodiments, the targeting domain comprises two consecutive nucleotides that are not complementary to the target domain ("non-complementary nucleotides"), e.g., two consecutive noncomplementary nucleotides that are within 5 nucleotides of the 5' end of the targeting domain, within 5 nucleotides of the 3' end of the targeting domain, or more than 5 nucleotides away from one or both ends of the targeting domain.

In certain embodiments, no two consecutive nucleotides within 5 nucleotides of the 5' end of the targeting domain, within 5 nucleotides of the 3' end of the targeting domain, or within a region that is more than 5 nucleotides away from one or both ends of the targeting domain, are not complementary to the targeting domain.

In certain embodiments, there are no noncomplementary nucleotides within 5 nucleotides of the 5' end of the targeting domain, within 5 nucleotides of the 3' end of the targeting domain, or within a region that is more than 5 nucleotides away from one or both ends of the targeting domain.

In certain embodiments, the targeting domain comprises a nucleotide sequence selected from the group consisting of SEQ ID NOS: 1-3707.

Any of the targeting domains set forth in SEQ ID NOS: 1-63 can be used with *Acidaminococcus* sp. (e.g., strain BV3L6 ("AsCpf1")), or *Lachnospiraceae bacterium* (strain ND2006 ("LbCpf1") or strain MA2020 ("Lb2Cpf1") Cpf1 to knock out the PDCD1 gene.

Any of the targeting domains set forth in SEQ ID NOS: 64-370 can be used with *Acidaminococcus* sp. (e.g., strain BV3L6 ("AsCpf1")), or *Lachnospiraceae bacterium* (strain ND2006 ("LbCpf1") or strain MA2020 ("Lb2Cpf1") Cpf1 to knock out the CTLA4 gene.

Any of the targeting domains set forth in SEQ ID NOS: 371-503 can be used with *Acidaminococcus* sp. (e.g., strain BV3L6 ("AsCpf1")), or *Lachnospiraceae bacterium* (strain ND2006 ("LbCpf1") or strain MA2020 ("Lb2Cpf1") Cpf1 to knock out the PTPN6 gene.

Any of the targeting domains set forth in SEQ ID NOS: 504-2325 can be used with *Acidaminococcus* sp. (e.g., strain BV3L6 ("AsCpf1")), or *Lachnospiraceae bacterium* (strain ND2006 ("LbCpf1") or strain MA2020 ("Lb2Cpf1") Cpf1 to knock out the CBLB gene.

Any of the targeting domains set forth in SEQ ID NOS: 2326-3094 can be used with *Acidaminococcus* sp. (e.g., strain BV3L6 ("AsCpf1")), or *Lachnospiraceae bacterium* (strain ND2006 ("LbCpf1") or strain MA2020 ("Lb2Cpf1") Cpf1 to knock out the FAS gene.

Any of the targeting domains set forth in SEQ ID NOS: 3095-3283 can be used with *Acidaminococcus* sp. (e.g., strain BV3L6 ("AsCpf1")), or *Lachnospiraceae bacterium* (strain ND2006 ("LbCpf1") or strain MA2020 ("Lb2Cpf1") Cpf1 to knock out the B2M gene.

Any of the targeting domains set forth in SEQ ID NOS: 3284-3385 can be used with *Acidaminococcus* sp. (e.g., strain BV3L6 ("AsCpf1")), or *Lachnospiraceae bacterium* (strain ND2006 ("LbCpf1") or strain MA2020 ("Lb2Cpf1") Cpf1 to knock out the BID gene.

Any of the targeting domains set forth in SEQ ID NOS: 3386-3588 can be used with *Acidaminococcus* sp. (e.g., strain BV3L6 ("AsCpf1")), or *Lachnospiraceae bacterium* (strain ND2006 ("LbCpf1") or strain MA2020 ("Lb2Cpf1") Cpf1 to knock out the TRAC gene.

Any of the targeting domains set forth in SEQ ID NOS: 3589-3707 can be used with *Acidaminococcus* sp. (e.g., strain BV3L6 ("AsCpf1")), or *Lachnospiraceae bacterium* (strain ND2006 ("LbCpf1") or strain MA2020 ("Lb2Cpf1") Cpf1 to knock out the TRBC gene.

In certain embodiments, the targeting domain comprises a nucleotide sequence set forth in SEQ ID NO: 3433, which is provided below.

(SEQ ID NO: 3433)
AGAAUCAAAAUCGGUGAAUAGGC

In certain embodiments, the targeting domain comprises a nucleotide sequence set forth in SEQ ID NO: 3587, which is provided below.

(SEQ ID NO: 3587)
UUUGAGAAUCAAAAUCGGUGAAU

In certain embodiments, the targeting domain comprises a nucleotide sequence set forth in SEQ ID NO: 3538, which is provided below.

(SEQ ID NO: 3538)
GUCUGUGAUAUACACAUCAGAAU

In certain embodiments, the targeting domain comprises a nucleotide sequence set forth in SEQ ID NO:3461, which is provided below.

(SEQ ID NO: 3461)
CACAUGCAAAGUCAGAUUUGUUG

In certain embodiments, the targeting domain comprises a nucleotide sequence set forth in SEQ ID NO:3475, which is provided below.

(SEQ ID NO: 3475)
CAUGUGCAAACGCCUUCAACAAC

In certain embodiments, the targeting domain comprises a nucleotide sequence set forth in SEQ ID NO: 3524, which is provided below.

(SEQ ID NO: 3524)
GAUUCUCAAACAAAUGUGUCACA

In certain embodiments, the targeting domain comprises a nucleotide sequence set forth in SEQ ID NO: 3566, which is provided below.

(SEQ ID NO: 3566)
UCUGUGAUAUACACAUCAGAAUC

In certain embodiments, the targeting domain comprises a nucleotide sequence set forth in SEQ ID NO: 3517, which is provided below.

(SEQ ID NO: 3517)
GAGUCUCUCAGCUGGUACACGGC

In certain embodiments, the targeting domain comprises a nucleotide sequence set forth in SEQ ID NO: 3573, which is provided below.

(SEQ ID NO: 3573)
UGACACAUUUGUUUGAGAAUCAA

In certain embodiments, the targeting domain comprises a nucleotide sequence set forth in SEQ ID NO: 3580, which is provided below.

(SEQ ID NO: 3580)
UUGCUCCAGGCCACAGCACUGUU

In certain embodiments, the targeting domain comprises a nucleotide sequence set forth in SEQ ID NO: 3454, which is provided below.

(SEQ ID NO: 3454)
AUUCUCAAACAAAUGUGUCACAA

In certain embodiments, the targeting domain comprises a nucleotide sequence that is at least about 80%, at least about 81%, at least about 82%, at least about 83%, at least about 84%, about 85%, about 86%, about 87%, about 88%, about 89%, about 90%, about 91%, about 92%, about 93%, about 94%, about 95%, about 96%, about 97%, about 98%, or about 99% homologous to one sequence selected from the group consisting of SEQ ID NOS: 1-3707.

In certain embodiments, the targeting domain comprises a nucleotide sequence that comprises at least one modification of one sequence selected from the group consisting of SEQ ID NOS: 1-3707. In certain embodiments, the modification(s) are one or more modification disclosed in Section VIII. In certain embodiments, at least one modification renders the targeting domain less susceptible to degradation or more bio-compatible, e.g., less immunogenic. By way of example, the backbone of the targeting domain can be modified with a phosphorothioate, or other modification(s) from Section VIII. In certain embodiments, a nucleotide of the targeting domain can comprise a 2' modification, e.g., a 2-acetylation, e.g., a 2' methylation, or other modification(s) from Section VIII.

In certain embodiments, the at least one modification is selected from insertions, deletions, mutations, and combinations thereof. In certain embodiments, the targeting domain comprises 1, 2, 3, 4, 5, 6, 7 or 8 or more modifications. In certain embodiments, the targeting domain comprises 1, 2, 3, or 4 modifications within 5 nucleotides of its 5' end. In certain embodiments, the targeting domain comprises as many as 1, 2, 3, or 4 modifications within 5 nucleotides of its 3' end.

In certain embodiments, the targeting domain comprises modifications at two consecutive nucleotides, e.g., two consecutive nucleotides that are within 5 nucleotides of the 5' end of the targeting domain, within 5 nucleotides of the 3' end of the targeting domain, or more than 5 nucleotides away from one or both ends of the targeting domain.

In certain embodiments, no two consecutive nucleotides are modified within 5 nucleotides of the 5' end of the targeting domain, within 5 nucleotides of the 3' end of the targeting domain, or within a region that is more than 5 nucleotides away from one or both ends of the targeting domain. In certain embodiments, no nucleotide is modified within 5 nucleotides of the 5' end of the targeting domain, within 5 nucleotides of the 3' end of the targeting domain, or within a region that is more than 5 nucleotides away from one or both ends of the targeting domain.

Modifications in the targeting domain can be selected to not interfere with targeting efficacy, which can be evaluated by testing a candidate modification in the system described in Section IV. gRNAs having a candidate targeting domain having a selected length, sequence, degree of complementarity, or degree of modification, can be evaluated in a system in Section IV. The candidate targeting domain can be placed, either alone, or with one or more other candidate changes in a gRNA molecule/Cpf1 molecule system known to be functional with a selected target and evaluated.

In certain embodiments, all of the modified nucleotides are complementary to and capable of hybridizing to corresponding nucleotides present in the target domain. In certain embodiments, 1, 2, 3, 4, 5, 6, 7 or 8 or more modified nucleotides are not complementary to or capable of hybridizing to corresponding nucleotides present in the target domain.

II. Methods for Designing gRNAs

Methods for selecting, designing, and validating targeting domains for use in the gRNAs described herein are provided. Exemplary targeting domains for incorporation into gRNAs are also provided herein.

Methods for selection and validation of target sequences as well as off-target analyses are described, e.g., in Mali et al., 2013 SCIENCE 339(6121): 823-826; Hsu et al. NAT BIOTECHNOL, 31(9): 827-32; Fu et al., 2014 NAT BIOTECHNOL, doi: 10.1038/nbt.2808. PubMed PMID: 24463574; Heigwer et al., 2014 NAT METHODS 11(2):122-3. doi: 10.1038/nmeth.2812. PubMed PMID: 24481216; Bae et al., 2014 BIOINFORMATICS PubMed PMID: 24463181; Xiao A et al., 2014 BIOINFORMATICS PubMed PMID: 24389662; and Zetsche et al., *Cell* (2015); 163:759-771.

In certain embodiments, a software tool can be used to optimize the choice of the targeting domain of a gRNA within a user's target sequence, e.g., to minimize total off-target activity across the genome. Off target activity may be other than cleavage. For example, for each possible targeting domain of a gRNA molecule to be used with a Cpf1 molecule (e.g., AsCpf1, LbCpf1, or Lb2Cpf1), software tools can identify all potential off-target sequences across the genome that contain up to a certain number (e.g., 1, 2, 3, 4, 5, 6, 7, 8, 9, or 10) of mismatched base-pairs. The cleavage efficiency at each off-target sequence can be predicted, e.g., using an experimentally-derived weighting scheme. Other functions, e.g., automated reagent design for gRNA vector construction, primer design for the on-target Surveyor assay, and primer design for high-throughput detection and quantification of off-target cleavage via next-generation sequencing, can also be included in the tool. Candidate gRNA molecules can be evaluated by art-known methods or as described in Section IV.

In certain embodiments, gRNAs for use with a Cpf1 molecule are identified using a DNA sequence searching algorithm, e.g., using a custom gRNA design software based on the public tool cas-offinder (Bae et al. Bioinformatics. 2014; 30(10): 1473-1475). Said custom gRNA design software scores guides after calculating their genome-wide off-target propensity. Typically matches ranging from perfect matches to 7 mismatches are considered for guides ranging in length from 17 to 24. Once the off-target sites were computationally determined, an aggregate score was calculated for each guide and summarized in a tabular output using a web-interface. In addition to identifying potential gRNA sites adjacent to PAM sequences (e.g., a $(T)_xN$ PAM, e.g., a TTTN PAM), the software also identifies all PAM adjacent sequences that differ by 1, 2, 3 or more nucleotides from the selected gRNA sites. Genomic DNA sequence for each gene were obtained from the UCSC Genome browser and sequences were screened for repeat elements using the publicly available RepeatMasker program. RepeatMasker searches input DNA sequences for repeated elements and regions of low complexity. The output is a detailed annotation of the repeats present in a given query sequence.

Following identification, gRNAs were ranked into tiers based on their distance to the target site (based on identification of close matches in the human genome containing a relevant PAM). In certain embodiments, for AsCpf1, LbCpf1 or Lb2Cpf1, the PAM is be a TTTN PAM. The targeting domains for first tier gRNA molecules target within the first 500 bp of coding sequence downstream of start codon in FAS, BID, CTLA4, PDCD1, CBLB, PTPN6, B2M, TRAC or TRBC gene. The targeting domains for second tier gRNA molecules target the rest of the coding sequence of FAS, BID, CTLA4, PDCD1, CBLB, PTPN6, B2M, TRAC or TRBC gene. In certain scenario, when the coding sequence of a gene is shorter than 500 bp, the targeting domains for gRNA molecules were all included in the first tier. Note that tiers are non-inclusive (each gRNA is listed only once for the strategy).

Table 1 provides exemplary targeting domains according to the first design and tiering strategy. As an example, 18-mer, 19-mer, 20-mer, 21-mer, 22-mer, 23-mer or 24-mer targeting domains were designed. Exemplary gRNAs (referred to by SEQ ID NO) designed to be used with a AsCpf1, LbCpf-1 or Lb2Cpf1 molecule identified using this tiered-based approach with respect to knocking out the expression of FAS, BID, CTLA4, PDCD1, CBLB, PTPN6, B2M, TRAC and/or TRBC gene are provided in Table 1. In certain embodiments, the targeting domain hybridizes to the target domain through complementary base pairing. Any of the targeting domains set forth in the SEQ ID NOS: 1-3707 of Table 1 can be used with a AsCpf1, LbCpf1 or Lb2Cpf1 molecule to reduce, decrease or repress the expression of FAS, BID, CTLA4, PDCD1, CBLB, PTPN6, B2M, TRAC and/or TRBC gene.

TABLE 1

SEQ ID NOs of Exemplary gRNAs (AsCpf1, LbCpf1 or Lb2Cpf1)

| Tier | PDCD1 | CTLA4 | PTPN6 | CBLB | FAS | B2M | BID | TRAC | TRBC |
|---|---|---|---|---|---|---|---|---|---|
| 1 | SEQ ID NOS: 1-15 | SEQ ID NOS: 64-167 | SEQ ID NOS: 371-405 | SEQ ID NOS: 504-788 | SEQ ID NOS: 2326-2664 | SEQ ID NOS: 3095-3220 | SEQ ID NOS: 3284-3385 | SEQ ID NOS: 3386-3588 | SEQ ID NOS: 3589-3707 |
| 2 | SEQ ID NOS: 15-63 | SEQ ID NOS: 168-370 | SEQ ID NOS: 406-503 | SEQ ID NOS: 789-2325 | SEQ ID NOS: 2665-3094 | SEQ ID NOS: 3221-3283 | None | None | None |

III. Cpf1 Molecules

Cpf1 molecules of a variety of species can be used in the methods and compositions disclosed herein. In certain embodiments, the Cpf1 molecule is selected from *Acidaminococcus* sp. (e.g., strain BV3L6) molecule ("AsCpf1")), *Lachnospiraceae bacterium* (e.g., strain ND2006) molecule ("LbCpf1"), and *Lachnospiraceae bacterium* (e.g., strain MA2020) molecule ("Lb2Cpf1").

A Cpf1 molecule, or Cpf1 polypeptide, as that term is used herein, refers to a molecule or polypeptide that can interact with a gRNA molecule and, in concert with the gRNA molecule, homes or localizes to a site which comprises a target domain and a PAM sequence. Cpf1 molecule and Cpf1 polypeptide, as those terms are used herein, include naturally occurring Cpf1 molecules and engineered, altered, or modified Cpf1 molecules or Cpf1 polypeptides that differ, e.g., by at least one amino acid residue, from a reference sequence, e.g., the most similar naturally occurring Cpf1 molecule.

The structure has been determined for *Francisella novicida* U112 Cpf1 ("FnCpf1") molecule (Zetsche et al., Cell (2015); 163:759-771). Cpf1 is a single RNA-guided endonuclease lacking a trans-activating crRNA (tracrRNA). See Zetsche (2015), which is incorporated by reference in its entirety. Cpf1 utilizes a short T-rich protospacer-adjacent motif ("PAM") to cleave a target DNA. See id. Cpf1 cleaves DNA via staggered DNA double-stranded break with a 4 or 5-nt 5' overhang. See id. The 5' overhang can facilitate gene insertion via non-homologous end joining (NHEJ) mechanisms. AsCpf1 and LbCpf1 have been shown to exhibit nuclease activity in human cells. See id. A naturally occurring Cpf1 molecule comprises a N-terminal mixed alpha/beta domain, and a C-terminal RuvC-like endonuclease domain ("RuvC domain"). The RuvC domain comprises three split RuvC motifs: RuvC I, RuvCII, and RuvCIII. Different from Cas9, Cpf1 lacks a HNH endonuclease domain. In addition, a naturally occurring Cpf1 molecule comprises a helical region between RuvC I and RuvC II, and a zinc finger-like domain between RuvC II and RuvC III. The structure of a naturally occurring Cpf1 molecule is described in Zetsche (2015).

The RuvC domain retains all of the catalytic residues, e.g., D917, E1006 and D1255 for of FnCpf1. The RuvC domain cleaves both strands of the target DNA, e.g., FAS, BID, CTLA4, PDCD1, CBLB, PTPN6, B2M, TRAC or TRBC, and create a double stranded break.

A presently disclosed Cpf1 molecule or Cpf1 polypeptide interacts with a guide RNA (gRNA) molecule and, in concert with the gRNA molecule, localizes to a site which comprises a target domain and a PAM sequence. In certain embodiments, the ability of a Cpf1 molecule or Cpf1 polypeptide to interact with and cleave a target nucleic acid is PAM sequence dependent. A PAM sequence is a sequence in the target nucleic acid. In certain embodiments, cleavage of the target nucleic acid occurs upstream from the PAM sequence. In certain embodiments, cleavage of the target nucleic acid occurs downstream from the PAM sequence. Cpf1 molecules from different bacterial species can recognize different sequence motifs (e.g., PAM sequences). In certain embodiments, the PAM is a T-rich PAM. In certain embodiments, the PAM has the nucleotide sequence $(T)_xN$, wherein the X is 1-10, and N is A, G, C or T. In certain embodiments, the X is 2, and thus, the PAM is TTN. In certain the X is 3, and thus, the PAM is TTTN. In certain embodiments, a Cpf1 molecule (e.g., AsCpf1, LbCpf1, or Lb2Cpf1) recognizes the sequence motif TTTN and directs cleavage of a target nucleic acid sequence 1-24 (e.g., 1, 2, 3, 4, 5, 6, 7, 8, 9, 10, 11, 12, 13, 14, 15, 16, 17, 18, 19, 20, 21, 22, 23, or 24) by downstream from that sequence. The ability of a Cpf1 molecule to recognize a PAM sequence can be determined by an in vitro selection assay described in Pattanayak et al., NATURE BIOTECHNOLOGY (2013); 31(9):839-843.

In certain embodiments, a Cpf1 molecule or Cpf1 polypeptide comprises an amino acid sequence that:

is at least about 60%, about 65%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% homologous to;

differs at no more than about 2%, about 5%, about 10%, about 15%, about 20%, about 30%, or 40% of the amino acid residues when compared with;

differs by at least 1, 2, 5, 10 or 20 amino acids but by no more than 100, 80, 70, 60, 50, 40 or 30 amino acids from; or is identical to any Cpf1 molecule sequence disclosed herein, or a naturally occurring Cpf1 molecule sequence, e.g., a Cpf1 molecule from a species listed herein or described in Zetsche (2015).

In certain embodiments, the Cpf1 molecule or Cpf1 polypeptide is an engineered Cpf1 molecule or engineered Cpf1 polypeptide that differs from a reference Cpf1 molecule or reference Cpf1 polypeptide. In certain embodiments, the reference Cpf1 molecule or reference Cpf1 polypeptide is a naturally occurring Cpf1 molecule or Cpf1 polypeptide. In certain embodiments, an engineered Cpf1 molecule or engineered Cpf1 polypeptide retains or substantially retains the nuclease (e.g, endonuclease) activity of the reference Cpf1 molecule or reference Cpf1 polypeptide. In certain embodiments, the engineered Cpf1 molecule or engineered Cpf1 polypeptide retains at least about 70%, about 80%, about 90%, about 95%, or about 99% nuclease activity of the reference Cpf1 molecule or reference Cpf1 polypeptide.

One or more mutation or alteration relative to a reference Cpf1 molecule, e.g., a naturally occurring Cpf1 molecule, can be introduced. Such mutation(s) or alteration(s) can comprise substitutions (e.g., conservative substitutions or substitutions of non-essential amino acids); insertions; and/or deletions. As used herein, the term "non-essential" amino acid residue, refers to residue that can be altered from the wild-type sequence of a Cpf1 molecule, e.g., a naturally occurring Cpf1 molecule, without abolishing or without substantially altering a Cpf1 activity (e.g., nuclease/cleavage activity). In certain embodiments, a Cpf1 molecule or Cpf1 polypeptide comprises one or more mutation or alteration, e.g., at least 1, 2, 3, 4, 5, 10, 15, 20, 30, 40 or 50 mutations or alteration but less than 200, 100, or 80 mutations or alteration relative to a reference Cpf1 molecule, e.g., a naturally occurring Cpf1 molecule. The mutation(s) and alteration(s) can be present in the mixed alpha/beta domain, the RuvC domain, or the mixed alpha/beta domain and the RuvC domain.

In certain embodiments, an engineered Cpf1 molecule or engineered Cpf1 polypeptide comprises a cleavage property that differs from a naturally occurring Cpf1 molecules, e.g., that differs from a naturally occurring Cpf1 molecule having the closest homology. For example, a Cpf1 molecule or Cpf1 polypeptide can differ from a naturally occurring Cpf1 molecule, as follows: its ability to modulate, e.g., decreased or increased, cleavage of a double stranded nucleic acid (endonuclease activity), e.g., as compared to a naturally occurring Cpf1 molecule (e.g., AsCpf1, LbCpf-1 or Lb2Cpf1); or the ability to cleave a nucleic acid molecule, e.g., a double stranded nucleic acid molecule, can be eliminated.

In certain embodiments, the engineered Cpf1 molecule or Cpf1 polypeptide is a fusion, e.g., of two of more different Cpf1 molecules or Cpf1 polypeptides, e.g., of two or more naturally occurring Cpf1 molecules of different species. For example, a fragment of a naturally occurring Cpf1 molecule of one species can be fused to a fragment of a Cpf1 molecule of a second species.

Naturally occurring Cpf1 molecules can recognize specific PAM sequences, for example a 5'-TTTN PAM sequence described above for, e.g., AsCpf1, LbCpf-1 and Lb2Cpf1. In certain embodiments, an engineered Cpf1 molecule or engineered Cpf1 polypeptide has altered PAM specificity compared to the reference Cpf1 molecule (e.g., affects PAM recognition). For example, a naturally occurring Cpf1 molecule can be altered, e.g., to alter PAM recognition, e.g., to alter the PAM sequence that the Cpf1 molecule or Cpf1 polypeptide recognizes to decrease off target sites and/or improve specificity; or eliminate a PAM recognition requirement. In certain embodiments, a Cpf1 molecule can be altered, e.g., to increase length of PAM recognition sequence and/or improve Cpf1 specificity to high level of identity, e.g., to decrease off target sites and increase specificity. In certain embodiments, the length of the PAM recognition sequence is at least 4, 5, 6, 7, 8, 9, 10 or 15 amino acids in length.

Cpf1 molecules or Cpf1 polypeptides that recognize different PAM sequences and/or have reduced off-target activity can be generated using directed evolution. Exemplary methods and systems that can be used for directed evolution of Cpf1 molecules are described, e.g., in Esvelt et al. *Nature* 2011, 472(7344): 499-503. Candidate Cpf1 molecules can be evaluated, e.g., by methods described in Section IV.

In certain embodiments, the engineered Cpf1 molecule and engineered Cpf1 polypeptide comprises one or more deletion that reduces the size of the molecule while retaining or substantially retaining (e.g., do not substantially affect or decrease) desired Cpf1 properties, e.g., essentially native conformation, Cpf1 nuclease activity (e.g., endonuclease activity; i.e., the ability to cleave both strands of a double stranded nucleic acid and create a double stranded break), and/or recognition activity of a nucleic acid molecule, e.g., a target nucleic acid or a gRNA. The smaller size of the engineered Cpf1 molecule allows increased flexibility for delivery methods, and thereby increases utility for genome-editing. In certain embodiments, the engineered Cpf1 molecule and engineered Cpf1 polypeptide further comprises one or more linkers, wherein a linker is disposed between the amino acid residues that flank the deletion.

In certain embodiments, a nucleic acid composition encoding a Cpf1 molecule or Cpf1 polypeptide comprises a synthetic nucleic acid sequence. For example, the synthetic nucleic acid sequence can be chemically modified. In certain embodiments, the sequence mRNA has one or more (e.g., all of the following properties: it is capped, polyadenylated, substituted with 5-methylcytidine and/or pseudouridine.

In addition, or alternatively, the synthetic nucleic acid sequence can be codon optimized, e.g., at least one non-common codon or less-common codon has been replaced by a common codon. For example, the synthetic nucleic acid can direct the synthesis of an optimized messenger mRNA, e.g., optimized for expression in a mammalian expression system, e.g., described herein.

In addition, or alternatively, a nucleic acid encoding a sequence molecule or sequence polypeptide can comprise a nuclear localization sequence (NLS). Nuclear localization sequences are known in the art.

An exemplary human codon optimized nucleic acid sequence encoding AsCpf1 is set forth in SEQ ID NO: 3722, which is provided below.

(SEQ ID NO: 3722)
ATGACCCAGTTCGAGGGCTTCACCAACCTGTACCAGGTGAGCAAGACCCT

GCGGTTCGAGCTGATCCCCCAGGGCAAGACCCTGAAGCACATCCAGGAGC

AGGGCTTCATCGAGGAGGACAAGGCCCGGAACGACCACTACAAGGAGCTG

AAGCCCATCATCGACCGGATCTACAAGACCTACGCCGACCAGTGCCTGCA

GCTGGTGCAGCTGGACTGGGAGAACCTGAGCGCCGCCATCGACAGCTACC

GGAAGGAGAAGACCGAGGAGACCCGGAACGCCCTGATCGAGGAGCAGGCC

ACCTACCGGAACGCCATCCACGACTACTTCATCGGCCGGACCGACAACCT

GACCGACGCCATCAACAAGCGGCACGCCGAGATCTACAAGGGCCTGTTCA

AGGCCGAGCTGTTCAACGGCAAGGTGCTGAAGCAGCTGGGCACCGTGACC

ACCACCGAGCACGAGAACGCCCTGCTGCGGAGCTTCGACAAGTTCACCAC

CTACTTCAGCGGCTTCTACGAGAACCGGAAGAACGTGTTCAGCGCCGAGG

ACATCAGCACCGCCATCCCCCACCGGATCGTGCAGGACAACTTCCCCAAG

TTCAAGGAGAACTGCCACATCTTCACCCGGCTGATCACCGCCGTGCCCAG

CCTGCGGGAGCACTTCGAGAACGTGAAGAAGGCCATCGGCATCTTCGTGA

GCACCAGCATCGAGGAGGTGTTCAGCTTCCCCTTCTACAACCAGCTGCTG

ACCCAGACCCAGATCGACCTGTACAACCAGCTGCTGGGCGGCATCAGCCG

GGAGGCCGGCACCGAGAAGATCAAGGGCCTGAACGAGGTGCTGAACCTGG

CCATCCAGAAGAACGACGAGACCGCCCACATCATCGCCAGCCTGCCCCAC

CGGTTCATCCCCCTGTTCAAGCAGATCCTGAGCGACCGGAACACCCTGAG

CTTCATCCTGGAGGAGTTCAAGAGCGACGAGGAGGTGATCCAGAGCTTCT

GCAAGTACAAGACCCTGCTGCGGAACGAGAACGTGCTGGAGACCGCCGAG

GCCCTGTTCAACGAGCTGAACAGCATCGACCTGACCCACATCTTCATCAG

CCACAAGAAGCTGGAGACCATCAGCAGCGCCCTGTGCGACCACTGGGACA

CCCTGCGGAACGCCCTGTACGAGCGGCGGATCAGCGAGCTGACCGGCAAG

ATCACCAAGAGCGCCAAGGAGAAGGTGCAGCGGAGCCTGAAGCACGAGGA

CATCAACCTGCAGGAGATCATCAGCGCCGCCGGCAAGGAGCTGAGCGAGG

CCTTCAAGCAGAAGACCAGCGAGATCCTGAGCCACGCCCACGCCGCCCTG

GACCAGCCCCTGCCCACCACCCTGAAGAAGCAGGAGGAGAAGGAGATCCT

GAAAAGCCAGCTGGACAGCCTGCTGGGCCTGTACCACCTGCTGGACTGGT

TCGCCGTGGACGAGAGCAACGAGGTGGACCCCGAGTTCAGCGCCCGGCTG

ACCGGCATCAAGCTGGAGATGGAGCCCAGCCTGAGCTTCTACAACAAGGC

CCGGAACTACGCCACCAAGAAGCCCTACAGCGTGGAGAAGTTCAAGCTGA

ACTTCCAGATGCCCACCCTGGCCAGCGGCTGGGACGTGAACAAGGAGAAG

AACAACGGCGCCATCCTGTTCGTGAAGAACGGCCTGTACTACCTGGGCAT

CATGCCCAAGCAGAAGGGCCGGTACAAGGCCCTGAGCTTCGAGCCCACCG

-continued
```
AGAAGACCAGCGAGGGCTTCGACAAGATGTACTACGACTACTTCCCCGAC
GCCGCCAAGATGATCCCCAAGTGCAGCACCCAGCTGAAGGCCGTGACCGC
CCACTTCCAGACCCACACCACCCCCATCCTGCTGAGCAACAACTTCATCG
AGCCCCTGGAGATCACCAAGGAGATCTACGACCTGAACAACCCCGAGAAG
GAGCCCAAGAAGTTCCAGACCGCCTACGCCAAGAAGACCGGCGACCAGAA
GGGCTACCGGGAGGCCCTGTGCAAGTGGATCGACTTCACCCGGGACTTCC
TGAGCAAGTACACCAAGACCACCAGCATCGACCTGAGCAGCCTGCGGCCC
AGCAGCCAGTACAAGGACCTGGGCGAGTACTACGCCGAGCTGAACCCCCT
GCTGTACCACATCAGCTTCCAGCGGATCGCCGAGAAGGAGATCATGGACG
CCGTGGAGACCGGCAAGCTGTACCTGTTCCAGATCTACAACAAGGACTTC
GCCAAGGGCCACCACGGCAAGCCCAACCTGCACACCCTGTACTGGACCGG
CCTGTTCAGCCCCGAGAACCTGGCCAAGACCAGCATCAAGCTGAACGGCC
AGGCCGAGCTGTTCTACCGGCCCAAGAGCCGGATGAAGCGGATGGCCCAC
CGGCTGGGCGAGAAGATGCTGAACAAGAAGCTGAAGGACCAGAAGACCCC
CATCCCCGACACCCTGTACCAGGAGCTGTACGACTACGTGAACCACCGGC
TGAGCCACGACCTGAGCGACGAGGCCCGGGCCCTGCTGCCCAACGTGATC
ACCAAGGAGGTGAGCCACGAGATCATCAAGGACCGGCGGTTCACCAGCGA
CAAGTTCTTCTTCCACGTGCCCATCACCCTGAACTACCAGGCCGCCAACA
GCCCCAGCAAGTTCAACCAGCGGGTGAACGCCTACCTGAAGGAGCACCCC
GAGACCCCCATCATCGGCATCGACCGGGGCGAGCGGAACCTGATCTACAT
CACCGTGATCGACAGCACCGGCAAGATCCTGGAGCAGCGGAGCCTGAACA
CCATCCAGCAGTTCGACTACCAGAAGAAGCTGGACAACCGGGAGAAGGAG
CGGGTGGCCGCCCGGCAGGCCTGGAGCGTGGTGGGCACCATCAAGGACCT
GAAGCAGGGCTACCTGAGCCAGGTGATCCACGAGATCGTGGACCTGATGA
TCCACTACCAGGCCGTGGTGGTGCTGGAGAACCTGAACTTCGGCTTCAAG
AGCAAGCGGACCGGCATCGCCGAGAAGGCCGTGTACCAGCAGTTCGAGAA
GATGCTGATCGACAAGCTGAACTGCCTGGTGCTGAAGGACTACCCCGCCG
AGAAGGTGGGCGGCGTGCTGAACCCCTACCAGCTGACCGACCAGTTCACC
AGCTTCGCCAAGATGGGCACCCAGAGCGGCTTCCTGTTCTACGTGCCCGC
CCCCTACACCAGCAAGATCGACCCCCTGACCGGCTTCGTGGACCCCTTCG
TGTGGAAGACCATCAAGAACCACGAGAGCCGGAAGCACTTCCTGGAGGGC
TTCGACTTCCTGCACTACGACGTGAAGACCGGCGACTTCATCCTGCACTT
CAAGATGAACCGGAACCTGAGCTTCCAGCGGGGCCTGCCCGGCTTCATGC
CCGCCTGGGACATCGTGTTCGAGAAGAACGAGACCCAGTTCGACGCCAAG
GGCACCCCCTTCATCGCCGGCAAGCGGATCGTGCCCGTGATCGAGAACCA
CCGGTTCACCGGCCGGTACCGGGACCTGTACCCCGCCAACGAGCTGATCG
CCCTGCTGGAGGAGAAGGGCATCGTGTTCCGGGACGGCAGCAACATCCTG
CCCAAGCTGCTGGAGAACGACGACAGCCACGCCATCGACACCATGGTGGC
CCTGATCCGGAGCGTGCTGCAGATGCGGAACAGCAACGCCGCCACCGGCG
AGGACTACATCAACAGCCCCGTGCGGGACCTGAACGGCGTGTGCTTCGAC
AGCCGGTTCCAGAACCCCGAGTGGCCCATGGACGCCGACGCCAACGGCGC
```

-continued
```
CTACCACATCGCCCTGAAGGGCCAGCTGCTGCTGAACCACCTGAAGGAGA
GCAAGGACCTGAAGCTGCAGAACGGCATCAGCAACCAGGACTGGCTGGCC
TACATCCAGGAGCTGCGGAACAAGCGGCCCGCCGCCACCAAGAAGGCCGG
CCAGGCCAAGAAGAAGAAGGGCAGCTACCCCTACGACGTGCCCGACTACG
CCTACCCCTACGACGTGCCCGACTACGCCTACCCCTACGACGTGCCCGAC
TACGCCTGA
```

The corresponding amino acid sequence encoded by the nucleotide sequence set forth in SEQ ID NO: 3722 is set forth in SEQ ID NO: 3725, which is provided below.

```
                                  (SEQ ID NO: 3725)
MTQFEGFTNLYQVSKTLRFELIPQGKTLKHIQEQGFIEEDKARNDHYKEL
KPIIDRIYKTYADQCLQLVQLDWENLSAAIDSYRKEKTEETRNALIEEQA
TYRNAIHDYFIGRTDNLTDAINKRHAEIYKGLFKAELFNGKVLKQLGTVT
TTEHENALLRSFDKFTTYFSGFYENRKNVFSAEDISTAIPHRIVQDNFPK
FKENCHIFTRLITAVPSLREHFENVKKAIGIFVSTSIEEVFSFPFYNQLL
TQTQIDLYNQLLGGISREAGTEKIKGLNEVLNLAIQKNDETAHIIASLPH
RFIPLFKQILSDRNTLSFILEEFKSDEEVIQSFCKYKTLLRNENVLETAE
ALFNELNSIDLTHIFISHKKLETISSALCDHWDTLRNALYERRISELTGK
ITKSAKEKVQRSLKHEDINLQEIISAAGKELSEAFKQKTSEILSHAHAAL
DQPLPTTLKKQEEKEILKSQLDSLLGLYHLLDWFAVDESNEVDPEFSARL
TGIKLEMEPSLSFYNKARNYATKKPYSVEKFKLNFQMPTLASGWDVNKEK
NNGAILFVKNGLYYLGIMPKQKGRYKALSFEPTEKTSEGFDKMYYDYFPD
AAKMIPKCSTQLKAVTAHFQTHTTPILLSNNFIEPLEITKEIYDLNNPEK
EPKKFQTAYAKKTGDQKGYREALCKWIDFTRDFLSKYTKTTSIDLSSLRP
SSQYKDLGEYYAELNPLLYHISFQRIAEKEIMDAVETGKLYLFQIYNKDF
AKGHHGKPNLHTLYWTGLFSPENLAKTSIKLNGQAELFYRPKSRMKRMAH
RLGEKMLNKKLKDQKTPIPDTLYQELYDYVNHRLSHDLSDEARALLPNVI
TKEVSHEIIKDRRFTSDKFFFHVPITLNYQAANSPSKFNQRVNAYLKEHP
ETPIIGIDRGERNLIYITVIDSTGKILEQRSLNTIQQFDYQKKLDNREKE
RVAARQAWSVVGTIKDLKQGYLSQVIHEIVDLMIHYQAVVVLENLNFGFK
SKRTGIAEKAVYQQFEKMLIDKLNCLVLKDYPAEKVGGVLNPYQLTDQFT
SFAKMGTQSGFLFYVPAPYTSKIDPLTGFVDPFVWKTIKNHESRKHFLEG
FDFLHYDVKTGDFILHFKMNRNLSFQRGLPGFMPAWDIVFEKNETQFDAK
GTPFIAGKRIVPVIENHRFTGRYRDLYPANELIALLEEKGIVFRDGSNIL
PKLLENDDSHAIDTMVALIRSVLQMRNSNAATGEDYINSPVRDLNGVCFD
SRFQNPEWPMDADANGAYHIALKGQLLLNHLKESKDLKLQNGISNQDWLA
YIQELRN
```

An exemplary human codon optimized nucleic acid sequence encoding LbCpf1 is set forth in SEQ ID NO: 3723, which is provided below.

(SEQ ID NO: 3723)
ATGAGCAAGCTGGAGAAGTTCACCAACTGCTACAGCCTGAGCAAGACCCT
GCGGTTCAAGGCCATCCCCGTGGGCAAGACCCAGGAGAACATCGACAACA
AGCGGCTGCTGGTGGAGGACGAGAAGCGGGCCGAGGACTACAAGGGCGTG
AAGAAGCTGCTGGACCGGTACTACCTGAGCTTCATCAACGACGTGCTGCA
CAGCATCAAGCTGAAGAACCTGAACAACTACATCAGCCTGTTCCGGAAGA
AGACCCGGACCGAGAAGGAGAACAAGGAGCTGGAGAACCTGGAGATCAAC
CTGCGGAAGGAGATCGCCAAGGCCTTCAAGGGCAACGAGGGCTACAAGAG
CCTGTTCAAGAAGGACATCATCGAGACCATCCTGCCCGAGTTCCTGGACG
ACAAGGACGAGATCGCCCTGGTGAACAGCTTCAACGGCTTCACCACCGCC
TTCACCGGCTTCTTCGACAACCGGGAGAACATGTTCAGCGAGGAGGCCAA
GAGCACCAGCATCGCCTTCCGGTGCATCAACGAGAACCTGACCCGGTACA
TCAGCAACATGGACATCTTCGAGAAGGTGGACGCCATCTTCGACAAGCAC
GAGGTGCAGGAGATCAAGGAGAAGATCCTGAACAGCGACTACGACGTGGA
GGACTTCTTCGAGGGCGAGTTCTTCAACTTCGTGCTGACCCAGGAGGGCA
TCGACGTGTACAACGCCATCATCGGCGGCTTCGTGACCGAGAGCGGCGAG
AAGATCAAGGGCCTGAACGAGTACATCAACCTGTACAACCAGAAGACCAA
GCAGAAGCTGCCCAAGTTCAAGCCCCTGTACAAGCAGGTGCTGAGCGACC
GGGAGAGCCTGAGCTTCTACGGCGAGGGCTACACCAGCGACGAGGAGGTG
CTGGAGGTGTTCCGGAACACCCTGAACAAGAACAGCGAGATCTTCAGCAG
CATCAAGAAGCTGGAGAAGCTGTTCAAGAACTTCGACGAGTACAGCAGCG
CCGGCATCTTCGTGAAGAACGGCCCCGCCATCAGCACCATCAGCAAGGAC
ATCTTCGGCGAGTGGAACGTGATCCGGGACAAGTGGAACGCCGAGTACGA
CGACATCCACCTGAAGAAGAAGGCCGTGGTGACCGAGAAGTACGAGGACG
ACCGGCGGAAAAGCTTCAAGAAGATCGGCAGCTTCAGCCTGGAGCAGCTG
CAGGAGTACGCCGACGCCGACCTGAGCGTGGTGGAGAAGCTGAAGGAGAT
CATCATCCAGAAGGTGGACGAGATCTACAAGGTGTACGGCAGCAGCGAGA
AGCTGTTCGACGCCGACTTCGTGCTGGAGAAAAGCCTGAAGAAGAACGAC
GCCGTGGTGGCCATCATGAAGGACCTGCTGGACAGCGTGAAAAGCTTCGA
GAACTACATCAAGGCCTTCTTCGGCGAGGGCAAGGAGACCAACCGGGACG
AGAGCTTCTACGGCGACTTCGTGCTGGCCTACGACATCCTGCTGAAGGTG
GACCACATCTACGACGCCATCCGGAACTACGTGACCCAGAAGCCCTACAG
CAAGGACAAGTTCAAGCTGTACTTCCAGAACCCCCAGTTCATGGGCGGCT
GGGACAAGGACAAGGAGACCGACTACCGGGCCACCATCCTGCGGTACGGC
AGCAAGTACTACCTGGCCATCATGGACAAGAAGTACGCCAAGTGCCTGCA
GAAGATCGACAAGGACGACGTGAACGGCAACTACGAGAAGATCAACTACA
AGCTGCTGCCCGGCCCCAACAAGATGCTGCCCAAGGTGTTCTTCAGCAAG
AAGTGGATGGCCTACTACAACCCCAGCGAGGACATCCAGAAGATCTACAA
GAACGGCACCTTCAAGAAGGGCGACATGTTCAACCTGAACGACTGCCACA
AGCTGATCGACTTCTTCAAGGACAGCATCAGCCGGTACCCCAAGTGGAGC
AACGCCTACGACTTCAACTTCAGCGAGACCGAGAAGTACAAGGACATCGC
CGGCTTCTACCGGGAGGTGGAGGAGCAGGGCTACAAGGTGAGCTTCGAGA
GCGCCAGCAAGAAGGAGGTGGACAAGCTGGTGGAGGAGGGCAAGCTGTAC
ATGTTCCAGATCTACAACAAGGACTTCAGCGACAAGAGCCACGGCACCCC
CAACCTGCACACCATGTACTTCAAGCTGCTGTTCGACGAGAACAACCACG
GCCAGATCCGGCTGAGCGGCGGCGCCGAGCTGTTCATGCGGCGGGCCAGC
CTGAAGAAGGAGGAGCTGGTGGTGCACCCCGCCAACAGCCCCATCGCCAA
CAAGAACCCCGACAACCCCAAGAAGACCACCACCCTGAGCTACGACGTGT
ACAAGGACAAGCGGTTCAGCGAGGACCAGTACGAGCTGCACATCCCCATC
GCCATCAACAAGTGCCCCAAGAACATCTTCAAGATCAACACCGAGGTGCG
GGTGCTGCTGAAGCACGACGACAACCCCTACGTGATCGGCATCGACCGGG
GCGAGCGGAACCTGCTGTACATCGTGGTGGTGGACGGCAAGGGCAACATC
GTGGAGCAGTACAGCCTGAACGAGATCATCAACAACTTCAACGGCATCCG
GATCAAGACCGACTACCACAGCCTGCTGGACAAGAAGGAGAAGGAGCGGT
TCGAGGCCCGGCAGAACTGGACCAGCATCGAGAACATCAAGGAGCTGAAG
GCCGGCTACATCAGCCAGGTGGTGCACAAGATCTGCGAGCTGGTGGAGAA
GTACGACGCCGTGATCGCCCTGGAGGACCTGAACAGCGGCTTCAAGAACA
GCCGGGTGAAGGTGGAGAAGCAGGTGTACCAGAAGTTCGAGAAGATGCTG
ATCGACAAGCTGAACTACATGGTGGACAAGAAAAGCAACCCCTGCGCCAC
CGGCGGCGCCCTGAAGGGCTACCAGATCACCAACAAGTTCGAGAGCTTCA
AGAGCATGAGCACCCAGAACGGCTTCATCTTCTACATCCCCGCCTGGCTG
ACCAGCAAGATCGACCCCAGCACCGGCTTCGTGAACCTGCTGAAGACCAA
GTACACCAGCATCGCCGACAGCAAGAAGTTCATCAGCAGCTTCGACCGGA
TCATGTACGTGCCCGAGGAGGACCTGTTCGAGTTCGCCCTGGACTACAAG
AACTTCAGCCGGACCGACGCCGACTACATCAAGAAGTGGAAGCTGTACAG
CTACGGCAACCGGATCCGGATCTTCCGGAACCCCAAGAAGAACAACGTGT
TCGACTGGGAGGAGGTGTGCCTGACCAGCGCCTACAAGGAGCTGTTCAAC
AAGTACGGCATCAACTACCAGCAGGGCGACATCCGGGCCCTGCTGTGCGA
GCAGAGCGACAAGGCCTTCTACAGCAGCTTCATGGCCCTGATGAGCCTGA
TGCTGCAGATGCGGAACAGCATCACCGGCCGGACCGACGTGGACTTCCTG
ATCAGCCCCGTGAAGAACAGCGACGGCATCTTCTACGACAGCCGGAACTA
CGAGGCCCAGGAGAACGCCATCCTGCCCAAGAACGCCGACGCCAACGGCG
CCTACAACATCGCCCGGAAGGTGCTGTGGGCCATCGGCCAGTTCAAGAAG
GCCGAGGACGAGAAGCTGGACAAGGTGAAGATCGCCATCAGCAACAAGGA
GTGGCTGGAGTACGCCCAGACCAGCGTGAAGCACAAGCGGCCCGCCGCCA
CCAAGAAGGCCGGCCAGGCCAAGAAGAAGAAGGGCAGCTACCCCTACGAC
GTGCCCGACTACGCCTACCCCTACGACGTGCCCGACTACGCCTACCCCTA
CGACGTGCCCGACTACGCCTGA

The corresponding amino acid sequence encoded by the nucleotide sequence set forth in SEQ ID NO: 3723 is set forth in SEQ ID NO: 3726, which is provided below.

(SEQ ID NO: 3726)
MSKLEKFTNCYSLSKTLRFKAIPVGKTQENIDNKRLLVEDEKRAEDYKGV
KKLLDRYYLSFINDVLHSIKLKNLNNYISLFRKKTRTEKENKELENLEIN
LRKEIAKAFKGNEGYKSLFKKDIIETILPEFLDDKDEIALVNSFNGFTTA
FTGFFDNRENMFSEEAKSTSIAFRCINENLTRYISNMDIFEKVDAIFDKH
EVQEIKEKILNSDYDVEDFFEGEFFNFVLTQEGIDVYNAIIGGFVTESGE
KIKGLNEYINLYNQKTKQKLPKFKPLYKQVLSDRESLSFYGEGYTSDEEV
LEVFRNTLNKNSEIFSSIKKLEKLFKNFDEYSSAGIFVKNGPAISTISKD
IFGEWNVIRDKWNAEYDDIHLKKKAVVTEKYEDDRRKSFKKIGSFSLEQL
QEYADADLSVVEKLKEIIQKVDEIYKVYGSSEKLFDADFVLEKSLKKND
AVVAIMKDLLDSVKSFENYIKAFFGEGKETNRDESFYGDFVLAYDILLKV
DHIYDAIRNYVTQKPYSKDKFKLYFQNPQFMGGWDKDKETDYRATILRYG
SKYYLAIMDKKYAKCLQKIDKDDVNGNYEKINYKLLPGPNKMLPKVFFSK
KWMAYYNPSEDIQKIYKNGTFKKGDMFNLNDCHKLIDFFKDSISRYPKWS
NAYDFNFSETEKYKDIAGFYREVEEQGYKVSFESASKKEVDKLVEEGKLY
MFQIYNKDFSDKSHGTPNLHTMYFKLLFDENNHGQIRLSGGAELFMRRAS
LKKEELVVHPANSPIANKNPDNPKKTTTLSYDVYKDKRFSEDQYELHIPI
AINKCPKNIFKINTEVRVLLKHDDNPYVIGIDRGERNLLYIVVVDGKGNI
VEQYSLNEIINNFNGIRIKTDYHSLLDKKEKERFEARQNWTSIENIKELK
AGYISQVVHKICELVEKYDAVIALEDLNSGFKNSRVKVEKQVYQKFEKML
IDKLNYMVDKKSNPCATGGALKGYQITNKFESFKSMSTQNGFIFYIPAWL
TSKIDPSTGFVNLLKTKYTSIADSKKFISSFDRIMYVPEEDLFEFALDYK
NFSRTDADYIKKWKLYSYGNRIRIFRNPKKNNVFDWEEVCLTSAYKELFN
KYGINYQQGDIRALLCEQSDKAFYSSFMALMSLMLQMRNSITGRTDVDFL
ISPVKNSDGIFYDSRNYEAQENAILPKNADANGAYNIARKVLWAIGQFKK
AEDEKLDKVKIAISNKEWLEYAQTSVKH

An exemplary human codon optimized nucleic acid sequence encoding Lb2Cpf1 is set forth in SEQ ID NO: 3724, which is provided below.

(SEQ ID NO: 3724)
ATGTACTACGAGAGCCTGACCAAGCAGTACCCCGTGAGCAAGACCATCCG
GAACGAGCTGATCCCCATCGGCAAGACCCTGGACAACATCCGGCAGAACA
ACATCCTGGAGAGCGACGTGAAGCGGAAGCAGAACTACGAGCACGTGAAG
GGCATCCTGGACGAGTACCACAAGCAGCTGATCAACGAGGCCCTGGACAA
CTGCACCCTGCCCAGCCTGAAGATCGCCGCCGAGATCTACCTGAAGAACC
AGAAGGAGGTGAGCGACCGGGAGGACTTCAACAAGACCCAGGACCTGCTG
CGGAAGGAGGTGGTGGAGAAGCTGAAGGCCCACGAGAACTTCACCAAGAT
CGGCAAGAAGGACATCCTGGACCTGCTGGAGAAGCTGCCCAGCATCAGCG
AGGACGACTACAACGCCCTGGAGAGCTTCCGGAACTTCTACACCTACTTC
ACCAGCTACAACAAGGTGCGGGAGAACCTGTACAGCGACAAGGAGAAAAG
CAGCACCGTGGCCTACCGGCTGATCAACGAGAACTTCCCCAAGTTCCTGG
ACAACGTGAAAAGCTACCGGTTCGTGAAGACCGCCGGCATCCTGGCCGAC
GGCCTGGGCGAGGAGGAGCAGGACAGCCTGTTCATCGTGGAGACCTTCAA
CAAGACCCTGACCCAGGACGGCATCGACACCTACAACAGCCAGGTGGGCA
AGATCAACAGCAGCATCAACCTGTACAACCAGAAGAACCAGAAGGCCAAC
GGCTTCCGGAAGATCCCCAAGATGAAGATGCTGTACAAGCAGATCCTGAG
CGACCGGGAGGAGAGCTTCATCGACGAGTTCCAGAGCGACGAGGTGCTGA
TCGACAACGTGGAGAGCTACGGCAGCGTGCTGATCGAGAGCCTGAAAAGC
AGCAAGGTGAGCGCCTTCTTCGACGCCCTGCGGGAGAGCAAGGGCAAGAA
CGTGTACGTGAAGAACGACCTGGCCAAGACCGCCATGAGCAACATCGTGT
TCGAGAACTGGCGGACCTTCGACGACCTGCTGAACCAGGAGTACGACCTG
GCCAACGAGAACAAGAAGAAGGACGACAAGTACTTCGAGAAGCGGCAGAA
GGAGCTGAAGAAGAACAAGAGCTACAGCCTGGAGCACCTGTGCAACCTGA
GCGAGGACAGCTGCAACCTGATCGAGAACTACATCCACCAGATCAGCGAC
GACATCGAGAACATCATCATCAACAACGAGACCTTCCTGCGGATCGTGAT
CAACGAGCACGACCGGAGCCGGAAGCTGGCCAAGAACCGGAAGGCCGTGA
AGGCCATCAAGGACTTCCTGGACAGCATCAAGGTGCTGGAGCGGGAGCTG
AAGCTGATCAACAGCAGCGGCCAGGAGCTGGAGAAGGACCTGATCGTGTA
CAGCGCCCACGAGGAGCTGCTGGTGGAGCTGAAGCAGGTGGACAGCCTGT
ACAACATGACCCGGAACTACCTGACCAAGAAGCCCTTCAGCACCGAGAAG
GTGAAGCTGAACTTCAACCGGAGCACCCTGCTGAACGGCTGGGACCGGAA
CAAGGAGACCGACAACCTGGGCGTGCTGCTGCTGAAGGACGGCAAGTACT
ACCTGGGCATCATGAACACCAGCGCCAACAAGGCCTTCGTGAACCCCCCC
GTGGCCAAGACCGAGAAGGTGTTCAAGAAGGTGGACTACAAGCTGCTGCC
CGTGCCCAACCAGATGCTGCCCAAGGTGTTCTTCGCCAAGAGCAACATCG
ACTTCTACAACCCCAGCAGCGAGATCTACAGCAACTACAAGAAGGGCACC
CACAAGAAGGGCAACATGTTCAGCCTGGAGGACTGCCACAACCTGATCGA
CTTCTTCAAGGAGAGCATCAGCAAGCACGAGGACTGGAGCAAGTTCGGCT
TCAAGTTCAGCGACACCGCCAGCTACAACGACATCAGCGAGTTCTACCGG
GAGGTGGAGAAGCAGGGCTACAAGCTGACCTACACCGACATCGACGAGAC
CTACATCAACGACCTGATCGAGCGGAACGAGCTGTACCTGTTCCAGATCT
ACAACAAGGACTTCAGCATGTACAGCAAGGGCAAGCTGAACCTGCACACC
CTGTACTTCATGATGCTGTTCGACCAGCGGAACATCGACGACGTGGTGTA
CAAGCTGAACGGCGAGGCCGAGGTGTTCTACCGGCCCGCCAGCATCAGCG
AGGACGAGCTGATCATCCACAAGGCCGGCGAGGAGATCAAGAACAAGAAC
CCCAACCGGGCCCGGACCAAGGAGACCAGCACCTTCAGCTACGACATCGT
GAAGGACAAGCGGTACAGCAAGGACAAGTTCACCCTGCACATCCCCATCA
CCATGAACTTCGGCGTGGACGAGGTGAAGCGGTTCAACGACGCCGTGAAC
AGCGCCATCCGGATCGACGAGAACGTGAACGTGATCGGCATCGACCGGGG
CGAGCGGAACCTGCTGTACGTGGTGGTGATCGACAGCAAGGGCAACATCC

```
TGGAGCAGATCAGCCTGAACAGCATCATCAACAAGGAGTACGACATCGAG

ACCGACTACCACGCCCTGCTGGACGAGCGGGAGGGCGGCCGGGACAAGGC

CCGGAAGGACTGGAACACCGTGGAGAACATCCGGGACCTGAAGGCCGGCT

ACCTGAGCCAGGTGGTGAACGTGGTGGCCAAGCTGGTGCTGAAGTACAAC

GCCATCATCTGCCTGGAGGACCTGAACTTCGGCTTCAAGCGGGGCCGGCA

GAAGGTGGAGAAGCAGGTGTACCAGAAGTTCGAGAAGATGCTGATCGACA

AGCTGAACTACCTGGTGATCGACAAGAGCCGGGAGCAGACCAGCCCCAAG

GAGCTGGGCGGCGCCCTGAACGCCCTGCAGCTGACCAGCAAGTTCAAGAG

CTTCAAGGAGCTGGGCAAGCAGAGCGGCGTGATCTACTACGTGCCCGCCT

ACCTGACCAGCAAGATCGACCCCACCACCGGCTTCGCCAACCTGTTCTAC

ATGAAGTGCGAGAACGTGGAGAAAAGCAAGCGGTTCTTCGACGGCTTCGA

CTTCATCCGGTTCAACGCCCTGGAGAACGTGTTCGAGTTCGGCTTCGACT

ACCGGAGCTTCACCCAGCGGGCCTGCGGCATCAACAGCAAGTGGACCGTG

TGCACCAACGGCGAGCGGATCATCAAGTACCGGAACCCCGACAAGAACAA

CATGTTCGACGAGAAGGTGGTGGTGGTGACCGACGAGATGAAGAACCTGT

TCGAGCAGTACAAGATCCCCTACGAGGACGGCCGGAACGTGAAGGACATG

ATCATCAGCAACGAGGAGGCCGAGTTCTACCGGCGGCTGTACCGGCTGCT

GCAGCAGACCCTGCAGATGCGGAACAGCACCAGCGACGGCACCCGGGACT

ACATCATCAGCCCCGTGAAGAACAAGCGGGAGGCCTACTTCAACAGCGAG

CTGAGCGACGGCAGCGTGCCCAAGGACGCCGACGCCAACGGCGCCTACAA

CATCGCCCGGAAGGGCCTGTGGGTGCTGGAGCAGATCCGGCAGAAAAGCG

AGGGCGAGAAGATCAACCTGGCCATGACCAACGCCGAGTGGCTGGAGTAC

GCCCAGACCCACCTGCTGAAGCGGCCCGCCGCCACCAAGAAGGCCGGCCA

GGCCAAGAAGAAGAAGGGCAGCTACCCCTACGACGTGCCCGACTACGCCT

ACCCCTACGACGTGCCCGACTACGCCTACCCCTACGACGTGCCCGACTAC

GCCTGA
```

The corresponding amino acid sequence encoded by the nucleotide sequence set forth in SEQ ID NO: 3724 is set forth in SEQ ID NO: 3727, which is provided below.

```
                                           (SEQ ID NO: 3727)
MYYESLTKQYPVSKTIRNELIPIGKTLDNIRQNNILESDVKRKQNYEHVK

GILDEYHKQLINEALDNCTLPSLKIAAEIYLKNQKEVSDREDFNKTQDLL

RKEVVEKLKAHENFTKIGKKDILDLLEKLPSISEDDYNALESFRNFYTYF

TSYNKVRENLYSDKEKSSTVAYRLINENFPKFLDNVKSYRFVKTAGILAD

GLGEEEQDSLFIVETFNKTLTQDGIDTYNSQVGKINSSINLYNQKNQKAN

GFRKIPKMKMLYKQILSDREESFIDEFQSDEVLIDNVESYGSVLIESLKS

SKVSAFFDALRESKGKNVYVKNDLAKTAMSNIVFENWRTFDDLLNQEYDL

ANENKKKDDKYFEKRQKELKKNKSYSLEHLCNLSEDSCNLIENYIHQISD

DIENIIINNETFLRIVINEHDRSRKLAKNRKAVKAIKDFLDSIKVLEREL

KLINSSGQELEKDLIVYSAHEELLVELKQVDSLYNMTRNYLTKKPFSTEK

VKLNFNRSTLLNGWDRNKETDNLGVLLLKDGKYYLGIMNTSANKAFVNPP

VAKTEKVFKKVDYKLLPVPNQMLPKVFFAKSNIDFYNPSSEIYSNYKKGT

HKKGNMFSLEDCHNLIDFFKESISKHEDWSKFGFKFSDTASYNDISEFYR

EVEKQGYKLTYTDIDETYINDLIERNELYLFQIYNKDFSMYSKGKLNLHT

LYFMMLFDQRNIDDVVYKLNGEAEVFYRPASISEDELIIHKAGEEIKNKN

PNRARTKETSTFSYDIVKDKRYSKDKFTLHIPITMNFGVDEVKRFNDAVN

SAIRIDENVNVIGIDRGERNLLYVVVIDSKGNILEQISLNSIINKEYDIE

TDYHALLDEREGGRDKARKDWNTVENIRDLKAGYLSQVVNVVAKLVLKYN

AIICLEDLNFGFKRGRQKVEKQVYQKFEKMLIDKLNYLVIDKSREQTSPK

ELGGALNALQLTSKFKSFKELGKQSGVIYYVPAYLTSKIDPTTGFANLFY

MKCENVEKSKRFFDGFDFIRFNALENVFEFGFDYRSFTQRACGINSKWTV

CTNGERIIKYRNPDKNNMFDEKVVVVTDEMKNLFEQYKIPYEDGRNVKDM

IISNEEAEFYRRLYRLLQQTLQMRNSTSDGTRDYIISPVKNKREAYFNSE

LSDGSVPKDADANGAYNIARKGLWVLEQIRQKSEGEKINLAMTNAEWLEY

AQTHLL
```

Less conserved or unconserved regions that are spatially located distant from regions involved in Cpf1 activity, e.g., interface with the target nucleic acid molecule and/or gRNA, represent regions or domains are candidates for deletion without substantially affecting or decreasing Cpf1 activity.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. Methods of alignment of sequences for comparison are well known in the art. Optimal alignment of sequences for comparison can be conducted, e.g., by the local homology algorithm of Smith and Waterman, (1970) Adv. Appl. Math. 2:482c, by the homology alignment algorithm of Needleman and Wunsch, (1970) J. Mol. Biol. 48:443, by the search for similarity method of Pearson and Lipman, (1988) Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see, e.g., Brent et al., (2003) Current Protocols in Molecular Biology).

Two examples of algorithms that are suitable for determining percent sequence identity and sequence similarity are the BLAST and BLAST 2.0 algorithms, which are described in Altschul et al., (1977) Nuc. Acids Res. 25:3389-3402; and Altschul et al., (1990) J. Mol. Biol. 215:403-410, respectively. Software for performing BLAST analyses is publicly available through the National Center for Biotechnology Information.

The percent identity between two amino acid sequences can also be determined using the algorithm of E. Meyers and W. Miller, (1988) Comput. Appl. Biosci. 4:11-17) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (1970) J. Mol. Biol. 48:444-453) algorithm which has been incorporated into the GAP program in the GCG software package (available at www.gcg.com), using either a Blossom 62 matrix or a PAM250 matrix, and a gap weight of 16, 14, 12, 10, 8, 6, or 4 and a length weight of 1, 2, 3, 4, 5, or 6.

IV. Functional Analysis of Candidate Molecules

Candidate Cpf1 molecules, candidate gRNA molecules, candidate Cpf1 molecule/gRNA molecule complexes, can be evaluated by art-known methods or as described herein. For example, exemplary methods for evaluating the endonuclease activity of Cpf1 molecule are described, e.g., in Zetsche et al., Cell (2015); 163:759-771.

Binding and Cleavage Assay: Testing the Endonuclease Activity of Cpf1 Molecule

The ability of a Cpf1 molecule/gRNA molecule complex to bind to and cleave a target nucleic acid can be evaluated in a plasmid cleavage assay. In this assay, synthetic or in vitro-transcribed gRNA molecule is pre-annealed prior to the reaction by heating to 95° C. and slowly cooling down to room temperature. Native or restriction digest-linearized plasmid DNA (300 ng (~8 nM)) is incubated for 60 min at 37° C. with purified Cpf1 protein molecule (50-500 nM) and gRNA (50-500 nM, 1:1) in a Cpf1 plasmid cleavage buffer (20 mM HEPES pH 7.5, 150 mM KCl, 0.5 mM DTT, 0.1 mM EDTA) with or without 10 mM $MgCl_2$. The reactions are stopped with 5× DNA loading buffer (30% glycerol, 1.2% SDS, 250 mM EDTA), resolved by a 0.8 or 1% agarose gel electrophoresis and visualized by ethidium bromide staining. The resulting cleavage products indicate whether the Cpf1 molecule cleaves both DNA strands, or only one of the two strands. For example, linear DNA products indicate the cleavage of both DNA strands. Nicked open circular products indicate that only one of the two strands is cleaved.

Alternatively, the ability of a Cpf1 molecule/gRNA molecule complex to bind to and cleave a target nucleic acid can be evaluated in an oligonucleotide DNA cleavage assay. In this assay, DNA oligonucleotides (10 pmol) are radiolabeled by incubating with 5 units T4 polynucleotide kinase and ~3-6 pmol (~20-40 mCi) [γ-32P]-ATP in 1× T4 polynucleotide kinase reaction buffer at 37° C. for 30 min, in a 50 µL reaction. After heat inactivation (65° C. for 20 min), reactions are purified through a column to remove unincorporated label. Duplex substrates (100 nM) are generated by annealing labeled oligonucleotides with equimolar amounts of unlabeled complementary oligonucleotide at 95° C. for 3 min, followed by slow cooling to room temperature. For cleavage assays, gRNA molecules are annealed by heating to 95° C. for 30 s, followed by slow cooling to room temperature. Cpf1 (500 nM final concentration) is pre-incubated with the annealed gRNA molecules (500 nM) in cleavage assay buffer (20 mM HEPES pH 7.5, 100 mM KCl, 5 mM $MgCl_2$, 1 mM DTT, 5% glycerol) in a total volume of 9 µl. Reactions are initiated by the addition of 1 µl target DNA (10 nM) and incubated for 1 h at 37° C. Reactions are quenched by the addition of 20 µl of loading dye (5 mM EDTA, 0.025% SDS, 5% glycerol in formamide) and heated to 95° C. for 5 min. Cleavage products are resolved on 12% denaturing polyacrylamide gels containing 7 M urea and visualized by phosphorimaging. The resulting cleavage products indicate that whether the complementary strand, the non-complementary strand, or both, are cleaved.

One or both of these assays can be used to evaluate the suitability of a candidate gRNA molecule or candidate Cpf1 molecule.

Binding Assay: Testing the Binding of Cpf1 Molecule to Target DNA

Exemplary methods for evaluating the binding of Cpf1 molecule to target DNA are described, e.g., in Zetsche et al., Cell (2015); 163:759-771.

For example, in an electrophoretic mobility shift assay, target DNA duplexes are formed by mixing of each strand (10 nmol) in deionized water, heating to 95° C. for 3 min and slow cooling to room temperature. All DNAs are purified on 8% native gels containing 1× TBE. DNA bands are visualized by UV shadowing, excised, and eluted by soaking gel pieces in DEPC-treated $H_2O$. Eluted DNA is ethanol precipitated and dissolved in DEPC-treated $H_2O$. DNA samples are 5' end labeled with [γ-32P]-ATP using T4 polynucleotide kinase for 30 min at 37° C. Polynucleotide kinase is heat denatured at 65° C. for 20 min, and unincorporated radiolabel is removed using a column. Binding assays are performed in buffer containing 20 mM HEPES pH 7.5, 100 mM KCl, 5 mM $MgCl_2$, 1 mM DTT and 10% glycerol in a total volume of 10 µl. Cpf1 protein molecule is programmed with equimolar amounts of pre-annealed gRNA molecule and titrated from 100 pM to 1 µM. Radiolabeled DNA is added to a final concentration of 20 pM. Samples are incubated for 1 h at 37° C. and resolved at 4° C. on an 8% native polyacrylamide gel containing 1× TBE and 5 mM $MgCl_2$. Gels are dried and DNA visualized by phosphorimaging.

Differential Scanning Flourimetry (DSF)

The thermostability of Cpf1-gRNA ribonucleoprotein (RNP) complexes can be measured via DSF. This technique measures the thermostability of a protein, which can increase under favorable conditions such as the addition of a binding RNA molecule, e.g., a gRNA.

The assay is performed using two different protocols, one to test the best stoichiometric ratio of gRNA:Cpf1 protein and another to determine the best solution conditions for RNP formation.

To determine the best solution to form RNP complexes, a 2 uM solution of Cpf1 in water+10× SYPRO Orange® (Life Techonologies cat #S-6650) and dispensed into a 384 well plate. An equimolar amount of gRNA diluted in solutions with varied pH and salt is then added. After incubating at room temperature for 10' and brief centrifugation to remove any bubbles, a Bio-Rad CFX384™ Real-Time System C1000 Touch™ Thermal Cycler with the Bio-Rad CFX Manager software is used to run a gradient from 20° C. to 90° C. with a 1° increase in temperature every 10 seconds.

The second assay consists of mixing various concentrations of gRNA with 2 uM Cpf1 in optimal buffer from assay 1 above and incubating at RT for 10' in a 384 well plate. An equal volume of optimal buffer+10× SYPRO Orange® (Life Techonologies cat #S-6650) is added and the plate sealed with Microseal® B adhesive (MSB-1001). Following brief centrifugation to remove any bubbles, a Bio-Rad CFX384™ Real-Time System C1000 Touch™ Thermal Cycler with the Bio-Rad CFX Manager software is used to run a gradient from 20° C. to 90° C. with a 1° increase in temperature every 10 seconds.

V. Genome Editing Approaches

In general, it is to be understood that the alteration of any gene according to the methods described herein can be mediated by any mechanism and that any methods are not limited to a particular mechanism. Exemplary mechanisms that can be associated with the alteration of a gene include, but are not limited to, non-homologous end joining (e.g., classical or alternative), microhomology-mediated end joining (MMEJ), homology-directed repair (e.g., endogenous donor template mediated), and SDSA (synthesis dependent strand annealing). Described herein are exemplary methods for targeted knockout of one or both alleles of FAS, BID, CTLA4, PDCD1, CBLB or, PTPN6, B2M, TRAC and/or TRBC gene using NHEJ (see Section V.1). In certain embodiments, the disclosed methods may target two or more of FAS, BID, CTLA4, PDCD1, CBLB, PTPN6, B2M, TRAC and TRBC genes for knockout.

V.1 NHEJ Approaches for Gene Targeting

As described herein, nuclease-induced non-homologous end-joining (NHEJ) can be used to target gene-specific knockouts. Nuclease-induced NHEJ can also be used to remove (e.g., delete) sequence insertions in a gene of interest.

In certain embodiments, the genomic alterations associated with the methods described herein rely on nuclease-induced NHEJ and the error-prone nature of the NHEJ repair pathway. NHEJ repairs a double-strand break in the DNA by joining together the two ends; however, generally, the original sequence is restored only if two compatible ends, exactly as they were formed by the double-strand break, are perfectly ligated. The DNA ends of the double-strand break are frequently the subject of enzymatic processing, resulting in the addition or removal of nucleotides, at one or both strands, prior to rejoining of the ends. This results in the presence of insertion and/or deletion (indel) mutations in the DNA sequence at the site of the NHEJ repair. Two-thirds of these mutations typically alter the reading frame and, therefore, produce a non-functional protein. Additionally, mutations that maintain the reading frame, but which insert or delete a significant amount of sequence, can destroy functionality of the protein. This is locus dependent as mutations in critical functional domains are likely less tolerable than mutations in non-critical regions of the protein.

The indel mutations generated by NHEJ are unpredictable in nature; however, at a given break site certain indel sequences are favored and are over represented in the population, likely due to small regions of microhomology. The lengths of deletions can vary widely; most commonly in the 1-50 bp range, but they can easily reach greater than 100-200 bp. Insertions tend to be shorter and often include short duplications of the sequence immediately surrounding the break site. However, it is possible to obtain large insertions, and in these cases, the inserted sequence has often been traced to other regions of the genome or to plasmid DNA present in the cells.

Because NHEJ is a mutagenic process, it can also be used to delete small sequence motifs as long as the generation of a specific final sequence is not required. If a double-strand break is targeted near to a short target sequence, the deletion mutations caused by the NHEJ repair often span, and therefore remove, the unwanted nucleotides. For the deletion of larger DNA segments, introducing two double-strand breaks, one on each side of the sequence, can result in NHEJ between the ends with removal of the entire intervening sequence. Both of these approaches can be used to delete specific DNA sequences; however, the error-prone nature of NHEJ may still produce indel mutations at the site of repair.

NHEJ-mediated indels targeted to the gene, e.g., a coding region, e.g., an early coding region of a gene, of interest can be used to knockout (i.e., eliminate expression of) a gene of interest. For example, early coding region of a gene of interest includes sequence immediately following a transcription start site, within a first exon of the coding sequence, or within 500 bp of the transcription start site (e.g., less than 500, 450, 400, 350, 300, 250, 200, 150, 100 or 50 bp).

In certain embodiments, NHEJ-mediated indels are introduced into one or more T-cell expressed genes. In certain embodiments, in which a Cpf1 double-stranded nuclease is used to introduce mutations into two T-cell expressed genes, e.g., any two of FAS, BID, CTLA4, PDCD1, CBLB, PTPN6, B2M, TRAC and TRBC genes, individual gRNAs or gRNA pairs targeting both genes are provided together with the Cpf1 double-stranded nuclease. In certain embodiments, in which a Cpf1 double-stranded nuclease is used to introduce mutations into three T-cell expressed genes, e.g., any three of FAS, BID, CTLA4, PDCD1, CBLB, PTPN6, B2M, TRAC and TRBC genes, individual gRNAs or gRNA pairs targeting all three genes are provided together with the Cpf1 double-stranded nuclease. In certain embodiments, in which a Cpf1 double-stranded nuclease is used to introduce mutations into four T-cell expressed genes, e.g., any four of FAS, BID, CTLA4, PDCD1, CBLB, PTPN6, B2M, TRAC and TRBC genes, individual gRNAs or gRNA pairs targeting all four genes are provided together with the Cpf1 double-stranded nuclease. In certain embodiments, in which a Cpf1 double-stranded nuclease is used to introduce mutations into five T-cell expressed genes, e.g., any five of FAS, BID, CTLA4, PDCD1, CBLB, PTPN6, B2M, TRAC and TRBC genes, individual gRNAs or gRNA pairs targeting all five genes are provided together with the Cpf1 double-stranded nuclease. In certain embodiments, in which a Cpf1 double-stranded nuclease is used to introduce mutations into six T-cell expressed genes, e.g., any six of FAS, BID, CTLA4, PDCD1, CBLB, PTPN6, B2M, TRAC and TRBC genes, individual gRNAs or gRNA pairs targeting all six genes are provided together with the Cpf1 double-stranded nuclease. In certain embodiments, in which a Cpf1 double-stranded nuclease is used to introduce mutations into seven T-cell expressed genes, e.g., any seven of FAS, BID, CTLA4, PDCD1, CBLB, PTPN6, B2M, TRAC and TRBC genes, individual gRNAs or gRNA pairs targeting all seven genes are provided together with the Cpf1 double-stranded nuclease. In certain embodiments, in which a Cpf1 double-stranded nuclease is used to introduce mutations into eight T-cell expressed genes, e.g., each of FAS, BID, CTLA4, PDCD1, CBLB, PTPN6, B2M, TRAC and TRBC genes, individual gRNAs or gRNA pairs targeting all eight genes are provided together with the Cpf1 double-stranded nuclease.

Placement of Double Strand Breaks Relative to the Target Position

In certain embodiments, in which a gRNA and Cpf1 nuclease generate a double strand break for the purpose of inducing NHEJ-mediated indels, a gRNA, e.g., a unimodular gRNA molecule, is configured to position one double-strand break in close proximity to a nucleotide of the target position. In certain embodiments, the cleavage site is between 0-30 bp away from the target position (e.g., less than 30, less than 25, less than 20, less than 15, less than 10, less than 9, less than 8, less than 7, less than 6, less than 5, less than 4, less than 3, less than 2 or 1 bp from the target position). In certain embodiments, the cleavage site is between 1-24 bp away from the target position.

The double strand cleaving Cpf1 molecules can be used in the methods and compositions described herein to generate breaks both sides of a target position. Double strand breaks n be generated on both sides of a target position to remove the nucleic acid sequence between the two cuts (e.g., the region between the two breaks is deleted). In certain embodiments, two gRNAs are configured to position a double-strand break on both sides of a target position.

V.2 gRNAs and Cpf1 Molecules in Genome Editing Methods

The gRNA molecules disclosed herein (e.g. those disclosed in Section I) can be used with the Cpf1 molecules disclosed herein (e.g. those disclosed in Section III) that generate a double strand break to alter the sequence of a target nucleic acid, e.g., a target position or target genetic signature. In certain embodiments, the gRNA positions, e.g., when targeting a Cpf1 molecule that makes double strand breaks, a double strand break (i) within 50, 100, 150, 200, 250, 300, 350, 400, 450, or 500 nucleotides of a target position, or (ii) sufficiently close so that the target position is within the region of end resection.

VI. Target Cells

Cpf1 molecules and gRNA molecules, e.g., a Cpf1 molecule/gRNA molecule complex, can be used to manipulate a cell, e.g., to edit a target nucleic acid, in a wide variety of cells.

In certain embodiments, a cell is manipulated by editing (e.g., inducing a mutation in) one or more target genes, e.g., as described herein. In certain embodiments, the expression of one or more target gene (e.g., FAS, BID, CTLA4, PDCD1, CBLB, PTPN6, B2M, TRAC and/or TRBC gene) is modulated. In certain embodiments, a cell is manipulated ex vivo by editing (e.g., inducing a mutation in) one or more target genes and/or modulating the expression of one or more target gene, e.g., FAS, BID, CTLA4, PDCD1, CBLB, PTPN6, B2M, TRAC and/or TRBC gene, and administered to a subject. Sources of target cells for ex vivo manipulation may include, e.g., the subject's blood, the subject's cord blood, or the subject's bone marrow. Sources of target cells for ex vivo manipulation may also include, e.g., heterologous donor blood, cord blood, or bone marrow.

The Cpf1 and gRNA molecules described herein can be delivered to a target cell. In certain embodiments, the target cell is a T cell, e.g., a $CD8^+$ T cell (e.g., a $CD8^+$ naïve T cell, central memory T cell, or effector memory T cell), a $CD4^+$ T cell, a natural killer T cell (NKT cells), a regulatory T cell (Treg), a stem cell memory T cell, a lymphoid progenitor cell a hematopoietic stem cell, a natural killer cell (NK cell) or a dendritic cell. In certain embodiments, the target cell is an induced pluripotent stem (iPS) cell or a cell derived from an iPS cell, e.g., an iPS cell generated from a subject, manipulated to alter (e.g., induce a mutation in) or manipulate the expression of one or more target gene, e.g., FAS, BID, CTLA4, PDCD1, CBLB, PTPN6, B2M, TRAC and/or TRBC gene, and differentiated into, e.g., a T cell, e.g., a $CD8^+$ T cell (e.g., a $CD8^+$ naïve T cell, central memory T cell, or effector memory T cell), a $CD4^+$ T cell, a stem cell memory T cell, a lymphoid progenitor cell or a hematopoietic stem cell.

In certain embodiments, the target cell has been altered to contain specific T cell receptor (TCR) genes (e.g., a TRAC and TRBC gene). In certain embodiments, the TCR has binding specificity for a tumor associated antigen, e.g., carcinoembryonic antigen (CEA), GP100, melanoma antigen recognized by T cells 1 (MART1), melanoma antigen A3 (MAGEA3), NYESO1 or p53.

In certain embodiments, the target cell has been altered to contain a specific chimeric antigen receptor (CAR). In certain embodiments, the CAR has binding specificity for a tumor associated antigen, e.g., CD19, CD20, carbonic anhydrase IX (CAIX), CD171, CEA, ERBB2, GD2, alpha-folate receptor, Lewis Y antigen, prostate specific membrane antigen (PSMA) or tumor associated glycoprotein 72 (TAG72).

In certain embodiments, the target cell has been altered to bind one or more of the following tumor antigens, e.g., by a TCR or a CAR. Tumor antigens may include, but are not limited to, AD034, AKT1, BRAP, CAGE, CDX2, CLP, CT-7, CT8/HOM-TES-85, cTAGE-1, Fibulin-1, HAGE, HCA587/MAGE-C2, hCAP-G, HCE661, HER2/neu, HLA-Cw, HOM-HD-21/Galectin9, HOM-MEEL-40/SSX2, HOM-RCC-3.1.3/CAXII, HOXA7, HOXB6, Hu, HUB1, KM-HN-3, KM-KN-1, KOC1, KOC2, KOC3, KOC3, LAGE-1, MAGE-1, MAGE-4a, MPP11, MSLN, NNP-1, NY-BR-1, NY-BR-62, NY-BR-85, NY-CO-37, NY-CO-38, NY-ESO-1, NY-ESO-5, NY-LU-12, NY-REN-10, NY-REN-19/LKB/STK11, NY-REN-21, NY-REN-26/BCR, NY-REN-3/NY-CO-38, NY-REN-33/SNC6, NY-REN-43, NY-REN-65, NY-REN-9, NY-SAR-35, OGFr, PLU-1, Rab38, RBPJkappa, RHAMM, SCP1, SCP-1, SSX3, SSX4, SSX5, TOP2A, TOP2B, or Tyrosinase.

VII. Delivery, Formulations and Routes of Administration

The components, e.g., a Cpf1 molecule and gRNA molecule can be introduced into target cells in a variety of forms using a variety of delivery methods and formulations, see, e.g., Tables 2 and 3. When a Cpf1 or gRNA component is encoded as DNA for delivery, the DNA may typically but not necessarily include a control region, e.g., comprising a promoter, to effect expression. Useful promoters for Cpf1 molecule sequences include, e.g., CMV promoter, EF-1a promoter, EFS promoter, MSCV promoter, PGK promoter, CAG promoter, the Skeletal Alpha Actin promoter, the Muscle Creatine Kinase promoter, the Dystrophin promoter, the Alpha Myosin Heavy Chain promoter, and the Smooth Muscle Actin promoter promoters. Useful promoters for gRNAs include, e.g., H1, 75J, EF-1a, tRNA or U6 promoters. Promoters with similar or dissimilar strengths can be selected to tune the expression of components. Sequences encoding a Cpf1 molecule may comprise a nuclear localization signal (NLS), e.g., an SV40 NLS. In certain embodiments, the sequence encoding a Cpf1 molecule comprises at least two nuclear localization signals. In certain embodiments, a promoter for a Cpf1 molecule or a gRNA molecule may be, independently, inducible, tissue specific, or cell specific.

TABLE 2

Examples of the form in which the components can be delivered to a target cell

| Elements | | |
|---|---|---|
| Cpf1 Molecule(s) | gRNA molecule(s) | Comments |
| DNA | DNA | In certain embodiments, a Cpf1 molecule and a gRNA are transcribed from DNA. In certain embodiments, they are encoded on separate molecules. |
| | DNA | In certain embodiments, a Cpf1 molecule and a gRNA are transcribed from DNA, here from a single molecule. |

TABLE 2-continued

Examples of the form in which the components can be delivered to a target cell

| Elements | | |
|---|---|---|
| Cpf1 Molecule(s) | gRNA molecule(s) | Comments |
| DNA | RNA | In certain embodiments, a Cpf1 molecule is transcribed from DNA, and a gRNA is provided as in vitro transcribed or synthesized RNA |
| mRNA | RNA | In certain embodiments, a Cpf1 molecule is translated from in vitro transcribed mRNA, and a gRNA is provided as in vitro transcribed or synthesized RNA. |
| mRNA | DNA | In certain embodiments, a Cpf1 molecule is translated from in vitro transcribed mRNA, and a gRNA is transcribed from DNA. |
| Protein | DNA | In certain embodiments, a Cpf1 molecule is provided as a protein, and a gRNA is transcribed from DNA. |
| Protein | RNA | In certain embodiments, a Cpf1 molecule is provided as a protein, and a gRNA is provided as transcribed or synthesized RNA. This delivery method is referred to as "RNP delivery" |

Table 3 summarizes various delivery methods for the components of a CRISPR/Cpf1 system, e.g., the Cpf1 molecule component and the gRNA molecule component, as described herein.

TABLE 3

| | Delivery Vector/Mode | Delivery into Non-Dividing Cells | Duration of Expression | Genome Integration | Type of Molecule Delivered |
|---|---|---|---|---|---|
| | Physical (e.g., electroporation, particle gun, Calcium Phosphate transfection, cell compression or squeezing) | YES | Transient | NO | Nucleic Acids and Proteins |
| Viral | Retrovirus | NO | Stable | YES | RNA |
| | Lentivirus | YES | Stable | YES/NO with modifications | RNA |
| | Adenovirus | YES | Transient | NO | DNA |
| | Adeno-Associated Virus (AAV) | YES | Stable | NO | DNA |
| | Vaccinia Virus | YES | Very Transient | NO | DNA |
| | Herpes Simplex Virus | YES | Stable | NO | DNA |
| Non-Viral | Cationic Liposomes | YES | Transient | Depends on what is delivered | Nucleic Acids and Proteins |
| | Polymeric Nanoparticles | YES | Transient | Depends on what is delivered | Nucleic Acids and Proteins |
| Biological Non-Viral Delivery Vehicles | Attenuated Bacteria | YES | Transient | NO | Nucleic Acids |
| | Engineered Bacteriophages | YES | Transient | NO | Nucleic Acids |
| | Mammalian Virus-like Particles | YES | Transient | NO | Nucleic Acids |
| | Biological liposomes: Erythrocyte Ghosts and Exosomes | YES | Transient | NO | Nucleic Acids |

DNA-Based Delivery of a Cpf1 Molecule and/or One or More gRNA Molecule

Nucleic acid compositions encoding Cpf1 molecules and/or gRNA molecules can be administered to subjects or delivered into cells by art-known methods or as described herein. For example, Cpf1-encoding and/or gRNA-encoding DNA can be delivered, e.g., by vectors (e.g., viral or non-viral vectors), non-vector based methods (e.g., using naked DNA or DNA complexes), or a combination thereof.

In certain embodiments, the Cpf1- and/or gRNA-encoding DNA is delivered by a vector (e.g., viral vector/virus or plasmid).

In certain embodiments, the vector comprises a sequence that encodes a Cpf1 molecule and/or a gRNA molecule. In certain embodiments, the vector further comprise a sequence encoding a signal peptide (e.g., for nuclear localization, nucleolar localization, mitochondrial localization), fused, e.g., to a Cpf1 molecule sequence. For example, a vector can comprise a nuclear localization sequence (e.g., from SV40) fused to the sequence encoding the Cpf1 molecule.

One or more regulatory/control elements, e.g., a promoter, an enhancer, an intron, a polyadenylation signal, a Kozak consensus sequence, internal ribosome entry sites (IRES), a 2A sequence, and splice acceptor or donor can be included in the vectors. In certain embodiments, the promoter is recognized by RNA polymerase II (e.g., a CMV promoter). In certain embodiments, the promoter is recognized by RNA polymerase III (e.g., a U6 promoter). In certain embodiments, the promoter is a regulated promoter (e.g., inducible promoter). In certain embodiments, the promoter is a constitutive promoter. In certain embodiments, the promoter is a tissue specific promoter. In certain embodiments, the promoter is a viral promoter. In certain embodiments, the promoter is a non-viral promoter.

In certain embodiments, the vector or delivery vehicle is a viral vector (e.g., for generation of recombinant viruses). In certain embodiments, the virus is a DNA virus (e.g., dsDNA or ssDNA virus). In certain embodiments, the virus is an RNA virus (e.g., an ssRNA virus). Exemplary viral vectors/viruses include, e.g., retroviruses, lentiviruses, adenovirus, adeno-associated virus (AAV), vaccinia viruses, poxviruses, and herpes simplex viruses.

In certain embodiments, the virus infects dividing cells. In certain embodiments, the virus infects non-dividing cells. In certain embodiments, the virus infects both dividing and non-dividing cells. In certain embodiments, the virus can integrate into the host genome. In certain embodiments, the virus is engineered to have reduced immunity, e.g., in human. In certain embodiments, the virus is replication-competent. In certain embodiments, the virus is replication-defective, e.g., having one or more coding regions for the genes necessary for additional rounds of virion replication and/or packaging replaced with other genes or deleted. In certain embodiments, the virus causes transient expression of the Cpf1 molecule and/or the gRNA molecule. In certain embodiments, the virus causes long-lasting, e.g., at least 1 week, 2 weeks, 1 month, 2 months, 3 months, 6 months, 9 months, 1 year, 2 years, or permanent expression, of the Cpf1 molecule and/or the gRNA molecule. The packaging capacity of the viruses may vary, e.g., from at least about 4 kb to at least about 30 kb, e.g., at least about 5 kb, 10 kb, 15 kb, 20 kb, 25 kb, 30 kb, 35 kb, 40 kb, 45 kb, or 50 kb.

In certain embodiments, the viral vector recognizes a specific cell type or tissue. For example, the viral vector can be pseudotyped with a different/alternative viral envelope glycoprotein; engineered with a cell type-specific receptor (e.g., genetic modification(s) of one or more viral envelope glycoproteins to incorporate a targeting ligand such as a peptide ligand, a single chain antibody, or a growth factor); and/or engineered to have a molecular bridge with dual specificities with one end recognizing a viral glycoprotein and the other end recognizing a moiety of the target cell surface (e.g., a ligand-receptor, monoclonal antibody, avidin-biotin and chemical conjugation).

In certain embodiments, the Cpf1- and/or gRNA-encoding DNA is delivered by a recombinant retrovirus. In certain embodiments, the retrovirus (e.g., Moloney murine leukemia virus) comprises a reverse transcriptase, e.g., that allows integration into the host genome. In certain embodiments, the retrovirus is replication-competent. In certain embodiments, the retrovirus is replication-defective, e.g., having one or more coding regions for the genes necessary for additional rounds of virion replication and packaging replaced with other genes, or deleted.

In certain embodiments, the Cpf1- and/or gRNA-encoding DNA is delivered by a recombinant lentivirus. For example, the lentivirus is replication-defective, e.g., does not comprise one or more genes required for viral replication.

In certain embodiments, the Cpf1- and/or gRNA-encoding DNA is delivered by a recombinant adenovirus. In certain embodiments, the adenovirus is engineered to have reduced immunity in humans.

In certain embodiments, the Cpf1- and/or gRNA-encoding DNA is delivered by a recombinant AAV. In certain embodiments, the AAV does not incorporate its genome into that of a host cell, e.g., a target cell as describe herein. In certain embodiments, the AAV can incorporate its genome into that of a host cell, e.g., a target cell as described herein. In certain embodiments, the AAV is a self-complementary adeno-associated virus (scAAV), e.g., a scAAV that packages both strands which anneal together to form double stranded DNA. AAV serotypes that may be used in the disclosed methods, include AAV1, AAV2, modified AAV2 (e.g., modifications at Y444F, Y500F, Y730F and/or S662V), AAV3, modified AAV3 (e.g., modifications at Y705F, Y731F and/or T492V), AAV4, AAV5, AAV6, modified AAV6 (e.g., modifications at S663V and/or T492V), AAV8, AAV 8.2, AAV9, AAV rh 10, and pseudotyped AAV, such as AAV2/8, AAV2/5 and AAV2/6 can also be used in the disclosed methods. In certain embodiments, an AAV capsid that can be used in the methods described herein is a capsid sequence from serotype AAV1, AAV2, AAV3, AAV4, AAV5, AAV6, AAV7, AAV8, AAV9, AAV.rh8, AAV.rh10, AAV.rh32/33, AAV.rh43, AAV.rh64R1, or AAV7m8.

In certain embodiments, the Cpf1- and/or gRNA-encoding DNA is delivered in a re-engineered AAV capsid, e.g., with 50% or greater, e.g., 60% or greater, 70% or greater, 80% or greater, 90% or greater, or 95% or greater, sequence homology with a capsid sequence from serotypes AAV1, AAV2, AAV3, AAV4, AAV5, AAV6, AAV7, AAV8, AAV9, AAV.rh8, AAV.rh10, AAV.rh32/33, AAV.rh43, or AAV.rh64R1.

In certain embodiments, the Cpf1- and/or gRNA-encoding DNA is delivered by a chimeric AAV capsid. Exemplary chimeric AAV capsids include, but are not limited to, AAV9i1, AAV2i8, AAV-DJ, AAV2G9, AAV2i8G9, or AAV8G9.

In certain embodiments, the Cpf1- and/or gRNA-encoding DNA is delivered by a hybrid virus, e.g., a hybrid of one or more of the viruses described herein. In certain embodiments, the hybrid virus is hybrid of an AAV (e.g., of any AAV serotype), with a Bocavirus, B19 virus, porcine AAV, goose AAV, feline AAV, canine AAV, or MVM.

A packaging cell is used to form a virus particle that is capable of infecting a target cell. Such a cell includes a 293 cell, which can package adenovirus, and a w2 cell or a PA317 cell, which can package retrovirus. A viral vector used in gene therapy is usually generated by a producer cell line that packages a nucleic acid vector into a viral particle. The vector typically contains the minimal viral sequences required for packaging and subsequent integration into a host or target cell (if applicable), with other viral sequences being replaced by an expression cassette encoding the protein to be expressed, eg. Cpf1. For example, an AAV vector used in gene therapy typically only possesses inverted terminal repeat (ITR) sequences from the AAV genome which are required for packaging and gene expression in the host or target cell. The missing viral functions are supplied in trans by the packaging cell line. Henceforth, the viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In certain embodiments, the viral vector has the ability of cell type recognition. For example, the viral vector can be pseudotyped with a different/alternative viral envelope glycoprotein; engineered with a cell type-specific receptor (e.g., genetic modification of the viral envelope glycoproteins to incorporate targeting ligands such as a peptide ligand, a single chain antibody, a growth factor); and/or engineered to have a molecular bridge with dual specificities with one end recognizing a viral glycoprotein and the other end recognizing a moiety of the target cell surface (e.g., ligand-receptor, monoclonal antibody, avidin-biotin and chemical conjugation).

In certain embodiments, the viral vector achieves cell type specific expression. For example, a tissue-specific promoter can be constructed to restrict expression of the transgene (Cpf1 and gRNA) in only a specific target cell. The specificity of the vector can also be mediated by microRNA-dependent control of transgene expression. In certain embodiments, the viral vector has increased efficiency of fusion of the viral vector and a target cell membrane. For example, a fusion protein such as fusion-competent hemagglutinin (HA) can be incorporated to increase viral uptake into cells. In certain embodiments, the viral vector has the ability of nuclear localization. For example, a virus that requires the breakdown of the nuclear membrane (during cell division) and therefore will not infect a non-diving cell can be altered to incorporate a nuclear localization peptide in the matrix protein of the virus thereby enabling the transduction of non-proliferating cells.

In certain embodiments, the Cpf1- and/or gRNA-encoding DNA is delivered by a non-vector based method (e.g., using naked DNA or DNA complexes). For example, the DNA can be delivered, e.g., by organically modified silica or silicate (Ormosil), electroporation, transient cell compression or squeezing (eg, as described in Lee, et al [2012] *Nano Lett* 12: 6322-27), gene gun, sonoporation, magnetofection, lipid-mediated transfection, dendrimers, inorganic nanoparticles, calcium phosphates, or a combination thereof.

In certain embodiments, delivery via electroporation comprises mixing the cells with the Cpf1- and/or gRNA-encoding DNA in a cartridge, chamber or cuvette and applying one or more electrical impulses of defined duration and amplitude. In certain embodiments, delivery via electroporation is performed using a system in which cells are mixed with the Cpf1- and/or gRNA-encoding DNA in a vessel connected to a device (eg, a pump) which feeds the mixture into a cartridge, chamber or cuvette wherein one or more electrical impulses of defined duration and amplitude are applied, after which the cells are delivered to a second vessel.

In certain embodiments, the Cpf1- and/or gRNA-encoding DNA is delivered by a combination of a vector and a non-vector based method. For example, a virosome comprises a liposome combined with an inactivated virus (e.g., HIV or influenza virus), which can result in more efficient gene transfer than either a viral or a liposomal method alone.

In certain embodiments, the delivery vehicle is a non-viral vector. In certain embodiments, the non-viral vector is an inorganic nanoparticle. Exemplary inorganic nanoparticles include, e.g., magnetic nanoparticles (e.g., $Fe_3MnO_2$) and silica. The outer surface of the nanoparticle can be conjugated with a positively charged polymer (e.g., polyethylenimine, polylysine, polyserine) which allows for attachment (e.g., conjugation or entrapment) of payload. In certain embodiments, the non-viral vector is an organic nanoparticle. Exemplary organic nanoparticles include, e.g., SNALP liposomes that contain cationic lipids together with neutral helper lipids which are coated with polyethylene glycol (PEG), and protamine-nucleic acid complexes coated with lipid coating. Exemplary lipids for gene transfer are shown below in Table 4.

TABLE 4

Lipids Used for Gene Transfer

| Lipid | Abbreviation | Feature |
|---|---|---|
| 1,2-Dioleoyl-sn-glycero-3-phosphatidylcholine | DOPC | Helper |
| 1,2-Dioleoyl-sn-glycero-3-phosphatidylethanolamine | DOPE | Helper |
| Cholesterol | | Helper |
| N-[1-(2,3-Dioleyloxy)propyl]N,N,N-trimethylammonium chloride | DOTMA | Cationic |
| 1,2-Dioleoyloxy-3-trimethylammonium-propane | DOTAP | Cationic |
| Dioctadecylamidoglycylspermine | DOGS | Cationic |
| N-(3-Aminopropyl)-N,N-dimethyl-2,3-bis(dodecyloxy)-1-propanaminium bromide | GAP-DLRIE | Cationic |
| Cetyltrimethylammonium bromide | CTAB | Cationic |
| 6-Lauroxyhexyl ornithinate | LHON | Cationic |
| 1-(2,3-Dioleoyloxypropyl)-2,4,6-trimethylpyridinium | 2Oc | Cationic |
| 2,3-Dioleyloxy-N-[2(sperminecarboxamido-ethyl]-N,N-dimethyl-1-propanaminium trifluoroacetate | DOSPA | Cationic |

TABLE 4-continued

Lipids Used for Gene Transfer

| Lipid | Abbreviation | Feature |
|---|---|---|
| 1,2-Dioleyl-3-trimethylammonium-propane | DOPA | Cationic |
| N-(2-Hydroxyethyl)-N,N-dimethyl-2,3-bis(tetradecyloxy)-1-propanaminium bromide | MDRIE | Cationic |
| Dimyristooxypropyl dimethyl hydroxyethyl ammonium bromide | DMRI | Cationic |
| 3β-[N-(N',N'-Dimethylaminoethane)-carbamoyl]cholesterol | DC-Chol | Cationic |
| Bis-guanidium-tren-cholesterol | BGTC | Cationic |
| 1,3-Diodeoxy-2-(6-carboxy-spermyl)-propylamide | DOSPER | Cationic |
| Dimethyloctadecylammonium bromide | DDAB | Cationic |
| Dioctadecylamidoglicylspermidin | DSL | Cationic |
| rac-[(2,3-Dioctadecyloxypropyl)(2-hydroxyethyl)]-dimethylammonium chloride | CLIP-1 | Cationic |
| rac-[2(2,3-Dihexadecyloxypropyl-oxymethyloxy)ethyl]trimethylammonium bromide | CLIP-6 | Cationic |
| Ethyldimyristoylphosphatidylcholine | EDMPC | Cationic |
| 1,2-Distearyloxy-N,N-dimethyl-3-aminopropane | DSDMA | Cationic |
| 1,2-Dimyristoyl-trimethylammonium propane | DMTAP | Cationic |
| O,O'-Dimyristyl-N-lysyl aspartate | DMKE | Cationic |
| 1,2-Distearoyl-sn-glycero-3-ethylphosphocholine | DSEPC | Cationic |
| N-Palmitoyl D-erythro-sphingosyl carbamoyl-spermine | CCS | Cationic |
| N-t-Butyl-N0-tetradecyl-3-tetradecylaminopropionamidine | diC14-amidine | Cationic |
| Octadecenolyoxy[ethyl-2-heptadecenyl-3 hydroxyethyl] imidazolinium chloride | DOTIM | Cationic |
| N1-Cholesteryloxycarbonyl-3,7-diazanonane-1,9-diamine | CDAN | Cationic |
| 2-(3-[Bis(3-amino-propyl)-amino]propylamino)-N-ditetradecylcarbamoylme-ethyl-acetamide | RPR209120 | Cationic |
| 1,2-dilinoleyloxy-3-dimethylaminopropane | DLinDMA | Cationic |
| 2,2-dilinoleyl-4-dimethylaminoethyl-[1,3]-dioxolane | DLin-KC2-DMA | Cationic |
| dilinoleyl-methyl-4-dimethylaminobutyrate | DLin-MC3-DMA | Cationic |

Exemplary polymers for gene transfer are shown below in Table 5.

TABLE 5

Polymers Used for Gene Transfer

| Polymer | Abbreviation |
|---|---|
| Poly(ethylene)glycol | PEG |
| Polyethylenimine | PEI |
| Dithiobis(succinimidylpropionate) | DSP |
| Dimethyl-3,3'-dithiobispropionimidate | DTBP |
| Poly(ethylene imine) biscarbamate | PEIC |
| Poly(L-lysine) | PLL |
| Histidine modified PLL | |
| Poly(N-vinylpyrrolidone) | PVP |
| Poly(propylenimine) | PPI |
| Poly(amidoamine) | PAMAM |
| Poly(amido ethylenimine) | SS-PAEI |
| Triethylenetetramine | TETA |
| Poly(β-aminoester) | |
| Poly(4-hydroxy-L-proline ester) | PHP |
| Poly(allylamine) | |
| Poly(α-[4-aminobutyl]-L-glycolic acid) | PAGA |
| Poly(D,L-lactic-co-glycolic acid) | PLGA |
| Poly(N-ethyl-4-vinylpyridinium bromide) | |
| Poly(phosphazene)s | PPZ |
| Poly(phosphoester)s | PPE |
| Poly(phosphoramidate)s | PPA |
| Poly(N-2-hydroxypropylmethacrylamide) | pHPMA |
| Poly (2-(dimethylamino)ethyl methacrylate) | pDMAEMA |
| Poly(2-aminoethyl propylene phosphate) | PPE-EA |
| Chitosan | |
| Galactosylated chitosan | |
| N-Dodacylated chitosan | |
| Histone | |
| Collagen | |
| Dextran-spermine | D-SPM |

In certain embodiments, the vehicle has targeting modifications to increase target cell update of nanoparticles and liposomes, e.g., cell specific antigens, monoclonal antibodies, single chain antibodies, aptamers, polymers, sugars, and cell penetrating peptides. In certain embodiments, the vehicle uses fusogenic and endosome-destabilizing peptides/polymers. In certain embodiments, the vehicle undergoes acid-triggered conformational changes (e.g., to accelerate endosomal escape of the cargo). In certain embodiments, a stimulus-cleavable polymer is used, e.g., for release in a cellular compartment. For example, disulfide-based cationic polymers that are cleaved in the reducing cellular environment can be used.

In certain embodiments, the delivery vehicle is a biological non-viral delivery vehicle. In certain embodiments, the vehicle is an attenuated bacterium (e.g., naturally or artificially engineered to be invasive but attenuated to prevent pathogenesis and expressing the transgene (e.g., *Listeria monocytogenes*, certain *Salmonella* strains, *Bifidobacterium longum*, and modified *Escherichia coli*), bacteria having nutritional and tissue-specific tropism to target specific cells, bacteria having modified surface proteins to alter target cell specificity). In certain embodiments, the vehicle is a genetically modified bacteriophage (e.g., engineered phages having large packaging capacity, less immunogenicity, containing mammalian plasmid maintenance sequences and having incorporated targeting ligands). In certain embodiments, the vehicle is a mammalian virus-like particle. For example, modified viral particles can be generated (e.g., by purification of the "empty" particles followed by ex vivo assembly of the virus with the desired cargo). The vehicle can also be engineered to incorporate targeting ligands to alter target tissue specificity. In certain embodiments, the vehicle is a biological liposome. For example, the biological liposome is a phospholipid-based particle derived from human cells (e.g., erythrocyte ghosts, which are red blood cells broken down into spherical structures derived from the subject (e.g., tissue targeting can be achieved by attachment of various tissue or cell-specific ligands), or secretory exosomes—subject-derived membrane-bound nanovescicles (30-100 nm) of endocytic origin (e.g., can be produced from various cell types and can therefore be taken up by cells without the need for targeting ligands).

In certain embodiments, one or more nucleic acid compositions (e.g., DNA molecules) other than the components of a CRISPR/Cpf1 system, e.g., the Cpf1 molecule component and/or the gRNA molecule component described herein, are delivered. In certain embodiments, the nucleic acid composition is delivered at the same time as one or more of the components of the CRISPR/Cpf1 system. In certain embodiments, the nucleic acid composition is delivered before or after (e.g., less than about 30 minutes, 1 hour, 2 hours, 3 hours, 6 hours, 9 hours, 12 hours, 1 day, 2 days, 3 days, 1 week, 2 weeks, or 4 weeks) one or more of the components of the Cpf1 system are delivered. In certain embodiments, the nucleic acid composition is delivered by a different means from one or more of the components of the CRISPR/Cpf1 system, e.g., the Cpf1 molecule component and/or the gRNA molecule component. The nucleic acid composition can be delivered by any of the delivery methods described herein. For example, the nucleic acid molecule can be delivered by a viral vector, e.g., a retrovirus or a lentivirus, and the Cpf1 molecule component and/or the gRNA molecule component can be delivered by electroporation. In certain embodiments, the nucleic acid composition encodes a FAS, BID, CTLA4, PDCD1, CBLB, PTPN6, B2M, TRAC or TRBC gene.

Delivery of RNA Encoding a Cpf1 Molecule

RNA encoding Cpf1 molecules and/or gRNA molecules can be delivered into cells, e.g., target cells described herein, by art-known methods or as described herein. For example, Cpf1-encoding and/or gRNA-encoding RNA can be delivered, e.g., by microinjection, electroporation, transient cell compression or squeezing (eg, as described in Lee, et al [2012] Nano Lett 12: 6322-27), lipid-mediated transfection, peptide-mediated delivery, or a combination thereof. Cpf1-encoding and/or gRNA-encoding RNA can be conjugated to molecules promoting uptake by the target cells (e.g., target cells described herein).

In certain embodiments, delivery via electroporation comprises mixing the cells with the RNA encoding Cpf1 molecules and/or gRNA molecules in a cartridge, chamber or cuvette and applying one or more electrical impulses of defined duration and amplitude. In certain embodiments, delivery via electroporation is performed using a system in which cells are mixed with the RNA encoding Cpf1 molecules and/or gRNA molecules in a vessel connected to a device (eg, a pump) which feeds the mixture into a cartridge, chamber or cuvette wherein one or more electrical impulses of defined duration and amplitude are applied, after which the cells are delivered to a second vessel. Cpf1-encoding and/or gRNA-encoding RNA can be conjugated to molecules promoting uptake by the target cells (e.g., target cells described herein).

Delivery of Cpf1 Molecule Protein

Cpf1 molecules can be delivered into cells by art-known methods or as described herein. For example, Cpf1 protein molecules can be delivered, e.g., by microinjection, electroporation, transient cell compression or squeezing (e.g., as described in Lee, et al [2012] Nano Lett 12: 6322-27), lipid-mediated transfection, peptide-mediated delivery, or a combination thereof. Delivery can be accompanied by a DNA encoding a gRNA or by a gRNA.

In certain embodiments, delivery via electroporation comprises mixing the cells with the Cpf1 molecules with or without gRNA molecules in a cartridge, chamber or cuvette and applying one or more electrical impulses of defined duration and amplitude. In certain embodiments, delivery via electroporation is performed using a system in which cells are mixed with the Cpf1 molecules with or without gRNA molecules in a vessel connected to a device (e.g., a pump) which feeds the mixture into a cartridge, chamber or cuvette wherein one or more electrical impulses of defined duration and amplitude are applied, after which the cells are delivered to a second vessel.

RNP Delivery of Cpf1 Molecule Protein and gRNA

In certain embodiments, the Cpf1 molecule and gRNA are delivered to target cells via Ribonucleoprotein (RNP) delivery. In certain embodiments, the Cpf1 molecule is provided as a protein, and the gRNA molecule is provided as transcribed or synthesized RNA. The gRNA molecule can be generated by chemical synthesis. In certain embodiments, the gRNA molecule forms a RNP complex with the Cpf1 molecule protein under suitable condition prior to delivery to the target cells. In certain embodiments, the suitable condition comprises incubating the Cpf1 molecule protein and the gRNA at room temperature for at least about 10 minutes. The RNP complex can be delivered to the target cells by any suitable methods known in the art, e.g., by electroporation, lipid-mediated transfection, protein or DNA-based shuttle, mechanical force, or hydraulic force. In certain embodiments, the RNP complex is delivered to the target cells by electroporation.

VIII. Modified Nucleosides, Nucleotides, and Nucleic Acids

Modified nucleosides and modified nucleotides can be present in nucleic acids, e.g., particularly gRNA, but also nucleic acids encoding a Cpf1 molecule. Modifications disclosed in this section can be made in addition to or instead of any of the specific gRNA molecule modifications described above. As described herein, "nucleoside" is defined as a compound containing a five-carbon sugar molecule (a pentose or ribose) or derivative thereof, and an organic base, purine or pyrimidine, or a derivative thereof. As described herein, "nucleotide" is defined as a nucleoside further comprising a phosphate group.

Modified nucleosides and nucleotides can include one or more of:
  (i) alteration, e.g., replacement, of one or both of the non-linking phosphate oxygens and/or of one or more of the linking phosphate oxygens in the phosphodiester backbone linkage;
  (ii) alteration, e.g., replacement, of a constituent of the ribose sugar, e.g., of the 2' hydroxyl on the ribose sugar;
  (iii) wholesale replacement of the phosphate moiety with "dephospho" linkers;
  (iv) modification or replacement of a naturally occurring nucleobase;
  (v) replacement or modification of the ribose-phosphate backbone;
  (vi) modification of the 3' end or 5' end of the oligonucleotide, e.g., removal, modification or replacement of a terminal phosphate group or conjugation of a moiety; and
  (vii) modification of the sugar.

The modifications listed above can be combined to provide modified nucleosides and nucleotides that can have two, three, four, or more modifications. For example, a modified nucleoside or nucleotide can have a modified sugar and a modified nucleobase. In certain embodiments, every base of a gRNA is modified, e.g., all bases have a modified phosphate group, e.g., all are phosphorothioate groups. In certain embodiments, all, or substantially all, of the phosphate groups of a unimolecular or modular gRNA molecule are replaced with phosphorothioate groups.

In certain embodiments, modified nucleotides, e.g., nucleotides having modifications as described herein, can be incorporated into a nucleic acid, e.g., a "modified nucleic acid." In certain embodiments, the modified nucleic acids comprise one, two, three or more modified nucleotides. In certain embodiments, at least 5% (e.g., at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100%) of the positions in a modified nucleic acid are a modified nucleotides.

Unmodified nucleic acids can be prone to degradation by, e.g., cellular nucleases. For example, nucleases can hydrolyze nucleic acid phosphodiester bonds. Accordingly, in one aspect the modified nucleic acids described herein can contain one or more modified nucleosides or nucleotides, e.g., to introduce stability toward nucleases.

In certain embodiments, the modified nucleosides, modified nucleotides, and modified nucleic acids described herein can exhibit a reduced innate immune response when introduced into a population of cells. The term "innate immune response" includes a cellular response to exogenous nucleic acids, including single stranded nucleic acids, generally of viral or bacterial origin, which involves the induction of cytokine expression and release, particularly the interferons, and cell death. In certain embodiments, the modified nucleosides, modified nucleotides, and modified nucleic acids described herein can disrupt binding of a major groove interacting partner with the nucleic acid. In certain embodiments, the modified nucleosides, modified nucleotides, and modified nucleic acids described herein can exhibit a reduced innate immune response when introduced into a population of cells and also disrupt binding of a major groove interacting partner with the nucleic acid.

Definitions of Chemical Groups

As used herein, "alkyl" is meant to refer to a saturated hydrocarbon group which is straight-chained or branched. Example alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. An alkyl group can contain from 1 to about 20, from 2 to about 20, from 1 to about 12, from 1 to about 8, from 1 to about 6, from 1 to about 4, or from 1 to about 3 carbon atoms.

As used herein, "aryl" refers to monocyclic or polycyclic (e.g., having 2, 3 or 4 fused rings) aromatic hydrocarbons such as, for example, phenyl, naphthyl, anthracenyl, phenanthrenyl, indanyl, indenyl, and the like. In certain embodiments, aryl groups have from 6 to about 20 carbon atoms.

As used herein, "alkenyl" refers to an aliphatic group containing at least one double bond.

As used herein, "alkynyl" refers to a straight or branched hydrocarbon chain containing 2-12 carbon atoms and characterized in having one or more triple bonds. Examples of alkynyl groups include, but are not limited to, ethynyl, propargyl, and 3-hexynyl.

As used herein, "arylalkyl" or "aralkyl" refers to an alkyl moiety in which an alkyl hydrogen atom is replaced by an aryl group. Aralkyl includes groups in which more than one hydrogen atom has been replaced by an aryl group. Examples of "arylalkyl" or "aralkyl" include benzyl, 2-phenylethyl, 3-phenylpropyl, 9-fluorenyl, benzhydryl, and trityl groups.

As used herein, "cycloalkyl" refers to a cyclic, bicyclic, tricyclic, or polycyclic non-aromatic hydrocarbon groups having 3 to 12 carbons. Examples of cycloalkyl moieties include, but are not limited to, cyclopropyl, cyclopentyl, and cyclohexyl.

As used herein, "heterocyclyl" refers to a monovalent radical of a heterocyclic ring system. Representative heterocyclyls include, without limitation, tetrahydrofuranyl, tetrahydrothienyl, pyrrolidinyl, pyrrolidonyl, piperidinyl, pyrrolinyl, piperazinyl, dioxanyl, dioxolanyl, diazepinyl, oxazepinyl, thiazepinyl, and morpholinyl.

As used herein, "heteroaryl" refers to a monovalent radical of a heteroaromatic ring system. Examples of heteroaryl moieties include, but are not limited to, imidazolyl, oxazolyl, thiazolyl, triazolyl, pyrrolyl, furanyl, indolyl, thiophenyl pyrazolyl, pyridinyl, pyrazinyl, pyridazinyl, pyrimidinyl, indolizinyl, purinyl, naphthyridinyl, quinolyl, and pteridinyl.

Phosphate Backbone Modifications

The Phosphate Group

In certain embodiments, the phosphate group of a modified nucleotide can be modified by replacing one or more of the oxygens with a different substituent. Further, the modified nucleotide, e.g., modified nucleotide present in a modified nucleic acid, can include the wholesale replacement of an unmodified phosphate moiety with a modified phosphate as described herein. In certain embodiments, the modification of the phosphate backbone can include alterations that result in either an uncharged linker or a charged linker with unsymmetrical charge distribution.

Examples of modified phosphate groups include, phosphorothioate, phosphoroselenates, borano phosphates, borano phosphate esters, hydrogen phosphonates, phosphoroamidates, alkyl or aryl phosphonates and phosphotriesters. In certain embodiments, one of the non-bridging phosphate oxygen atoms in the phosphate backbone moiety can be replaced by any of the following groups: sulfur (S), selenium (Se), $BR_3$ (wherein R can be, e.g., hydrogen, alkyl, or aryl), C (e.g., an alkyl group, an aryl group, and the like), H, $NR_2$ (wherein R can be, e.g., hydrogen, alkyl, or aryl), or OR (wherein R can be, e.g., alkyl or aryl). The phosphorous atom in an unmodified phosphate group is achiral. However, replacement of one of the non-bridging oxygens with one of the above atoms or groups of atoms can render the phosphorous atom chiral; that is to say that a phosphorous atom in a phosphate group modified in this way is a stereogenic center. The stereogenic phosphorous atom can possess either the "R" configuration (herein Rp) or the "S" configuration (herein Sp).

Phosphorodithioates have both non-bridging oxygens replaced by sulfur. The phosphorus center in the phosphorodithioates is achiral which precludes the formation of oligoribonucleotide diastereomers. In certain embodiments, modifications to one or both non-bridging oxygens can also include the replacement of the non-bridging oxygens with a group independently selected from S, Se, B, C, H, N, and OR (R can be, e.g., alkyl or aryl).

The phosphate linker can also be modified by replacement of a bridging oxygen, (i.e., the oxygen that links the phosphate to the nucleoside), with nitrogen (bridged phosphoroamidates), sulfur (bridged phosphorothioates) and carbon (bridged methylenephosphonates). The replacement can occur at either linking oxygen or at both of the linking oxygens.

Replacement of the Phosphate Group

The phosphate group can be replaced by non-phosphorus containing connectors. In certain embodiments, the charge phosphate group can be replaced by a neutral moiety.

Examples of moieties which can replace the phosphate group can include, without limitation, e.g., methyl phosphonate, hydroxylamino, siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo and methyleneoxymethylimino.

Replacement of the Ribophosphate Backbone

Scaffolds that can mimic nucleic acids can also be constructed wherein the phosphate linker and ribose sugar are replaced by nuclease resistant nucleoside or nucleotide surrogates. In certain embodiments, the nucleobases can be tethered by a surrogate backbone. Examples can include, without limitation, the morpholino, cyclobutyl, pyrrolidine and peptide nucleic acid (PNA) nucleoside surrogates.

Sugar Modifications

The modified nucleosides and modified nucleotides can include one or more modifications to the sugar group. For example, the 2' hydroxyl group (OH) can be modified or replaced with a number of different "oxy" or "deoxy" substituents. In certain embodiments, modifications to the 2' hydroxyl group can enhance the stability of the nucleic acid since the hydroxyl can no longer be deprotonated to form a 2'-alkoxide ion. The 2'-alkoxide can catalyze degradation by intramolecular nucleophilic attack on the linker phosphorus atom.

Examples of "oxy"-2' hydroxyl group modifications can include alkoxy or aryloxy (OR, wherein "R" can be, e.g., alkyl, cycloalkyl, aryl, aralkyl, heteroaryl or a sugar); polyethyleneglycols (PEG), $O(CH_2CH_2O)_nCH_2CH_2OR$ wherein R can be, e.g., H or optionally substituted alkyl, and n can be an integer from 0 to 20 (e.g., from 0 to 4, from 0 to 8, from 0 to 10, from 0 to 16, from 1 to 4, from 1 to 8, from 1 to 10, from 1 to 16, from 1 to 20, from 2 to 4, from 2 to 8, from 2 to 10, from 2 to 16, from 2 to 20, from 4 to 8, from 4 to 10, from 4 to 16, and from 4 to 20). In certain embodiments, the "oxy"-2' hydroxyl group modification can include "locked" nucleic acids (LNA) in which the 2' hydroxyl can be connected, e.g., by a $C_{1-6}$ alkylene or $C_{1-6}$ heteroalkylene bridge, to the 4' carbon of the same ribose sugar, where exemplary bridges can include methylene, propylene, ether, or amino bridges; O-amino (wherein amino can be, e.g., $NH_2$; alkylamino, dialkylamino, heterocyclyl, arylamino, diarylamino, heteroarylamino, or diheteroarylamino, ethylenediamine, or polyamino) and aminoalkoxy, $O(CH_2)_n$-amino, (wherein amino can be, e.g., $NH_2$; alkylamino, dialkylamino, heterocyclyl, arylamino, diarylamino, heteroarylamino, or diheteroarylamino, ethylenediamine, or polyamino). In certain embodiments, the "oxy"-2' hydroxyl group modification can include the methoxyethyl group (MOE), ($OCH_2CH_2OCH_3$, e.g., a PEG derivative).

"Deoxy" modifications can include hydrogen (i.e. deoxyribose sugars, e.g., at the overhang portions of partially ds RNA); halo (e.g., bromo, chloro, fluoro, or iodo); amino (wherein amino can be, e.g., $NH_2$; alkylamino, dialkylamino, heterocyclyl, arylamino, diarylamino, heteroarylamino, diheteroarylamino, or amino acid); $NH(CH_2CH_2NH)_nCH_2CH_2$-amino (wherein amino can be, e.g., as described herein), —NHC(O)R (wherein R can be, e.g., alkyl, cycloalkyl, aryl, aralkyl, heteroaryl or sugar), cyano; mercapto; alkyl-thio-alkyl; thioalkoxy; and alkyl, cycloalkyl, aryl, alkenyl and alkynyl, which may be optionally substituted with e.g., an amino as described herein.

The sugar group can also contain one or more carbons that possess the opposite stereochemical configuration than that of the corresponding carbon in ribose. Thus, a modified nucleic acid can include nucleotides containing e.g., arabinose, as the sugar. The nucleotide "monomer" can have an alpha linkage at the 1' position on the sugar, e.g., alpha-nucleosides. The modified nucleic acids can also include "abasic" sugars, which lack a nucleobase at C-1'. These abasic sugars can also be further modified at one or more of the constituent sugar atoms. The modified nucleic acids can also include one or more sugars that are in the L form, e.g. L-nucleosides.

Generally, RNA includes the sugar group ribose, which is a 5-membered ring having an oxygen. Exemplary modified nucleosides and modified nucleotides can include, without limitation, replacement of the oxygen in ribose (e.g., with sulfur (S), selenium (Se), or alkylene, such as, e.g., methylene or ethylene); addition of a double bond (e.g., to replace ribose with cyclopentenyl or cyclohexenyl); ring contraction of ribose (e.g., to form a 4-membered ring of cyclobutane or oxetane); ring expansion of ribose (e.g., to form a 6- or 7-membered ring having an additional carbon or heteroatom, such as for example, anhydrohexitol, altritol, mannitol, cyclohexanyl, cyclohexenyl, and morpholino that also has a phosphoramidate backbone). In certain embodiments, the modified nucleotides can include multicyclic forms (e.g., tricyclo; and "unlocked" forms, such as glycol nucleic acid (GNA) (e.g., R-GNA or S-GNA, where ribose is replaced by glycol units attached to phosphodiester bonds), threose nucleic acid (TNA, where ribose is replaced with α-L-threofuranosyl-(3'→2')).

Modifications on the Nucleobase

The modified nucleosides and modified nucleotides described herein, which can be incorporated into a modified nucleic acid, can include a modified nucleobase. Examples of nucleobases include, but are not limited to, adenine (A), guanine (G), cytosine (C), and uracil (U). These nucleobases can be modified or wholly replaced to provide modified nucleosides and modified nucleotides that can be incorporated into modified nucleic acids. The nucleobase of the nucleotide can be independently selected from a purine, a pyrimidine, a purine or pyrimidine analog. In certain embodiments, the nucleobase can include, for example, naturally-occurring and synthetic derivatives of a base.

Uracil

In certain embodiments, the modified nucleobase is a modified uracil. Exemplary nucleobases and nucleosides having a modified uracil include without limitation pseudouridine (ψ), pyridin-4-one ribonucleoside, 5-aza-uridine, 6-aza-uridine, 2-thio-5-aza-uridine, 2-thio-uridine (s2U), 4-thio-uridine (s4U), 4-thio-pseudouridine, 2-thio-pseudouridine, 5-hydroxy-uridine (ho$^5$U), 5-aminoallyl-uridine, 5-halo-uridine (e.g., 5-iodo-uridine or 5-bromo-uridine), 3-methyl-uridine (m$^3$U), 5-methoxy-uridine (mo$^5$U), uridine 5-oxyacetic acid (cmo$^5$U), uridine 5-oxyacetic acid methyl ester (mcmo$^5$U), 5-carboxymethyl-uridine (cm$^5$U), 1-carboxymethyl-pseudouridine, 5-carboxyhydroxymethyl-uridine (chm$^5$U), 5-carboxyhydroxymethyl-uridine methyl ester (mchm$^5$U), 5-methoxycarbonylmethyl-uridine (mcm$^5$U), 5-methoxycarbonylmethyl-2-thio-uridine (mcm$^5$s2U), 5-aminomethyl-2-thio-uridine (nm$^5$s2U), 5-methylaminomethyl-uridine (mnm$^5$U), 5-methylaminomethyl-2-thio-uridine (mnm⁵s2U), 5-methylaminomethyl-2-seleno-uridine (mnm⁵se²U), 5-carbamoylmethyl-uridine (ncm⁵U), 5-carboxymethylaminomethyl-uridine (cmnm⁵U), 5-carboxymethylaminomethyl-2-thio-uridine (cmnm⁵s2U), 5-propynyl-uridine, 1-propynyl-pseudouridine, 5-taurinomethyl-uridine (τcm⁵U), 1-taurinomethyl-pseudouridine, 5-taurinomethyl-2-thio-uridine(τm⁵s2U), 1-taurinomethyl-4-thio-pseudouridine, 5-methyl-uridine (m⁵U, i.e., having the nucleobase deoxythymine), 1-methyl-pseudouridine (m¹Ψ), 5-methyl-2-thio-uridine (m⁵s2U), 1-methyl-4-thio-pseudouridine (m¹s⁴ψ), 4-thio-1-methyl-pseudouridine, 3-methyl-pseudouridine (m³ψ), 2-thio-1-methyl-pseudouridine, 1-methyl-1-deaza-pseudouridine, 2-thio-1-methyl-1-deaza-pseudouridine, dihydrouridine (D), dihydropseudouridine, 5,6-dihydrouridine, 5-methyl-dihydrouridine (m⁵D), 2-thio-dihydrouridine, 2-thio-dihydropseudouridine, 2-methoxy-uridine, 2-methoxy-4-thio-uridine, 4-methoxy-pseudouridine, 4-methoxy-2-thio-pseudouridine, N1-methyl-pseudouridine, 3-(3-amino-3-carboxypropyl) uridine (acp³U), 1-methyl-3-(3-amino-3-carboxypropyl) pseudouridine (acp³ψ), 5-(isopentenylaminomethyl)uridine (inm⁵U), 5-(isopentenylaminomethyl)-2-thio-uridine (inm⁵s2U), α-thio-uridine, 2'-O-methyl-uridine (Um), 5,2'-O-dimethyl-uridine (m⁵Um), 2'-O-methyl-pseudouridine (ψm), 2-thio-2'-O-methyl-uridine (s2Um), 5-methoxycarbonylmethyl-2'-O-methyl-uridine (mcm⁵Um), 5-carbamoylmethyl-2'-O-methyl-uridine (ncm⁵Um), 5-carboxymethylaminomethyl-2'-O-methyl-uridine (cmnm⁵Um), 3,2'-O-dimethyl-uridine (m³Um), 5-(isopentenylaminomethyl)-2'-O-methyl-uridine (inm⁵Um), 1-thio-uridine, deoxythymidine, 2'-F-ara-uridine, 2'-F-uridine, 2'-OH-ara-uridine, 5-(2-carbomethoxyvinyl) uridine, 5-[3-(1-E-propenylamino)uridine, pyrazolo[3,4-d]pyrimidines, xanthine, and hypoxanthine.

Cytosine

In certain embodiments, the modified nucleobase is a modified cytosine. Exemplary nucleobases and nucleosides having a modified cytosine include without limitation 5-aza-cytidine, 6-aza-cytidine, pseudoisocytidine, 3-methyl-cytidine (m³C), N4-acetyl-cytidine (act), 5-formyl-cytidine (f⁵C), N4-methyl-cytidine (m⁴C), 5-methyl-cytidine (m⁵C), 5-halo-cytidine (e.g., 5-iodo-cytidine), 5-hydroxymethyl-cytidine (hm⁵ C), 1-methyl-pseudoisocytidine, pyrrolo-cytidine, pyrrolo-pseudoisocytidine, 2-thio-cytidine (s2C), 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, lysidine (k²C), α-thio-cytidine, 2'-O-methyl-cytidine (Cm), 5,2'-O-dimethyl-cytidine (m⁵Cm), N4-acetyl-2'-O-methyl-cytidine (ac⁴Cm), N4,2'-O-dimethyl-cytidine (m⁴Cm), 5-formyl-2'-O-methyl-cytidine (f ⁵Cm), N4,N4,2'-O-trimethyl-cytidine (m⁴₂Cm), 1-thio-cytidine, 2'-F-ara-cytidine, 2'-F-cytidine, and 2'-OH-ara-cytidine.

Adenine

In certain embodiments, the modified nucleobase is a modified adenine. Exemplary nucleobases and nucleosides having a modified adenine include without limitation 2-amino-purine, 2,6-diaminopurine, 2-amino-6-halo-purine (e.g., 2-amino-6-chloro-purine), 6-halo-purine (e.g., 6-chloro-purine), 2-amino-6-methyl-purine, 8-azido-adenosine, 7-deaza-adenosine, 7-deaza-8-aza-adenosine, 7-deaza-2-amino-purine, 7-deaza-8-aza-2-amino-purine, 7-deaza-2,6-diaminopurine, 7-deaza-8-aza-2,6-diaminopurine, 1-methyl-adenosine (m¹A), 2-methyl-adenosine (m²A), N6-methyl-adenosine (m⁶A), 2-methylthio-N6-methyl-adenosine (ms2m⁶A), N6-isopentenyl-adenosine (i⁶A), 2-methylthio-N6-isopentenyl-adenosine (ms²i⁶A), N6-(cis-hydroxyisopentenyl)adenosine (io⁶A), 2-methylthio-N6-(cis-hydroxyisopentenyl)adenosine (ms2io⁶A), N6-glycinylcarbamoyl-adenosine (g⁶A), N6-threonylcarbamoyl-adenosine (t⁶A), N6-methyl-N6-threonylcarbamoyl-adenosine (m⁶t⁶A), 2-methylthio-N6-threonylcarbamoyl-adenosine (ms²g⁶A), N6,N6-dimethyl-adenosine (m⁶₂A), N6-hydroxynorvalylcarbamoyl-adenosine (hn⁶A), 2-methylthio-N6-hydroxynorvalylcarbamoyl-adenosine (ms2hn⁶A), N6-acetyl-adenosine (ac⁶A), 7-methyl-adenosine, 2-methylthio-adenosine, 2-methoxy-adenosine, α-thio-adenosine, 2'-O-methyl-adenosine (Am), N⁶,2'-O-dimethyl-adenosine (m⁶Am), N⁶-Methyl-2'-deoxyadenosine, N6,N6,2'-O-trimethyl-adenosine (m⁶₂Am), 1,2'-O-dimethyl-adenosine (m¹Am), 2'-O-ribosyl adenosine (phosphate) (Ar(p)), 2-amino-N6-methyl-purine, 1-thio-adenosine, 8-azido-adenosine, 2'-F-ara-adenosine, 2'-F-adenosine, 2'-OH-ara-adenosine, and N6-(19-amino-pentaoxanonadecyl)-adenosine.

Guanine

In certain embodiments, the modified nucleobase is a modified guanine. Exemplary nucleobases and nucleosides having a modified guanine include without limitation inosine (I), 1-methyl-inosine (m¹I), wyosine (imG), methyl-wyosine (mimG), 4-demethyl-wyosine (imG-14), isowyosine (imG2), wybutosine (yW), peroxywybutosine (o2yW), hydroxywybutosine (OHyW), undermodified hydroxywybutosine (OHyW*), 7-deaza-guanosine, queuosine (Q), epoxyqueuosine (oQ), galactosyl-queuosine (galQ), mannosyl-queuosine (manQ), 7-cyano-7-deaza-guanosine (preQo), 7-aminomethyl-7-deaza-guanosine (preQi), archaeosine (G⁺), 7-deaza-8-aza-guanosine, 6-thio-guanosine, 6-thio-7-deaza-guanosine, 6-thio-7-deaza-8-aza-guanosine, 7-methyl-guanosine (m⁷G), 6-thio-7-methyl-guanosine, 7-methyl-inosine, 6-methoxy-guanosine, 1-methyl-guanosine (m'G), N2-methyl-guanosine (m²G), N2,N2-dimethyl-guanosine (m²₂G), N2,7-dimethyl-guanosine (m²,7G), N2, N2,7-dimethyl-guanosine (m²,2,7G), 8-oxo-guanosine, 7-methyl-8-oxo-guanosine, 1-methyl-6-thio-guanosine, N2-methyl-6-thio-guanosine, N2,N2-dimethyl-6-thio-guanosine, α-thio-guanosine, 2'-O-methyl-guanosine (Gm), N2-methyl-2'-O-methyl-guanosine (m²Gm), N2,N2-dimethyl-2'-O-methyl-guanosine (m²₂Gm), 1-methyl-2'-O-methyl-guanosine (m'Gm), N2,7-dimethyl-2'-O-methyl-guanosine (m²,7Gm), 2'-O-methyl-inosine (Im), 1,2'-O-dimethyl-inosine (m'Im), O⁶-phenyl-2'-deoxyinosine, 2'-O-ribosylguanosine (phosphate) (Gr(p)), 1-thio-guanosine, O⁶-methyl-guanosine, O⁶-Methyl-2'-deoxyguanosine, 2'-F-ara-guanosine, and 2'-F-guanosine.

Exemplary Modified gRNAs

In certain embodiments, the modified nucleic acids can be modified gRNAs. It is to be understood that any of the gRNAs described herein can be modified in accordance with this section, including any gRNA that comprises a targeting domain that comprises a nucleotide sequence selected from the group consisting of SEQ ID NOS: 1-3707. As discussed herein, transiently expressed or delivered nucleic acids can be prone to degradation by, e.g., cellular nucleases. Accordingly, in one aspect the modified gRNAs described herein can contain one or more modified nucleosides or nucleotides which introduce stability toward nucleases. In certain embodiments, certain modified gRNAs described herein can elicit a reduced innate immune response from certain cells, particularly the cells of the present invention (e.g., T-cells).

As noted above, the term "innate immune response" includes a cellular response to exogenous nucleic acids, including single stranded nucleic acids, generally of viral or bacterial origin, which involves the induction of cytokine expression and release, particularly the interferons, and cell death.

For example, as discussed herein, we have seen improvements in ex vivo editing of genes in certain cell types (e.g., T cells) when the 5' end of a gRNA is modified by the inclusion of a eukaryotic mRNA cap structure or cap analog. The present invention encompasses the realization that the improvements observed with a 5' capped gRNA can be extended to gRNAs that have been modified in other ways to achieve the same type of structural or functional result (e.g., by the inclusion of modified nucleosides or nucleotides, by the inclusion of a 3' polyA tract and/or when an in vitro transcribed gRNA is modified by treatment with a phosphatase such as calf intestinal alkaline phosphatase to remove the 5' triphosphate group).

Figure 7:
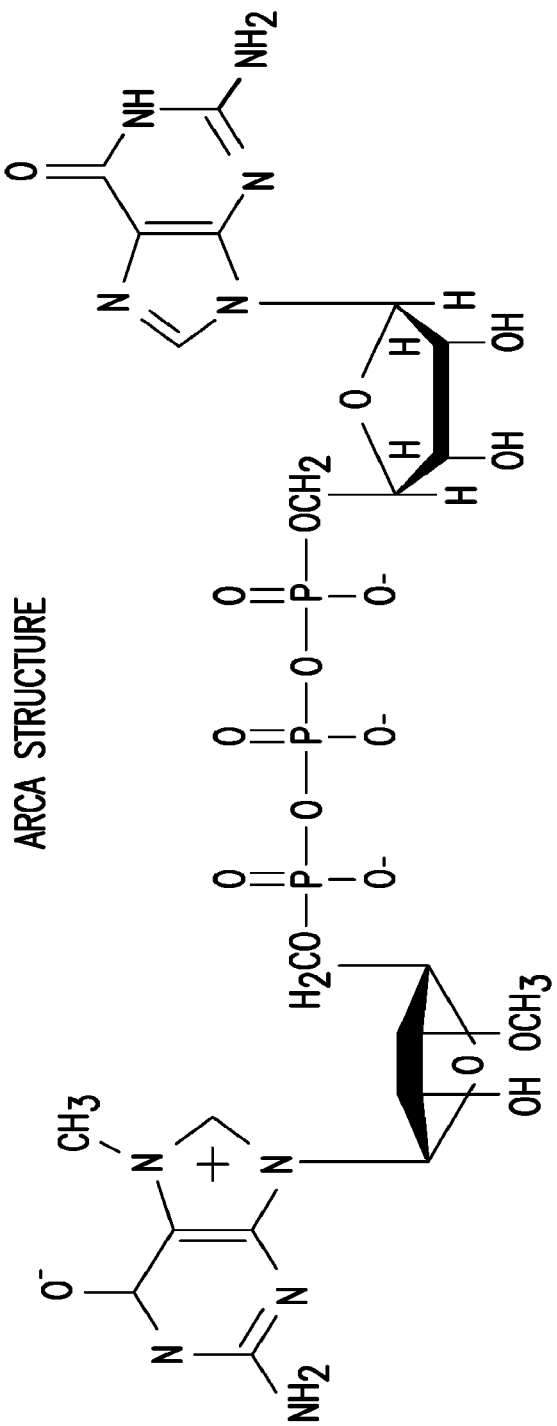
FIG. 7 depicts a eukaryotic mRNA cap structure.

Thus, in certain embodiments, methods and compositions discussed herein provide methods and compositions where gRNAs have been modified at or near their 5' end (e.g., within 1-10, 1-9, 1-8, 1-7, 1-6, 1-5, 1-4, 1-3, or 1-2 nucleotides of their 5' end). In certain embodiments, the 5' end of a gRNA is modified by the inclusion of a eukaryotic mRNA cap structure or cap analog (e.g., a G(5)ppp(5)G cap analog, a m7G(5)ppp(5)G cap analog, or a 3'-O-Me-m7G(5)ppp(5)G anti reverse cap analog (ARCA)) as depicted in FIG. 7. The cap or cap analog can be included during either chemical synthesis or in vitro transcription of the gRNA. In certain embodiments, an in vitro transcribed gRNA is modified by treatment with a phosphatase (e.g., calf intestinal alkaline phosphatase) to remove the 5' triphosphate group.

In certain embodiments, a gRNA comprises a modification at or near its 3' end (e.g., within 1-10, 1-9, 1-8, 1-7, 1-6, 1-5, 1-4, 1-3, or 1-2 nucleotides of its 3' end). For example, in certain embodiments, the 3' end of a gRNA is modified by the addition of one or more (e.g., 25-200) adenine (A) residues. The polyA tract can be contained in the nucleic acid (e.g., plasmid, PCR product, viral genome) encoding the gRNA, or can be added to the gRNA during chemical synthesis, or following in vitro transcription using a polyadenosine polymerase (e.g., E. coli Poly(A)Polymerase). In certain embodiments, gRNAs can be modified at a 3' terminal U ribose. For example, the two terminal hydroxyl groups of the U ribose can be oxidized to aldehyde groups and a concomitant opening of the ribose ring to afford a modified nucleoside as shown below:

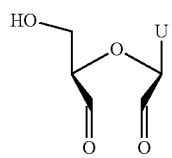

wherein "U" can be an unmodified or modified uridine. In certain embodiments, the 3' terminal U can be modified with a 2'3' cyclic phosphate as shown below:

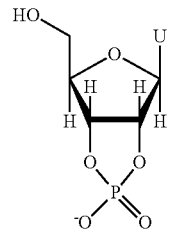

wherein "U" can be an unmodified or modified uridine. In certain embodiments, the gRNA molecules may contain 3' nucleotides which can be stabilized against degradation, e.g., by incorporating one or more of the modified nucleotides described herein. In certain embodiments, e.g., uridines can be replaced with modified uridines, e.g., 5-(2-amino) propyl uridine, and 5-bromo uridine, or with any of the modified uridines described herein; adenosines and guanosines can be replaced with modified adenosines and guanosines, e.g., with modifications at the 8-position, e.g., 8-bromo guanosine, or with any of the modified adenosines or guanosines described herein.

In certain embodiments, a gRNA comprises both a modification at or near its 5' end and a modification at or near its 3' end. In certain embodiments, in vitro transcribed gRNA contains both a 5' cap structure or cap analog and a 3' polyA tract. In certain embodiments, an in vitro transcribed gRNA is modified by treatment with a phosphatase (e.g., calf intestinal alkaline phosphatase) to remove the 5' triphosphate group and comprises a 3' polyA tract.

While the foregoing has focused on terminal modifications, it is to be understood that methods and compositions discussed herein may use gRNAs that include one or more modified nucleosides or nucleotides at one or more non-terminal positions and/or one or more terminal positions within the gRNA sequence.

In certain embodiments, sugar-modified ribonucleotides can be incorporated into the gRNA, e.g., wherein the 2' OH-group is replaced by a group selected from H, —OR, —R (wherein R can be, e.g., alkyl, cycloalkyl, aryl, aralkyl, heteroaryl or sugar), halo, —SH, —SR (wherein R can be, e.g., alkyl, cycloalkyl, aryl, aralkyl, heteroaryl or sugar), amino (wherein amino can be, e.g., NH$_2$; alkylamino, dialkylamino, heterocyclyl, arylamino, diarylamino, heteroarylamino, diheteroarylamino, or amino acid); or cyano (—CN). In certain embodiments, the phosphate backbone can be modified as described herein, e.g., with a phosphothioate group. In certain embodiments, one or more of the nucleotides of the gRNA can each independently be a modified or unmodified nucleotide including, but not limited to 2'-sugar modified, such as, 2'-O-methyl, 2'-O-methoxyethyl, or 2'-Fluoro modified including, e.g., 2'-F or 2'-O-methyl, adenosine (A), 2'-F or 2'-O-methyl, cytidine (C), 2'-F or 2'-O-methyl, uridine (U), 2'-F or 2'-O-methyl, thymidine (T), 2'-F or 2'-O-methyl, guanosine (G), 2'-O-methoxyethyl-5-methyluridine (Teo), 2'-O-methoxyethyladenosine (Aeo), 2'-O-methoxyethyl-5-methylcytidine (m5Ceo), and any combinations thereof.

In certain embodiments, a gRNA can include "locked" nucleic acids (LNA) in which the 2' OH-group can be connected, e.g., by a C1-6 alkylene or C1-6 heteroalkylene bridge, to the 4' carbon of the same ribose sugar, where exemplary bridges can include methylene, propylene, ether, or amino bridges; O-amino (wherein amino can be, e.g., NH$_2$; alkylamino, dialkylamino, heterocyclyl, arylamino, diarylamino, heteroarylamino, or diheteroarylamino, ethylenediamine, or polyamino) and aminoalkoxy or O(CH$_2$)$_n$-amino (wherein amino can be, e.g., NH$_2$; alkylamino, dialkylamino, heterocyclyl, arylamino, diarylamino, heteroarylamino, or diheteroarylamino, ethylenediamine, or polyamino).

In certain embodiments, a gRNA can include a modified nucleotide which is multicyclic (e.g., tricyclo; and "unlocked" forms, such as glycol nucleic acid (GNA) (e.g., R-GNA or S-GNA, where ribose is replaced by glycol units attached to phosphodiester bonds), or threose nucleic acid (TNA, where ribose is replaced with α-L-threofuranosyl-($3'\rightarrow2'$)).

Generally, gRNA molecules include the sugar group ribose, which is a 5-membered ring having an oxygen. Exemplary modified gRNAs can include, without limitation, replacement of the oxygen in ribose (e.g., with sulfur (S), selenium (Se), or alkylene, such as, e.g., methylene or ethylene); addition of a double bond (e.g., to replace ribose with cyclopentenyl or cyclohexenyl); ring contraction of ribose (e.g., to form a 4-membered ring of cyclobutane or oxetane); ring expansion of ribose (e.g., to form a 6- or 7-membered ring having an additional carbon or heteroatom, such as for example, anhydrohexitol, altritol, mannitol, cyclohexanyl, cyclohexenyl, and morpholino that also has a phosphoramidate backbone). Although the majority of sugar analog alterations are localized to the 2' position, other sites are amenable to modification, including the 4' position. In certain embodiments, a gRNA comprises a 4'-S, 4'-Se or a 4'-C-aminomethyl-2'-O-Me modification.

In certain embodiments, deaza nucleotides, e.g., 7-deazaadenosine, can be incorporated into the gRNA. In certain embodiments, O- and N-alkylated nucleotides, e.g., N6-methyl adenosine, can be incorporated into the gRNA. In certain embodiments, one or more or all of the nucleotides in a gRNA molecule are deoxynucleotides.

XI. Inhibitory Cpf1 gRNA Molecules and the Use Thereof to Limit the Activity of a Cpf1 System Methods and compositions that use, or include, a nucleic acid, e.g., DNA, that encodes a Cpf1 molecule or a gRNA molecule, can, in addition, use or include an "inhibitory Cpf1 gRNA molecule." The inhibitory Cpf1 gRNA can limit the activity of the other CRISPR/Cpf1 components introduced into a cell or subject. In certain embodiments, a gRNA molecule comprises a targeting domain that is complementary to a target domain on a nucleic acid that comprises a sequence that encodes a component of the CRISPR/Cpf1 system that is introduced into a cell or subject. In certain embodiments, an inhibitory Cpf1 gRNA molecule comprises a targeting domain that is complementary with a target sequence on: (a) a nucleic acid that encodes a Cpf1 molecule; (b) a nucleic acid that encodes a gRNA molecule which comprises a targeting domain that targets the FAS, BID, CTLA4, PDCD1, CBLB, PTPN6, B2M, TRAC and/or TRBC gene (a target gene gRNA); or on more than one nucleic acid that encodes a CRISPR/Cpf1 component, e.g., both (a) and (b). The inhibitory Cpf1 gRNA molecule can complex with the Cpf1 molecule to inactivate a component of the system. In certain embodiments, a Cpf1 molecule/inhibitory Cpf1 gRNA molecule complex inactivates a nucleic acid that comprises the sequence encoding the Cpf1 molecule. In certain embodiments, a Cpf1 molecule/inhibitory Cpf1 gRNA molecule complex inactivates the nucleic acid that comprises the sequence encoding a target gene gRNA molecule. In certain embodiments, a Cpf1 molecule/inhibitory Cpf1 gRNA molecule complex places temporal, level of expression, or other limits, on activity of the Cpf1 molecule/target gene gRNA molecule complex. In certain embodiments, a Cpf1 molecule/inhibitory Cpf1 gRNA molecule complex reduces off-target or other unwanted activity. In certain embodiments, an inhibitory Cpf1 gRNA molecule targets the coding sequence, or a control region, e.g., a promoter, for the CRISPR/Cpf1 system component to be negatively regulated. For example, an inhibitory Cpf1 gRNA can target the coding sequence for a Cpf1 molecule, or a control region, e.g., a promoter, that regulates the expression of the Cpf1 molecule coding sequence, or a sequence disposed between the two. In certain embodiments, an inhibitory Cpf1 gRNA molecule targets the coding sequence, or a control region, e.g., a promoter, for a target gene gRNA. In certain embodiments, an inhibitory Cpf1 gRNA, e.g., a Cpf1-targeting or target gene gRNA-targeting, inhibitory Cpf1 gRNA molecule, or a nucleic acid that encodes it, is introduced separately, e.g., later, than is the Cpf1 molecule or a nucleic acid that encodes it. For example, a first vector, e.g., a viral vector, e.g., an AAV vector, can introduce nucleic acid encoding a Cpf1 molecule and one or more target gene gRNA molecules, and a second vector, e.g., a viral vector, e.g., an AAV vector, can introduce nucleic acid encoding an inhibitory Cpf1 gRNA molecule, e.g., a Cpf1-targeting or target gene gRNA targeting, gRNA molecule. In certain embodiments, the second vector can be introduced after the first. In certain embodiments, an inhibitory Cpf1 gRNA molecule, e.g., a Cpf1-targeting or target gene gRNA targeting, an inhibitory Cpf1 gRNA molecule, or a nucleic acid that encodes it, can be introduced together, e.g., at the same time or in the same vector, with the Cpf1 molecule or a nucleic acid that encodes it, but, e.g., under transcriptional control elements, e.g., a promoter or an enhancer, that are activated at a later time, e.g., such that after a period of time the transcription of Cpf1 is reduced. In certain embodiments, the transcriptional control element is activated intrinsically. In certain embodiments, the transcriptional element is activated via the introduction of an external trigger.

Typically a nucleic acid sequence encoding an inhibitory Cpf1 gRNA molecule, e.g., a Cpf1-targeting gRNA molecule, is under the control of a different control region, e.g., promoter, than is the component it negatively modulates, e.g., a nucleic acid encoding a Cpf1 molecule. In certain embodiments, "different control region" refers to simply not being under the control of one control region, e.g., promoter, that is functionally coupled to both controlled sequences. In certain embodiments, different refers to "different control region" in kind or type of control region. For example, the sequence encoding an inhibitory Cpf1 gRNA molecule, e.g., a Cpf1-targeting gRNA molecule, is under the control of a control region, e.g., a promoter, that has a lower level of expression, or is expressed later than the sequence which encodes is the component it negatively modulates, e.g., a nucleic acid encoding a Cpf1 molecule.

By way of example, a sequence that encodes an inhibitory Cpf1 gRNA molecule, e.g., a Cpf1-targeting inhibitory Cpf1 gRNA molecule, can be under the control of a control region (e.g., a promoter) described herein, e.g., human U6 small nuclear promoter, or human H1 promoter. In certain embodiments, a sequence that encodes the component it negatively regulates, e.g., a nucleic acid encoding a Cpf1 molecule, can be under the control of a control region (e.g., a promoter) described herein, e.g., CMV, EF-1a, MSCV, PGK, CAG control promoters.

EXAMPLES

The following Examples are merely illustrative and are not intended to limit the scope or content of the invention in any way.

Example 1

Delivery of Cpf1/rRNA RNP to T Cells

To demonstrate Cpf1-mediated cutting in primary CD4+ T cells, purified *Acidaminococcus* sp BV3L6 Cpf1 ("AsCpf1") was complexed with 11 different gRNA (also referred to as "crRNAs") designed against the TCR alpha chain (Table 6). GWED539 comprises a direct repeat domain having the nucleotide sequence set forth in SEQ ID NO: 3708, and a targeting domain having the nucleotide sequence set forth in SEQ ID NO: 3433. GWED540 comprises a direct repeat domain having the nucleotide sequence set forth in SEQ ID NO: 3708, and a targeting domain having the nucleotide sequence set forth in SEQ ID NO: 3587. GWED541 comprises a direct repeat domain having the nucleotide sequence set forth in SEQ ID NO: 3708, and a targeting domain having the nucleotide sequence set forth in SEQ ID NO: 3538. GWED542 comprises a direct repeat domain having the nucleotide sequence set forth in SEQ ID NO: 3708, and a targeting domain having the nucleotide sequence set forth in SEQ ID NO: 3461. GWED543 comprises a direct repeat domain having the nucleotide sequence set forth in SEQ ID NO: 3708, and a targeting domain having the nucleotide sequence set forth in SEQ ID NO: 3475. GWED544 comprises a direct repeat domain having the nucleotide sequence set forth in SEQ ID NO: 3708, and a targeting domain having the nucleotide sequence set forth in SEQ ID NO: 3524. GWED545 comprises a direct repeat domain having the nucleotide sequence set forth in SEQ ID NO: 3708, and a targeting domain having the nucleotide sequence set forth in SEQ ID NO:3566. GWED546 comprises a direct repeat domain having the nucleotide sequence set forth in SEQ ID NO: 3708, and a targeting domain having the nucleotide sequence set forth in SEQ ID NO: 3517. GWED547 comprises a direct repeat domain having the nucleotide sequence set forth in SEQ ID NO: 3708, and a targeting domain having the nucleotide sequence set forth in SEQ ID NO: 3573. GWED548 comprises a direct repeat domain having the nucleotide sequence set forth in SEQ ID NO: 3708, and a targeting domain having the nucleotide sequence set forth in SEQ ID NO: 3580. GWED549 comprises a direct repeat domain having the nucleotide sequence set forth in SEQ ID NO: 3708, and a targeting domain having the nucleotide sequence set forth in SEQ ID NO:3454.

TABLE 6

| crRNA ID | crRNA sequence | SEQ ID NO |
|---|---|---|
| GWED539 | UAAUUUCUACUCUUGUAGAUAGAAUCAAAAUCGGUGAAUAGGC | 3711 |
| GWED540 | UAAUUUCUACUCUUGUAGAUUUUGAGAAUCAAAAUCGGUGAAU | 3712 |
| GWED541 | UAAUUUCUACUCUUGUAGAUGUCUGUGAUAUACACAUCAGAAU | 3713 |
| GWED542 | UAAUUUCUACUCUUGUAGAUCACAUGCAAAGUCAGAUUUGUUG | 3714 |
| GWED543 | UAAUUUCUACUCUUGUAGAUCAUGUGCAAACGCCUUCAACAAC | 3715 |
| GWED544 | UAAUUUCUACUCUUGUAGAUGAUUCUCAAACAAAUGUGUCACA | 3716 |
| GWED545 | UAAUUUCUACUCUUGUAGAUUCUGUGAUAUACACAUCAGAAUC | 3717 |
| GWED546 | UAAUUUCUACUCUUGUAGAUGAGUCUCUCAGCUGGUACACGGC | 3718 |
| GWED547 | UAAUUUCUACUCUUGUAGAUUGACACAUUUGUUUGAGAAUCAA | 3719 |
| GWED548 | UAAUUUCUACUCUUGUAGAUUUGCUCCAGGCCACAGCACUGUU | 3720 |
| GWED549 | UAAUUUCUACUCUUGUAGAUAUUCUCAAACAAAUGUGUCACAA | 3721 |

Each RNP complex was delivered by electroporation and the ability of the individual RNPs to target and cut the TRAC locus was evaluated by flow cytometry (FCM) and a T7E1 assay.

Purification of AsCpf1 Enzyme

A 3.9 Kb gene segment corresponding to the 1307 residues of AsCpf1 was obtained by gene synthesis with appended SapI Electra cloning arms (DNA 2.0 cloning system) and a C-term nucleoplasmin NLS. The synthetic construct cloned into pUC57 vector was excised by SapI digestion and Electra-cloned (DNA 2.0, Electra cloning system) into pD441-NH, pD441-CH (high copy) and pD421-NH (low copy) E. coli expression vectors.

After plasmids containing the AsCpf1 gene (either N-term His (high copy), C-term His (high copy), or N-term His (low copy) were transformed or electroporated into bacterial expression strains, protein was expressed and purified using the following method. All AsCpf1 constructs also contain a C-terminal nucleplasmin NLS sequence but are also amenable to an SV40 NLS on either N- or C-termini. After plasmids were transformed or electroporated into protein expression bacteria cells (e.g., Rosetta 2 cells) several resulting colonies were added to 0.5 mL Brain Heart and Lung (BHL) media or another rich media w/out antibiotics. After 30 min to 1 hour, or when cell suspension was visibly cloudy, 0.5 mL BHL media or other rich media and antibiotics (chloramphenicol and kanamycin) were added to culture. The culture volume was doubled once the culture became visibly cloudy (OD=0.6) until volume reached 8 mL. Full culture was then transferred up to 1 L of Terrific broth (Teknova) media+antibiotics+1 mL 1000× metals solution (Teknova)+200 µL of 1 M magnesium sulfate solution. Cultures were grown at 37° C. Culture OD was measured after 1-2 hours or when the culture flask became slightly cloudy. At this point, the OD was measured every 1 hour or when appropriate until OD reached 1.0-1.5. Once OD reached 1.0-1.5, the flask was transferred to a lower temperature (18° C. to 25° C.) and the OD was checked again 30 minutes to 1 hour later. When the culture reached an OD of ~2.0, protein expression was induced by adding IPTG. The cells were grown at 18° C. for 12-16 hours (this time can be varied as necessary up to 3 days). Cultures were then harvested and pelleted using a large centrifuge and either lysed immediately or kept frozen at −80 C till the day of lysis.

Cell pellets expressing AsCpf1 were lysed using a microfluidizer wherein 1-10 g of dry cell pellet was resuspended with 70 mL of lysis buffer (50 mM Tris pH 8.0, 1 mM TCEP [tris(2-carboxyethyl)phosphine)] or DTT (dithiothreitol), 10-20% glycerol, and 300-1000 mM NaCl or KCl. Alternatively, cells were lysed and folded AsCpf1 was extracted using the BPER (ThermoFisher) chemical lysis kit, the BugBuster (EMD Millipore) chemical lysis kit, or an in-house chemical lysis reagent containing the same buffer but also in the presence of 1% Triton X-100 to break down cell membranes. Finally, a sonicator can be used to lyse cells using the same lysis buffer in the microfluidizer method but without 1% Triton X-100 or any other mild zwitter-ion detergent.

Cell lysate was spun down in a centrifuge and cell debris pellet was discarded. The supernatant was filtered through a 0.2 µm or 0.45 µm filter and loaded onto either a HisTrap Ni-NTA column (GE Healthcare) on onto a gravity column using HIsPur Ni-NTA slurry (Thermo Fisher). In both cases the HisTrap or slurry in the gravity column were equilibrated with lysis buffer before being exposed to several 5×-20× column volume washes with lysis buffer also containing 30 mM imidazole. Finally, His-tagged AsCpf1 was eluted from Ni-NTA resin from either the HisTrap or gravity column using lysis buffer with 250-500 mM imidazole.

AsCpf1 protein was then concentrated using a filter with a molecular weight cutoff of 100 kDa or less to approximately 5 mL and loaded onto an AKTA Pure (GE Healthcare) FPLC instrument equipped with a size-exclusion column. Alternatively, due to its net positive charge of the 6× His-AsCpf1-NLS construct (+8), AsCpf1 can also be loaded onto a cation-exchange column and purified using a 100 mM to 1000 mM NaCl gradient over 40 minutes. NaCl can also be substituted with KCl. Alternatively, AsCpf1 (+3 net charge) with a 3× FLAG tag (−7 net charge) and no NLS (+5 net charge) would bear a negative charge and be able to bind an anion-exchange column and be purified with an increasing salt gradient. The buffer for either the size-exclusion purification method or the cation-exchange purification method is 50 mM HEPES, pH 7.5, 1 mM TCEP or DTT, 10%-20% glycerol, and either 250 mM NaCl constant ionic strength (Size-exclusion) or 100 mM to 1000 mM NaCl ionic strength (cation-exchange). HEPES can be substituted for any buffer that has a buffering capacity in the range of pH 6.5-8.5. AsCpf1 protein was eluted into 2 mL fractions, yielding one predominant peak as detected by UV-absorbance on the FPLC instrument. Fractions from this peak were pooled and AsCpf1 was determined to be present and of high purity as analyzed by SDS-PAGE, which showed a clear band without contaminating bands at the expected 150 kDa molecular weight marker. In addition, inspection of the AsCpf1 absorbance spectra showed a clean protein without measurable nucleic acid contamination as measured by 260/280 UV-absorbance ratio.

Pooled fractions of AsCpf1 were concentrated down to 50 µM based on the predicted extinction coefficient of AsCpf1 ($143,940$ $M^{-1}$ $cm^{-1}$) as indicated on UniProt Prot-param tool on the NCBI website and the measured 280 absorbance. These aliquots were either stored at 4 C for immediate use or flash-frozen in liquid nitrogen and stored at −80 C for long term storage.

Figure 2:
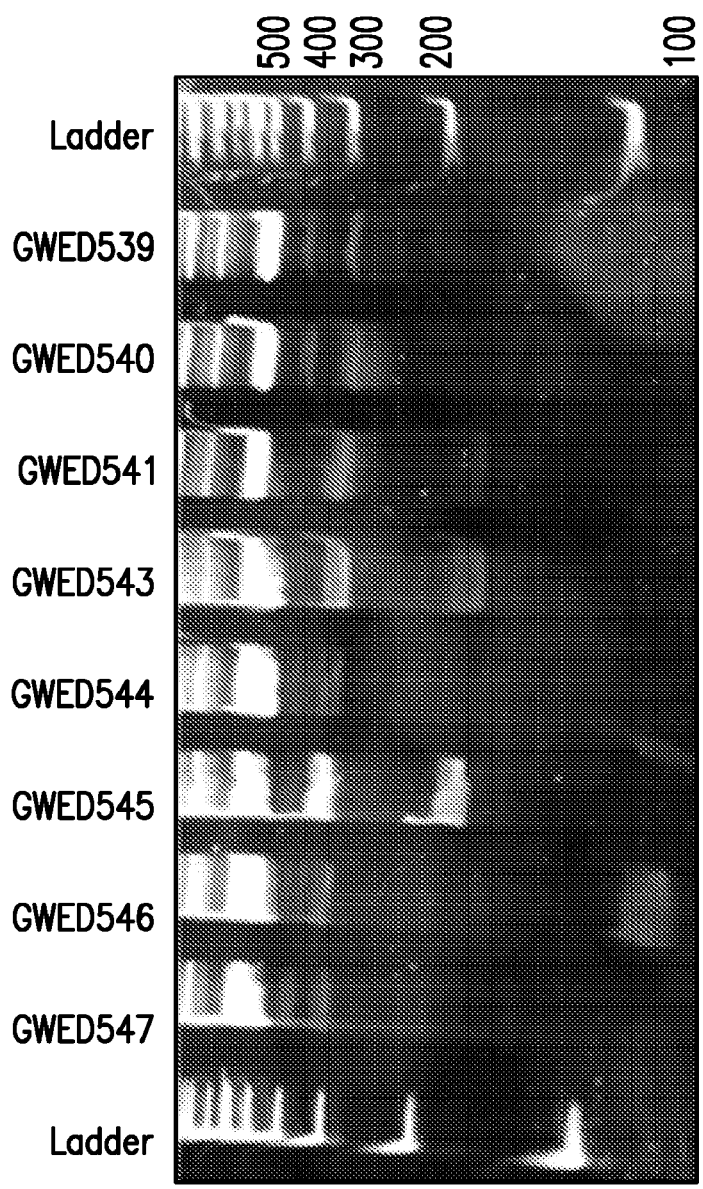
FIG. 2 depicts assessment of Cpf1 RNPs in biochemical cutting assay. The activity of several RNPs that target the TRAC locus was assessed in an in vitro cutting assay. A PCR product corresponding to 450 bp of exon 1 of TRAC was incubated at a 1:1 ratio with the TRAC RNPs identified. The approximate expected sizes of bands that a successful cut should produce are listed for each TRAC RNP. Although all RNPs appeared to have activity, two RNPs seemed to be more active—GWED545 and GWED546.
Figure 3A:
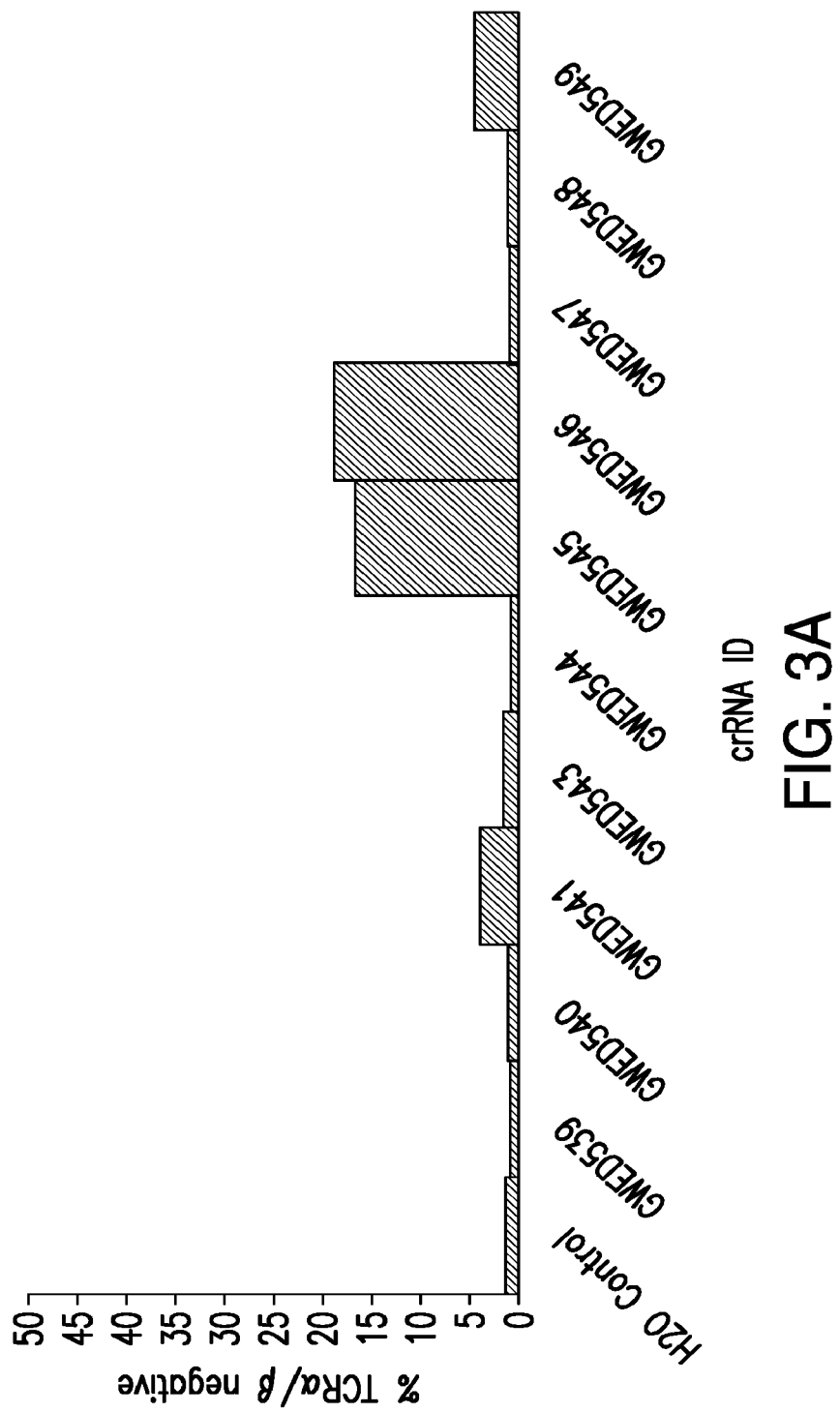
FIGS. 3A and 3B depict analysis of TCRα/β expression in CD4+ T cells treated with Cpf1 TRAC specific RNPs. (A) Activated human CD4+ T cells were electroporated with RNPs designed to target the TRAC locus. On day 4 post electroporation, the cells were stained with a TCRα/β antibody and analyzed by FCM. The frequency of TCRα/β negative cells was graphed for each crRNA tested. Treatment with two RNPs (GWED545 and GWED546) resulted in a significant frequency of TCRα/β negative cells, indicating the ability of these RNPs to successfully edit the TRAC locus resulting in a reduction of surface protein expression. (B) Representative FCM plotted for the two RNPs that resulted in significant TCRα/β negative cells as compared to the Cpf1 apo control and an RNP that failed to delete surface TCRα/β cells in this assay.
Figure 3B:
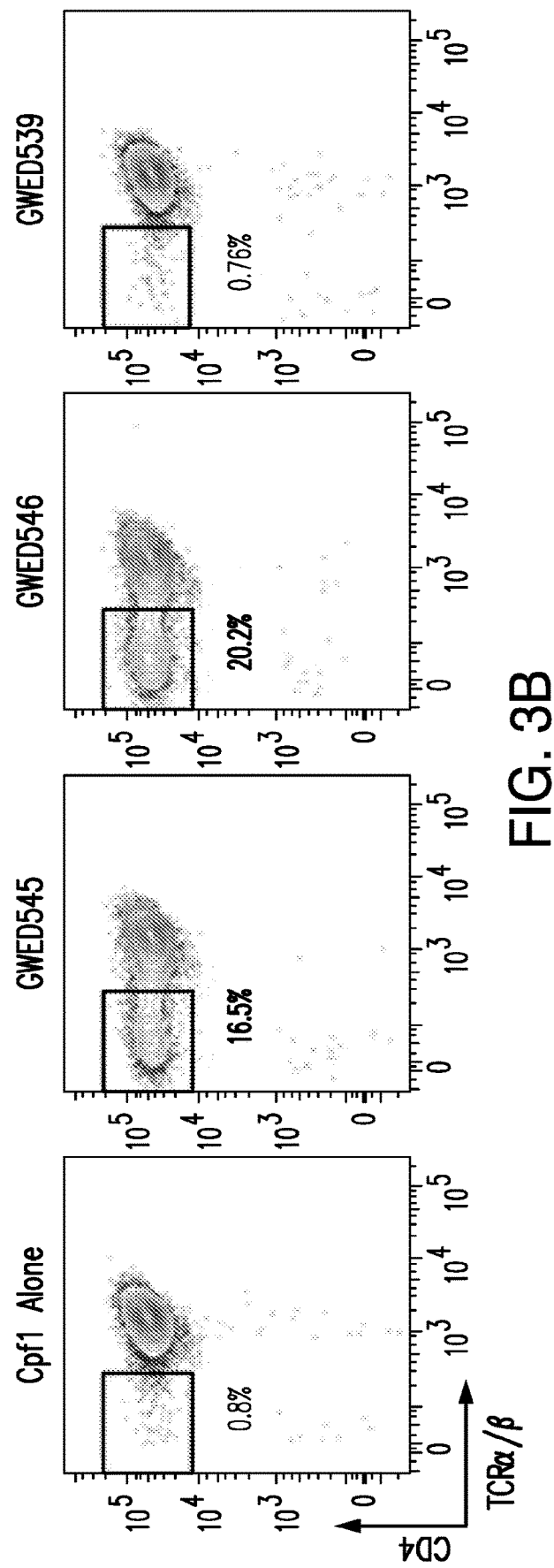
Figure 4:
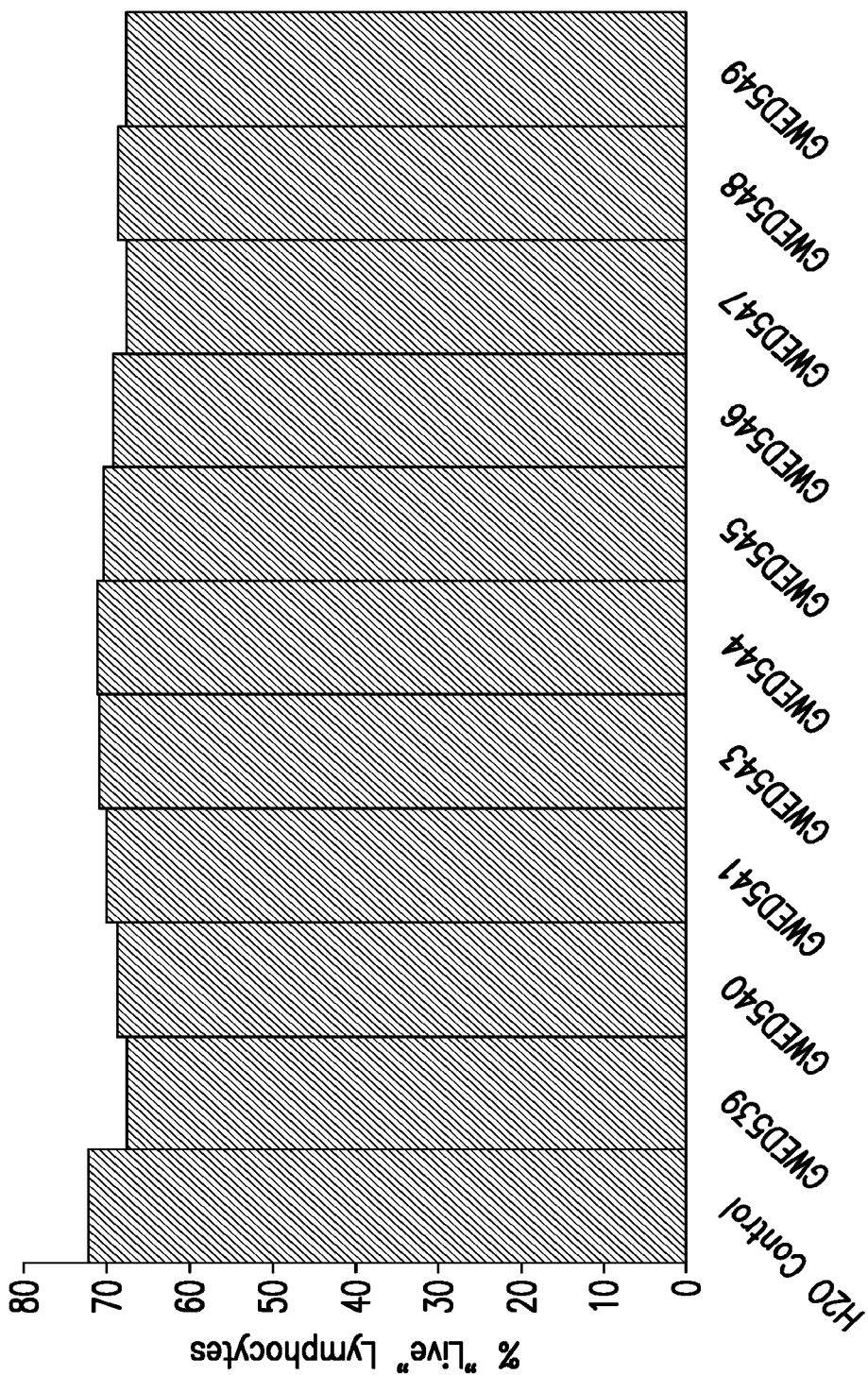
FIG. 4 depicts viability of Cpf1 RNPs. Treatment of the cells with Cpf1 RNPs did not result in a loss of viability. The frequency of live lymphocytes was determined by position on forward scatter versus side scatter for each RNP. The frequency of live lymphocytes was graphed for each RNP tested.
Figure 5:
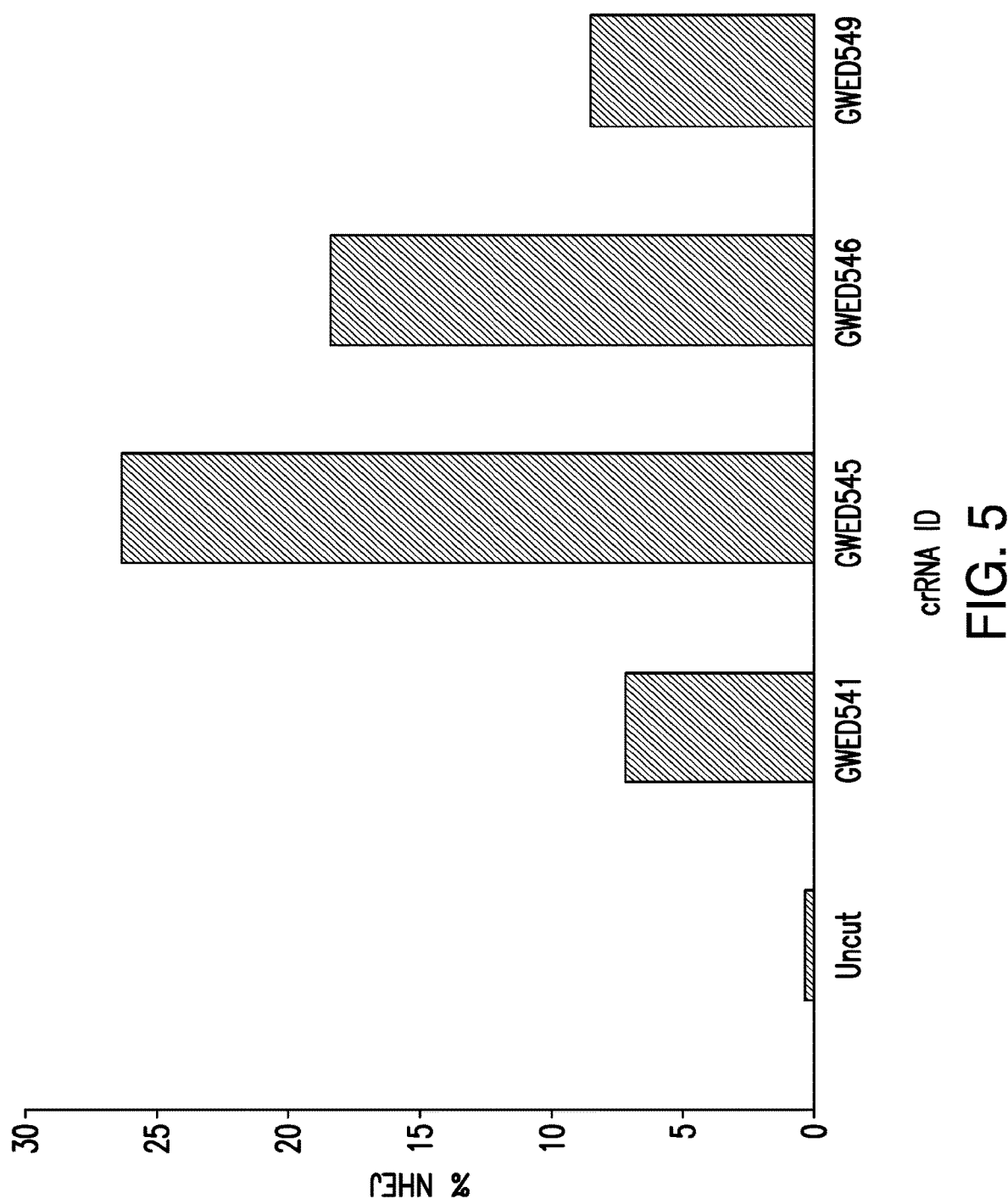
FIG. 5 depicts molecular analysis by T7E1 for ability of Cpf1 to edit human T cells. The results confirmed that Cpf1 can edit human T cells. The gDNA from the RNP treated human T cells was harvested on day 4 post electroporation. The TRAC locus was amplified using specific primers and the PCR product was subjected to a T7E1 assay. Briefly, the PCR product was denatured, reannealed, and finally treated with the T7E1 enzyme. This enzyme cleaved double stranded DNA with mispairing at the site of mispairing. The rate of cleavage by the T7E1 enzyme as assessed by quantification of the cleavage products on an agarose gel was related to the percentage of genome editing at the targeted locus. The data from this assay were plotted and supports the data observed by FACS in FIG. 3.

The crRNA was generated by chemical synthesis and complexed to the aforementioned purified protein prior to delivery to the cells by incubating the protein and crRNA at room temperature for a minimum of 15 minutes. The complexed RNP was used in two separate assays. The RNP was used in an in vitro cutting assay in which the RNP was incubated with a PCR product corresponding to exon1 of the TRAC locus. The RNP was incubated with the PCR product at a 1:1 molar ratio and allowed to incubate for 15 minutes at 37° C. Following incubation, the reaction was treated with Proteinase K for 20 minutes at 42° C. Cutting was visualized on a PAGE gel. Although cutting was observed for most of the RNPs, two showed significant cutting (FIG. 2). A fraction of each RNP complex was also introduced into activated primary human CD4$^+$ T cells (cultured in complete media supplemented with IL-2, IL-7, IL-15) by electroporation at a ratio of 1 ug/100,000 cells. TCRα/β expression on the cells was monitored at 4 days post electroporation by FCM using a Brilliant Violet 421 (BioLegend) conjugated antibody specific for TCRα/β. Two RNPs (GWED545 and GWED546) significantly reduced the expression of TCRα/β on transfected cells, compared with many RNPs that did not affect expression of TCRα/β (FIG. 3). Additionally, cell viability was not negatively affected by the treatment with Cpf1 RNPs (FIG. 4). To confirm that the generation of TCRα/β negative cells was a result of genome editing at the TRAC locus, gDNA was harvested and a T7E1 assay was performed. Briefly, the T7E1 assay involves amplification, purification and size-verification of a 450 bp PCR product, denaturation of the PCR product and re-hybridized by heating to 95° C. and then slowly cooling. Hybridized PCR products were then digested with T7 Endonuclease I (or other mismatch-sensitive enzyme) which recognized and cleaved non-perfectly matched DNA. If indels were present in the original template DNA, when the amplicons were denatured and re-annealed, this resulted in the hybridization of DNA strands harboring different indels and therefore led to double-stranded DNA that is not perfectly matched. Digestion products may be visualized by gel electrophoresis or by capillary electrophoresis. The fraction of DNA that was cleaved (density of cleavage products divided by the density of cleaved and uncleaved) was used to estimate a percent NHEJ using the following equation: % NHEJ=(1−(1−fraction cleaved)½. The T7E1 assay was sensitive down to about 2-5% NHEJ. Indeed, the data confirm the presence of DNA modifications at the TRAC locus for the RNPs that reduced TCRα/β expression (FIG. 5).

Figure 6:
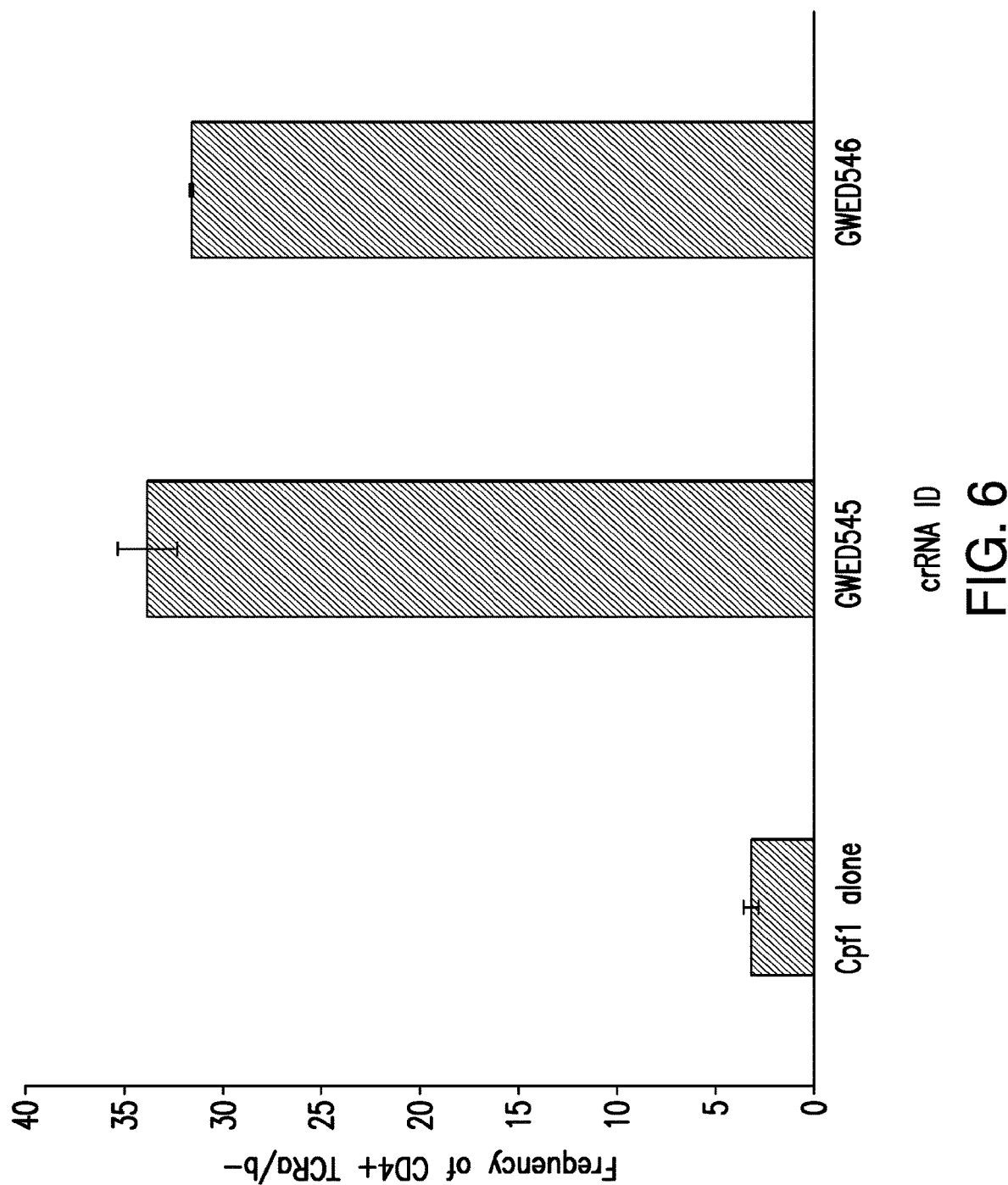
FIG. 6 depicts analysis of TCRα/β expression in CD4+ T cells from a second donor that were treated with Cpf1 TRAC specific RNPs. Activated human CD4+ T cells were electroporated with RNPs corresponding to GWED545 and GWED546. On day 4 post electroporation, the cells were stained with a TCRα/β antibody and analyzed by FCM. The frequency of TCRα/β negative cells was graphed. The loss of TCRα/β in cells treated with Cpf1 RNPs GWED545 and GWED546 demonstrates that Cpf1 can reproducibly edit human T cells across multiple donors.

To determine whether Cpf1 can cut human T cells derived from more than one donor, RNPs comprised of GWED545 and GWED546 crRNAs were electroporated into activated human T cells from a second donor. The editing efficiency was assessed by FACS analysis at day 4 post electroporation by FCM using a Brilliant Violet 421 (BioLegend) conjugated antibody specific for TCRα/β. The ability of these two RNPs to edit human T cells across two donors was confirmed by the loss of TCRα/β expression (FIG. 6).

INCORPORATION BY REFERENCE

All publications, patents, sequence listings, and patent applications mentioned herein are hereby incorporated by reference in their entirety as if each individual publication, patent, sequence listing, or patent application was specifically and individually indicated to be incorporated by reference. In case of conflict, the present application, including any definitions herein, will control.

EQUIVALENTS

Those skilled in the art will recognize, or be able to ascertain using no more than routine experimentation, many equivalents to the specific embodiments of the invention described herein. Such equivalents are intended to be encompassed by the following claims. Certain embodiments are also within the following claims.

SEQUENCE LISTING

The patent contains a lengthy sequence listing. A copy of the sequence listing is available in electronic form from the USPTO web site (https://seqdata.uspto.gov/?pageRequest=docDetail&DocID=US12325854B2). An electronic copy of the sequence listing will also be available from the USPTO upon request and payment of the fee set forth in 37 CFR 1.19(b)(3).

What is claimed is:

1. A population of T cells, wherein the T cells comprise a complex comprising a CRISPR from *Prevotella* and *Franciscella* 1 (Cpf1) RNA-guided nuclease and a gRNA molecule comprising a targeting domain that is complementary to a sequence of a TRAC gene,
   wherein the targeting domain consists of the nucleotide sequence set forth in SEQ ID NO: 3514 or SEQ ID NO: 3515, and
   wherein at least 30% of the T cells comprise an indel in the TRAC gene.

2. The population of claim 1, wherein the T cells are CD8+ T cells.

3. The population of claim 2, wherein the CD8+ T cells are CD8+ naïve T cells, central memory T cells, or effector memory T cells.

4. The population of claim 1, wherein the T cells are engineered T cells, and wherein the engineered T cells are engineered chimeric antigen receptor (CAR) T cells or engineered TCR (T cell receptor) T cells.

5. A population of immune cells comprising an RNP complex comprising a CRISPR from *Prevotella* and *Franciscella* 1 (Cpf1) RNA-guided endonuclease and one or more gRNAs, wherein the gRNA comprises a targeting domain that is complementary to a nucleic acid sequence of a TRAC gene,
   wherein the targeting domain consists of the nucleotide sequence set forth in SEQ ID NO: 3514 or SEQ ID NO: 3515, and
   wherein at least 30% of the immune cells comprise an indel in the TRAC gene.

6. The population of claim 5, wherein the RNP complex is delivered into the immune cells via electroporation.

7. The population of claim 1, wherein the T cells are selected from the group consisting of CD8+ T cells, central memory T cells, effector memory T cells, CD4+ T cells, NKT cells, regulatory T cells (Tregs) and stem cell memory T cells.

8. The population of claim 1, wherein the targeting domain consists of the nucleotide sequence set forth in SEQ ID NO: 3515.

9. The population of claim 5, wherein the targeting domain consists of the nucleotide sequence set forth in SEQ ID NO: 3515.

* * * * *

UNITED STATES PATENT AND TRADEMARK OFFICE
CERTIFICATE OF CORRECTION

| | | |
|---|---|---|
| PATENT NO. | : 12,325,854 B2 | Page 1 of 1 |
| APPLICATION NO. | : 16/121152 | |
| DATED | : June 10, 2025 | |
| INVENTOR(S) | : Welstead et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 475 days.

Signed and Sealed this
Sixteenth Day of December, 2025

John A. Squires
*Director of the United States Patent and Trademark Office*